(12) United States Patent
Dalebout et al.

(10) Patent No.: US 10,940,360 B2
(45) Date of Patent: *Mar. 9, 2021

(54) STRENGTH EXERCISE MECHANISMS

(71) Applicant: ICON Health & Fitness, Inc., Logan, UT (US)

(72) Inventors: William T. Dalebout, North Logan, UT (US); Gordon Cutler, Providence, UT (US)

(73) Assignee: ICON Health & Fitness, Inc., Logan, UT (US)

( * ) Notice: Subject to any disclaimer, the term of this patent is extended or adjusted under 35 U.S.C. 154(b) by 39 days.

This patent is subject to a terminal disclaimer.

(21) Appl. No.: 15/245,473

(22) Filed: Aug. 24, 2016

(65) Prior Publication Data

US 2017/0056711 A1 Mar. 2, 2017

Related U.S. Application Data

(60) Provisional application No. 62/210,318, filed on Aug. 26, 2015.

(51) Int. Cl.
*A63B 21/00* (2006.01)
*A63B 23/035* (2006.01)
(Continued)

(52) U.S. Cl.
CPC ............ *A63B 22/02* (2013.01); *A61B 5/6895* (2013.01); *A63B 21/00047* (2013.01);
(Continued)

(58) Field of Classification Search
CPC ............ A63B 21/4035; A63B 22/0235; A63B 22/0046; A63B 23/03516; A63B 21/068;
(Continued)

(56) References Cited

U.S. PATENT DOCUMENTS 9,595 A 2/1853 Moreland
9,695 A 5/1853 Hinsdale
(Continued)

FOREIGN PATENT DOCUMENTS

CN 203989681 12/2014
KR 100829774 5/2008
(Continued)

OTHER PUBLICATIONS

International Search Report and Written Opinion issued for PCT/US2016/048692 dated Dec. 1, 2016.
(Continued)

*Primary Examiner* — Loan B Jimenez
*Assistant Examiner* — Shila Jalalzadeh Abyaneh
(74) *Attorney, Agent, or Firm* — Ray Quinney & Nebeker

(57) ABSTRACT

A treadmill includes a frame, an exercise deck attached to the frame, and a first handle movably attached to the frame. The first handle has a first orientation where the first handle is positioned within a region above the exercise deck and stabilized to support a user's weight during a body weight exercise, and a second orientation where the first handle is positioned away from the region above the exercise deck.

19 Claims, 10 Drawing Sheets

(51) Int. Cl.
| | |
|---|---|
| A63B 22/00 | (2006.01) |
| A63B 22/02 | (2006.01) |
| A63B 23/12 | (2006.01) |
| A63B 23/02 | (2006.01) |
| A63B 23/00 | (2006.01) |
| A63B 71/06 | (2006.01) |
| G16H 20/30 | (2018.01) |
| A61B 5/00 | (2006.01) |
| G09B 19/00 | (2006.01) |
| A63B 1/00 | (2006.01) |
| A63B 17/04 | (2006.01) |
| A63B 21/16 | (2006.01) |
| A63B 24/00 | (2006.01) |
| A61B 5/11 | (2006.01) |
| A61B 5/0205 | (2006.01) |
| A63B 21/072 | (2006.01) |
| A63B 21/068 | (2006.01) |

(52) U.S. Cl.
CPC ...... *A63B 21/4035* (2015.10); *A63B 22/0007* (2013.01); *A63B 22/0046* (2013.01); *A63B 22/0235* (2013.01); *A63B 23/03516* (2013.01); *A63B 71/0622* (2013.01); *G09B 19/0038* (2013.01); *G16H 20/30* (2018.01); *A61B 5/0205* (2013.01); *A61B 5/1128* (2013.01); *A61B 2503/10* (2013.01); *A63B 1/00* (2013.01); *A63B 17/04* (2013.01); *A63B 21/068* (2013.01); *A63B 21/0726* (2013.01); *A63B 21/16* (2013.01); *A63B 21/169* (2015.10); *A63B 21/1618* (2013.01); *A63B 22/0023* (2013.01); *A63B 23/0216* (2013.01); *A63B 23/03525* (2013.01); *A63B 23/03541* (2013.01); *A63B 23/03558* (2013.01); *A63B 23/1218* (2013.01); *A63B 23/1227* (2013.01); *A63B 23/1236* (2013.01); *A63B 24/0087* (2013.01); *A63B 2023/006* (2013.01); *A63B 2071/063* (2013.01); *A63B 2071/065* (2013.01); *A63B 2071/0638* (2013.01); *A63B 2071/0655* (2013.01); *A63B 2071/0658* (2013.01); *A63B 2220/05* (2013.01); *A63B 2220/10* (2013.01); *A63B 2220/13* (2013.01); *A63B 2220/17* (2013.01); *A63B 2220/20* (2013.01); *A63B 2220/30* (2013.01); *A63B 2220/31* (2013.01); *A63B 2220/52* (2013.01); *A63B 2220/62* (2013.01); *A63B 2220/70* (2013.01); *A63B 2220/72* (2013.01); *A63B 2220/73* (2013.01); *A63B 2220/74* (2013.01); *A63B 2220/75* (2013.01); *A63B 2220/806* (2013.01); *A63B 2220/807* (2013.01); *A63B 2225/20* (2013.01); *A63B 2225/50* (2013.01); *A63B 2230/00* (2013.01); *A63B 2230/01* (2013.01); *A63B 2230/06* (2013.01); *A63B 2230/207* (2013.01); *A63B 2230/30* (2013.01); *A63B 2230/40* (2013.01); *A63B 2230/62* (2013.01); *A63B 2230/75* (2013.01)

(58) Field of Classification Search
CPC ............ A63B 71/0622; A63B 2220/52; A63B 2230/207; A63B 2230/06; A63B 2230/01; A63B 2230/00; A63B 2225/50; A63B 2225/20; A63B 2220/806; A63B 2220/75; A63B 2220/74; A63B 21/00047; A63B 2220/73; A63B 2220/72; A63B 2220/70; A63B 2220/62; A63B 23/03558; A63B 2220/56; A63B 2220/31; A63B 2220/17; A63B 2220/13; A63B 2220/10; A63B 2220/05; A63B 2071/0658; A63B 2071/065; A63B 2071/063; A63B 2023/006; A63B 2230/40; A63B 23/1218; A63B 23/03541; A63B 23/03525; A63B 23/0216; A63B 2230/30; A63B 22/0023; A63B 21/1636; A63B 21/1627; A63B 21/1618; A63B 21/16; A63B 21/0726; A63B 17/04; A63B 23/1227; A63B 23/1236; A63B 2230/75; A63B 1/00; G06F 19/3481

See application file for complete search history.

(56) References Cited

U.S. PATENT DOCUMENTS

| | | |
|---|---|---|
| 34,577 A | 3/1862 | Jabden |
| 104,973 A | 7/1870 | Man |
| 115,826 A | 6/1871 | Creed |
| 192,338 A | 6/1877 | Marshall |
| 232,022 A | 9/1880 | Gifford |
| 232,579 A | 9/1880 | Weeks |
| 248,121 A | 10/1881 | Tuttle |
| 321,388 A | 6/1885 | Ruebsam |
| 325,435 A | 9/1885 | North |
| 337,942 A | 3/1886 | Parley |
| 353,089 A | 11/1886 | Smith |
| 356,219 A | 1/1887 | Yeoman |
| 359,778 A | 3/1887 | Pauber |
| 372,272 A | 10/1887 | Murphy |
| 374,496 A | 12/1887 | Reach |
| 428,912 A | 5/1890 | Holmes |
| 457,400 A | 8/1891 | Dowd |
| 480,271 A | 8/1892 | Newton |
| 484,352 A | 10/1892 | Ayton |
| 588,350 A | 8/1897 | Perkins |
| 603,350 A | 5/1898 | Towers |
| 610,716 A | 9/1898 | Marshal |
| 624,995 A | 5/1899 | Tellefsen |
| 679,784 A | 8/1901 | Ryan |
| 680,556 A | 8/1901 | Wray |
| 682,988 A | 9/1901 | Carroll |
| 685,788 A | 11/1901 | Mcfadden |
| 689,418 A | 12/1901 | Ryan |
| 722,462 A | 3/1903 | Smith |
| 723,625 A | 3/1903 | Thornley |
| 754,992 A | 3/1904 | Grabner |
| 760,374 A | 5/1904 | Belvoir |
| 761,504 A | 5/1904 | Kleinbach |
| 772,906 A | 10/1904 | Reach |
| 776,824 A | 12/1904 | Bryon, Jr. |
| 807,670 A | 12/1905 | Grabner |
| 846,389 A | 3/1907 | Blackburn |
| 852,193 A | 4/1907 | Mcmillan |
| 943,127 A | 12/1909 | Van Boven |
| 424,745 A | 7/1910 | Blakoe |
| 979,609 A | 12/1910 | Vaughn |
| 1,019,861 A | 3/1912 | Titus |
| 1,082,940 A | 12/1913 | Sharp |
| 1,115,826 A | 11/1914 | Johnson |
| 1,123,272 A | 1/1915 | Goodman |
| 1,144,085 A | 6/1915 | Abplanalp |
| 1,316,683 A | 9/1919 | Calvert |
| 1,422,888 A | 7/1922 | Reeves |
| 1,495,278 A | 5/1924 | Titus |
| 1,539,214 A | 5/1925 | Shockey |
| 1,576,474 A | 3/1926 | Walker |
| 1,585,748 A | 5/1926 | Wendelken |
| 1,672,944 A | 6/1928 | Jowett |
| 1,698,831 A | 1/1929 | Weimar |
| 1,851,843 A | 3/1932 | Inman |
| 1,917,566 A | 7/1933 | Robert |
| 1,919,627 A | 7/1933 | Fitz Gerald |
| 1,928,089 A | 9/1933 | Blickman |
| 1,982,843 A | 12/1934 | Traver |
| 1,982,872 A | 12/1934 | Newton |
| 1,991,520 A | 2/1935 | Postl |

(56) References Cited

U.S. PATENT DOCUMENTS

| | | |
|---|---|---|
| 2,017,885 A | 10/1935 | Atcheson |
| 2,129,262 A | 9/1938 | Rex |
| 2,145,940 A | 2/1939 | Marlowe |
| 2,153,077 A | 4/1939 | Frederick |
| 2,155,684 A | 4/1939 | Richards |
| 2,183,345 A | 12/1939 | Brandon |
| 2,209,034 A | 7/1940 | Rene |
| 2,219,219 A | 10/1940 | Boger |
| 2,274,574 A | 2/1942 | Zerne |
| 2,315,485 A | 4/1943 | Le Roy |
| 2,346,105 A | 4/1944 | Haehnel |
| 2,379,984 A | 7/1945 | Nereaux |
| 2,436,987 A | 3/1948 | Bailleaux |
| 2,438,548 A | 3/1948 | Ehmann |
| 2,456,017 A | 12/1948 | Park |
| 2,470,544 A | 5/1949 | Bell |
| 2,472,391 A | 6/1949 | Albizu |
| 2,500,299 A | 3/1950 | Spitzkeit |
| 2,512,417 A | 6/1950 | Polite |
| 2,573,351 A | 10/1951 | Motis |
| 2,632,645 A | 3/1953 | Barkschat |
| 2,637,319 A | 5/1953 | Bruene |
| 2,640,696 A | 6/1953 | Adalbert |
| 2,641,250 A | 6/1953 | Brockman |
| 2,642,288 A | 6/1953 | Bell |
| 2,646,282 A | 7/1953 | Ringman |
| 2,648,540 A | 8/1953 | Hunter |
| 2,654,135 A | 10/1953 | Grizzard et al. |
| 2,695,797 A | 11/1954 | Mccarthy et al. |
| 2,714,507 A | 8/1955 | Goodrich |
| 2,740,178 A | 4/1956 | Kellems |
| 2,763,156 A | 9/1956 | Garigal |
| 2,843,858 A | 7/1958 | Bjorklund |
| 2,855,200 A | 10/1958 | Harry |
| 2,924,456 A | 2/1960 | Miller |
| 2,927,006 A | 3/1960 | Brooks |
| 2,938,695 A | 5/1960 | Ciampa |
| 2,968,337 A | 1/1961 | Bartlett |
| 2,969,060 A | 1/1961 | Swanda |
| 2,977,120 A | 3/1961 | Morris |
| 2,978,830 A | 4/1961 | Killian |
| 2,985,933 A | 5/1961 | Peterson et al. |
| 3,000,628 A | 9/1961 | Kellogg |
| 3,057,201 A | 10/1962 | Jaeger |
| 3,068,002 A | 12/1962 | Balne |
| 3,090,092 A | 5/1963 | Szemplak |
| 3,099,509 A | 7/1963 | Duenke |
| 3,115,332 A | 12/1963 | Singleton |
| 3,118,441 A | 1/1964 | George |
| 3,123,646 A | 3/1964 | Easton |
| 3,161,395 A | 12/1964 | Carter |
| 3,193,287 A | 7/1965 | Robinson |
| 3,194,598 A | 7/1965 | Goldfuss |
| 3,205,888 A | 9/1965 | Stroop |
| 3,246,894 A | 4/1966 | Salisbury |
| 3,256,630 A | 6/1966 | Spector |
| 3,270,494 A | 9/1966 | Holmes |
| 3,312,466 A | 4/1967 | Melchiona |
| 3,323,367 A | 6/1967 | Searle |
| 3,342,485 A | 9/1967 | Gaul |
| 3,345,067 A | 10/1967 | Smith |
| 3,349,621 A | 10/1967 | Mullen |
| 3,370,584 A | 2/1968 | Girten |
| 3,373,993 A | 3/1968 | Oja et al. |
| 3,380,737 A | 4/1968 | Elia |
| 3,381,958 A | 5/1968 | Gulland |
| 3,384,370 A | 5/1968 | Bailey et al. |
| 3,390,460 A | 7/1968 | Brown |
| 3,411,776 A | 11/1968 | Holkesvick et al. |
| 3,428,311 A | 2/1969 | Mitchell |
| 3,428,312 A | 2/1969 | Machen |
| 3,432,164 A | 3/1969 | Deeks |
| 3,438,627 A | 4/1969 | La Lanne |
| 3,446,503 A | 5/1969 | Lawton |
| 3,456,592 A | 7/1969 | Nelsen |
| 3,465,592 A | 9/1969 | Perrine |
| 3,482,835 A | 12/1969 | Dean |
| 3,488,051 A | 1/1970 | Papistas Scherer |
| 3,495,824 A | 2/1970 | Cuinier |
| 3,501,140 A | 3/1970 | Eichorn |
| 3,511,500 A | 5/1970 | Dunn |
| 3,540,724 A | 11/1970 | Hunter |
| 3,563,541 A | 2/1971 | Sanquist |
| 3,566,861 A | 3/1971 | Weiss |
| 3,567,219 A | 3/1971 | Foster |
| 3,572,700 A | 3/1971 | Mastropaolo |
| 3,579,339 A | 5/1971 | Chang |
| 3,588,101 A | 6/1971 | Jungreis |
| 3,589,193 A | 6/1971 | Thornton |
| 3,589,720 A | 6/1971 | Agamian |
| 3,598,404 A | 8/1971 | Bowman |
| 3,601,398 A | 8/1971 | Brochman |
| 3,606,406 A | 9/1971 | Walters |
| 3,614,097 A | 10/1971 | Blickman |
| 3,614,108 A | 10/1971 | Garten |
| 3,617,056 A | 11/1971 | Herbold |
| 3,638,941 A | 2/1972 | Kulkens |
| 3,640,528 A | 2/1972 | Proctor |
| 3,640,530 A | 2/1972 | Henson et al. |
| 3,643,943 A | 2/1972 | Erwin, Jr. et al. |
| 3,647,209 A | 3/1972 | La Lanne |
| 3,652,085 A | 3/1972 | Cole |
| 3,658,327 A | 4/1972 | Thiede |
| 3,659,845 A | 5/1972 | Quinton |
| 3,664,910 A | 5/1972 | Hollie |
| 3,664,916 A | 5/1972 | Rhodiaceta |
| 3,672,124 A | 6/1972 | Pirotta |
| 3,679,244 A | 7/1972 | Reddy |
| 3,690,655 A | 9/1972 | Chapman |
| 3,708,166 A | 1/1973 | Annas |
| 3,708,167 A | 1/1973 | Potgieter |
| 3,758,109 A | 9/1973 | Bender |
| 3,759,511 A | 9/1973 | Zinkin |
| 3,761,083 A | 9/1973 | Buchner |
| 3,767,195 A | 10/1973 | Dimick |
| 3,771,785 A | 11/1973 | Speyer |
| 3,784,193 A | 1/1974 | Simjian |
| 3,789,467 A | 2/1974 | Aratani et al. |
| 3,792,860 A | 2/1974 | Selnes |
| 3,797,624 A | 3/1974 | Powell et al. |
| 3,802,701 A | 4/1974 | Good |
| 3,807,728 A | 4/1974 | Chillier |
| 3,809,393 A | 5/1974 | Jones |
| 3,814,420 A | 6/1974 | Encke |
| 3,815,903 A | 6/1974 | Blomqvist |
| 3,822,599 A | 7/1974 | Brentham |
| 3,825,253 A | 7/1974 | Speyer |
| 3,831,942 A | 8/1974 | Del Mar |
| 3,833,216 A | 9/1974 | Philbin |
| 3,834,696 A | 9/1974 | Spector |
| 3,840,227 A | 10/1974 | Chesemore |
| 3,848,467 A | 11/1974 | Flavell |
| 3,851,874 A | 12/1974 | Wilkin |
| 3,858,873 A | 1/1975 | Jones |
| 3,858,874 A | 1/1975 | Weider |
| 3,870,297 A | 3/1975 | Elder |
| 3,874,375 A | 4/1975 | Penner |
| 3,874,657 A | 4/1975 | Niebojewski |
| 3,884,464 A | 5/1975 | Evangelos |
| 3,891,207 A | 6/1975 | Helliwell |
| 3,892,404 A | 7/1975 | Martucci |
| 3,902,480 A | 9/1975 | Wilson |
| 3,902,717 A | 9/1975 | Kulkens |
| 3,913,908 A | 10/1975 | Speyer |
| 3,918,710 A | 11/1975 | Niebojewski |
| 3,920,240 A | 11/1975 | Ross |
| 3,926,430 A | 12/1975 | Good |
| 3,938,803 A | 2/1976 | Wilmoth |
| 3,953,025 A | 4/1976 | Mazman |
| 3,957,266 A | 5/1976 | Rice |
| 3,958,803 A | 5/1976 | Geisselbrecht |
| 3,971,555 A | 7/1976 | Mahnke |
| 3,976,058 A | 8/1976 | Tidwell |
| 3,979,931 A | 9/1976 | Man |

(56) References Cited

U.S. PATENT DOCUMENTS

| | | |
|---|---|---|
| 3,981,500 A | 9/1976 | Ryan |
| 3,984,666 A | 10/1976 | Barron |
| 3,998,454 A | 12/1976 | Jones |
| 4,004,801 A | 1/1977 | Campanaro |
| 4,023,795 A | 5/1977 | Pauls |
| 4,026,545 A | 5/1977 | Schonenberger |
| 4,026,548 A | 5/1977 | Birdwell |
| 4,029,312 A | 6/1977 | Wright |
| 4,042,305 A | 8/1977 | Vincent |
| 4,043,552 A | 8/1977 | Kerkonian |
| 4,059,265 A | 11/1977 | Wieder et al. |
| 4,060,240 A | 11/1977 | Dunston |
| 4,061,257 A | 12/1977 | St. Clair |
| 4,063,727 A | 12/1977 | Hall |
| 4,066,868 A | 1/1978 | Witkin et al. |
| 4,071,235 A | 1/1978 | Zent |
| 4,072,309 A | 2/1978 | Wilson |
| 4,073,490 A | 2/1978 | Feather |
| 4,074,409 A | 2/1978 | Smith |
| 4,074,519 A | 2/1978 | Garrett |
| 4,076,236 A | 2/1978 | Ionel |
| 4,076,237 A | 2/1978 | Dussia |
| 4,082,267 A | 4/1978 | Flavell |
| 4,093,211 A | 6/1978 | Hughes et al. |
| 4,098,100 A | 7/1978 | Wah |
| 4,101,124 A | 7/1978 | Mahnke |
| 4,122,585 A | 10/1978 | Sharp et al. |
| 4,131,701 A | 12/1978 | VanAuken |
| 4,140,312 A | 2/1979 | Buchmann |
| 4,154,441 A | 5/1979 | Gajda |
| 4,157,181 A | 6/1979 | Cecka |
| 4,157,594 A | 6/1979 | Raabe |
| 4,170,351 A | 10/1979 | Ozbey |
| 4,171,805 A | 10/1979 | Abbott |
| 4,176,836 A | 12/1979 | Coyle |
| 4,188,030 A | 2/1980 | Hooper |
| 4,193,630 A | 3/1980 | Steele |
| 4,198,044 A | 4/1980 | Holappa |
| 4,199,139 A | 4/1980 | Mahnke |
| 4,200,279 A | 4/1980 | Lambert, Jr. |
| 4,200,280 A | 4/1980 | Goodwin |
| 4,204,673 A | 5/1980 | Speer, Sr. |
| 4,207,879 A | 6/1980 | Safadago |
| 4,208,049 A | 6/1980 | Wilson |
| 4,227,689 A | 10/1980 | Keiser |
| 4,231,568 A | 11/1980 | Riley |
| 4,231,569 A | 11/1980 | Rae |
| 4,235,437 A | 11/1980 | Ruis et al. |
| 4,239,092 A | 12/1980 | Janson |
| 4,241,915 A | 12/1980 | Noble |
| 4,249,773 A | 2/1981 | Giambalvo |
| 4,252,314 A | 2/1981 | Ceppo |
| 4,253,662 A | 3/1981 | Podolak |
| 4,256,302 A | 3/1981 | Keiser et al. |
| 4,257,590 A | 3/1981 | Sullivan et al. |
| 4,258,913 A | 3/1981 | Brentham |
| 4,263,897 A | 4/1981 | Terayama |
| 4,274,625 A | 6/1981 | Gaetano |
| 4,275,882 A | 6/1981 | Grosser et al. |
| 4,278,249 A | 7/1981 | Forrest |
| 4,286,782 A | 9/1981 | Fuhrhop |
| 4,296,924 A | 10/1981 | Anzaldua et al. |
| 4,300,760 A | 11/1981 | Bobroff |
| 4,300,761 A | 11/1981 | Howard |
| 4,307,880 A | 12/1981 | Abram |
| 4,316,609 A | 2/1982 | Silberman |
| 4,316,610 A | 2/1982 | Hinds |
| 4,325,548 A | 4/1982 | Piccini |
| 4,327,713 A | 5/1982 | Okazaki et al. |
| 4,328,964 A | 5/1982 | Walls |
| 4,328,965 A | 5/1982 | Hatfield |
| 4,328,968 A | 5/1982 | Hacker |
| 4,334,678 A | 6/1982 | Doyel |
| 4,345,756 A | 8/1982 | Hoagland |
| 4,346,888 A | 8/1982 | Szabo |
| 4,349,192 A | 9/1982 | Lambert, Jr. et al. |
| 4,354,675 A | 10/1982 | Barclay et al. |
| 4,355,061 A | 10/1982 | Zeigler |
| 4,357,010 A | 11/1982 | Telle |
| 4,357,011 A | 11/1982 | Voris |
| 4,368,735 A | 1/1983 | Filmer |
| 4,369,966 A | 1/1983 | Silberman et al. |
| 4,371,162 A | 2/1983 | Hartzell |
| 4,372,553 A | 2/1983 | Hatfield |
| 4,373,716 A | 2/1983 | Pagani |
| 4,374,588 A | 2/1983 | Ruggles |
| 4,376,533 A | 3/1983 | Kolbel |
| 4,382,596 A | 5/1983 | Silberman |
| 4,383,684 A | 5/1983 | Schliep |
| 4,384,715 A | 5/1983 | Barrett, Jr. |
| 4,387,893 A | 6/1983 | Baldwin |
| 4,389,047 A | 6/1983 | Hall |
| 4,390,179 A | 6/1983 | Szkalak |
| 4,391,440 A | 7/1983 | Berger |
| 4,397,462 A | 8/1983 | Wilmarth |
| 4,398,713 A | 8/1983 | Ellis |
| 4,402,504 A | 9/1983 | Christian |
| 4,413,821 A | 11/1983 | Centafanti |
| 4,422,636 A | 12/1983 | de Angeli |
| 4,424,693 A | 1/1984 | Best et al. |
| 4,426,077 A | 1/1984 | Becker |
| 4,428,577 A | 1/1984 | Weingardt |
| 4,428,578 A | 1/1984 | Kirkpatrick |
| 4,431,181 A | 2/1984 | Baswell |
| 4,431,184 A | 2/1984 | Lew et al. |
| 4,441,708 A | 4/1984 | Brentham |
| 4,448,434 A | 5/1984 | Anderson |
| 4,452,448 A | 6/1984 | Ausherman |
| 4,456,245 A | 6/1984 | Baldwin |
| 4,456,246 A | 6/1984 | Szabo |
| 4,461,473 A | 7/1984 | Cole |
| 4,463,948 A | 8/1984 | Mohr |
| 4,465,274 A | 8/1984 | Davenport |
| 4,465,276 A | 8/1984 | Cox |
| 4,474,370 A | 10/1984 | Oman |
| 4,477,071 A | 10/1984 | Brown et al. |
| 4,478,413 A | 10/1984 | Siwula |
| 4,482,152 A | 11/1984 | Wolff |
| 4,489,933 A | 12/1984 | Fisher |
| 4,489,936 A | 12/1984 | Dal Monte |
| 4,492,375 A | 1/1985 | Connelly |
| 4,494,662 A | 1/1985 | Clymer |
| 4,502,679 A | 3/1985 | De Lorenzo |
| 4,502,682 A | 3/1985 | Miller |
| 4,505,475 A | 3/1985 | Olschansky et al. |
| 4,505,495 A | 3/1985 | Foss et al. |
| 4,511,137 A | 4/1985 | Jones |
| 4,512,571 A | 4/1985 | Hermelin |
| 4,515,363 A | 5/1985 | Schleffendorf |
| 4,521,013 A | 6/1985 | Dofel |
| 4,529,194 A | 7/1985 | Haaheim |
| 4,529,196 A | 7/1985 | Logan |
| 4,529,197 A | 7/1985 | Gogarty |
| 4,529,198 A | 7/1985 | Hettick, Jr. |
| 4,531,727 A | 7/1985 | Pitre |
| 4,531,731 A | 7/1985 | Law |
| 4,533,136 A | 8/1985 | Smith et al. |
| 4,537,396 A | 8/1985 | Hooper |
| 4,538,805 A | 9/1985 | Parviainen |
| 4,540,171 A | 9/1985 | Clark |
| 4,540,173 A | 9/1985 | Hopkins, Jr. |
| 4,542,899 A | 9/1985 | Hendricks |
| 4,546,967 A | 10/1985 | Kecala |
| 4,546,970 A | 10/1985 | Mahnke |
| 4,546,971 A | 10/1985 | Raasoch |
| 4,549,433 A | 10/1985 | Gneiss et al. |
| 4,549,733 A | 10/1985 | Salyer |
| 4,549,734 A | 10/1985 | Hibler, Jr. |
| 4,555,109 A | 11/1985 | Hartmann |
| 4,556,216 A | 12/1985 | Pitkanen |
| 4,563,001 A | 1/1986 | Terauds |
| 4,563,003 A | 1/1986 | Bugallo et al. |
| 4,564,193 A | 1/1986 | Stewart |
| 4,565,369 A | 1/1986 | Bedgood |

(56) References Cited

U.S. PATENT DOCUMENTS

| | | |
|---|---|---|
| 4,566,689 A | 1/1986 | Ogden |
| 4,566,690 A | 1/1986 | Schook |
| 4,569,518 A | 2/1986 | Fulks |
| 4,569,519 A | 2/1986 | Mattox et al. |
| 4,575,074 A | 3/1986 | Damratoski |
| 4,576,377 A | 3/1986 | Wolff |
| 4,577,861 A | 3/1986 | Bangerter et al. |
| 4,579,360 A | 4/1986 | Nishimura et al. |
| 4,582,320 A | 4/1986 | Shaw |
| 4,587,695 A | 5/1986 | Jensen |
| 4,591,150 A | 5/1986 | Mosher |
| 4,591,151 A | 5/1986 | Hensley |
| 4,592,544 A | 6/1986 | Smith et al. |
| 4,598,908 A | 7/1986 | Morgan |
| 4,600,188 A | 7/1986 | Bangerter et al. |
| 4,600,189 A | 7/1986 | Olschansky et al. |
| 4,600,196 A | 7/1986 | Jones |
| 4,603,855 A | 8/1986 | Sebelle |
| 4,603,856 A | 8/1986 | Fiore |
| 4,606,540 A | 8/1986 | Chin Sen |
| 4,606,541 A | 8/1986 | Kirkpatrick |
| 4,607,840 A | 8/1986 | Harper |
| 4,607,841 A | 8/1986 | Gala |
| 4,608,969 A | 9/1986 | Hamlin |
| 4,609,174 A | 9/1986 | Nakatani |
| 4,610,448 A | 9/1986 | Hill |
| 4,610,449 A | 9/1986 | Diercks, Jr. |
| 4,611,805 A | 9/1986 | Franklin et al. |
| D286,311 S | 10/1986 | Martinell |
| 4,618,139 A | 10/1986 | Haaheim |
| 4,618,140 A | 10/1986 | Brown |
| 4,618,144 A | 10/1986 | Gibson |
| 4,620,701 A | 11/1986 | Mojden |
| 4,620,704 A | 11/1986 | Shifferaw |
| 4,621,623 A | 11/1986 | Wang |
| 4,621,807 A | 11/1986 | Stramer |
| 4,621,810 A | 11/1986 | Cummins |
| 4,624,457 A | 11/1986 | Silberman et al. |
| 4,625,962 A | 12/1986 | Street |
| 4,627,614 A | 12/1986 | Angeli |
| 4,627,615 A | 12/1986 | Nurkowski |
| 4,627,616 A | 12/1986 | Kauffman |
| 4,627,618 A | 12/1986 | Schwartz |
| 4,632,385 A | 12/1986 | Geraci |
| 4,632,388 A | 12/1986 | Schleffendorf |
| 4,632,390 A | 12/1986 | Richey |
| 4,632,393 A | 12/1986 | Van Noord |
| 4,632,414 A | 12/1986 | Ellefson |
| 4,632,421 A | 12/1986 | Shamie |
| 4,634,118 A | 1/1987 | Jensen |
| 4,634,127 A | 1/1987 | Rockwell |
| 4,635,926 A | 1/1987 | Minkow |
| 4,638,994 A | 1/1987 | Gogarty |
| 4,641,833 A | 2/1987 | Trethewey |
| 4,643,420 A | 2/1987 | Riley |
| 4,645,198 A | 2/1987 | Levenston |
| 4,647,037 A | 3/1987 | Donohue |
| 4,647,040 A | 3/1987 | Ehrenfried |
| 4,648,481 A | 3/1987 | Lee |
| 4,648,594 A | 3/1987 | Schleffendorf |
| 4,650,183 A | 3/1987 | McIntyre |
| 4,650,185 A | 3/1987 | Cartwright |
| 4,651,988 A | 3/1987 | Sobel |
| 4,655,448 A | 4/1987 | Harder |
| 4,657,246 A | 4/1987 | Salyer |
| 4,659,077 A | 4/1987 | Stropkay |
| 4,660,550 A | 4/1987 | Bodine |
| 4,662,629 A | 5/1987 | Plovie |
| 4,666,149 A | 5/1987 | Olschansky et al. |
| 4,666,151 A | 5/1987 | Chillier |
| 4,673,180 A | 6/1987 | Rice |
| 4,678,185 A | 7/1987 | Mahnke |
| 4,679,786 A | 7/1987 | Rodgers |
| 4,679,787 A | 7/1987 | Guilbault |
| 4,681,318 A | 7/1987 | Lay |
| 4,684,126 A | 8/1987 | Dalebout et al. |
| 4,685,670 A | 8/1987 | Zinkin |
| 4,685,671 A | 8/1987 | Hagerman et al. |
| 4,697,809 A | 10/1987 | Rockwell |
| 4,700,946 A | 10/1987 | Breunig |
| 4,705,028 A | 11/1987 | Melby |
| 4,705,267 A | 11/1987 | Jackson |
| 4,706,953 A | 11/1987 | Graham |
| 4,709,920 A | 12/1987 | Schnell |
| 4,717,146 A | 1/1988 | Nohara |
| 4,720,099 A | 1/1988 | Carlson |
| 4,721,301 A | 1/1988 | Drake |
| 4,721,303 A | 1/1988 | Fitzpatrick |
| 4,722,522 A | 2/1988 | Lundgren |
| 4,725,057 A | 2/1988 | Shifferaw |
| 4,726,581 A | 2/1988 | Chang |
| 4,726,582 A | 2/1988 | Fulks |
| 4,728,099 A | 3/1988 | Pitre |
| 4,728,102 A | 3/1988 | Pauls |
| 4,729,558 A | 3/1988 | Kuo |
| 4,729,562 A | 3/1988 | Pipasik |
| 4,730,828 A | 3/1988 | Lane |
| 4,730,829 A | 3/1988 | Carlson |
| 4,733,860 A | 3/1988 | Steffee |
| 4,733,905 A | 3/1988 | Buickerood |
| 4,741,530 A | 5/1988 | Wolf |
| 4,743,010 A | 5/1988 | Geraci |
| 4,743,015 A | 5/1988 | Marshall |
| 4,743,017 A | 5/1988 | Jaeger |
| 4,744,559 A | 5/1988 | Mahnke et al. |
| 4,746,115 A | 5/1988 | Lahman |
| 4,750,736 A | 6/1988 | Watterson |
| 4,750,738 A | 6/1988 | Dang |
| 4,753,437 A | 6/1988 | Lapcevic |
| 4,756,527 A | 7/1988 | Ledbetter |
| 4,763,897 A | 8/1988 | Yakata |
| 4,765,610 A | 8/1988 | Sidwell |
| 4,765,613 A | 8/1988 | Voris |
| 4,765,616 A | 8/1988 | Wolff |
| 4,768,780 A | 9/1988 | Hayes |
| 4,772,015 A | 9/1988 | Carlson et al. |
| 4,773,640 A | 9/1988 | Kolbel et al. |
| 4,775,149 A | 10/1988 | Wilson |
| 4,776,581 A | 10/1988 | Shepherdson |
| 4,776,587 A | 10/1988 | Carlson et al. |
| 4,778,173 A | 10/1988 | Joutras |
| 4,779,867 A | 10/1988 | Hinds |
| 4,784,384 A | 11/1988 | Deola |
| 4,786,050 A | 11/1988 | Geschwender |
| 4,789,153 A | 12/1988 | Brown |
| 4,790,522 A | 12/1988 | Drutchas |
| 4,790,596 A | 12/1988 | Shifferaw |
| 4,793,608 A | 12/1988 | Mahnke et al. |
| 4,796,881 A | 1/1989 | Watterson |
| 4,798,377 A | 1/1989 | White |
| 4,799,671 A | 1/1989 | Hoggan et al. |
| 4,801,139 A | 1/1989 | Vanhoutte |
| 4,801,140 A | 1/1989 | Bergeron |
| 4,804,178 A | 2/1989 | Friedebach |
| 4,807,874 A | 2/1989 | Little |
| 4,807,893 A | 2/1989 | Huang |
| 4,809,972 A | 3/1989 | Rasmussen et al. |
| 4,809,973 A | 3/1989 | Johns |
| 4,809,976 A | 3/1989 | Berger |
| 4,813,667 A | 3/1989 | Watterson |
| 4,822,034 A | 4/1989 | Shields |
| 4,822,035 A | 4/1989 | Jennings et al. |
| 4,822,038 A | 4/1989 | Maag |
| 4,826,153 A | 5/1989 | Schalip |
| 4,826,157 A | 5/1989 | Fitzpatrick |
| 4,826,158 A | 5/1989 | Fields, Jr. |
| 4,830,363 A | 5/1989 | Kennedy |
| 4,830,365 A | 5/1989 | March |
| 4,830,371 A | 5/1989 | Lay |
| 4,832,332 A | 5/1989 | Dumbser |
| 4,834,365 A | 5/1989 | Jones |
| 4,834,396 A | 5/1989 | Schnell |
| 4,836,535 A | 6/1989 | Pearson |
| 4,838,180 A | 6/1989 | Gutgsell |

(56) References Cited

U.S. PATENT DOCUMENTS

| | | |
|---|---|---|
| 4,838,543 A | 6/1989 | Armstrong et al. |
| 4,838,544 A | 6/1989 | Sasakawa et al. |
| 4,840,373 A | 6/1989 | Maag |
| 4,842,268 A | 6/1989 | Jenkins |
| 4,842,274 A | 6/1989 | Oosthuizen |
| 4,844,448 A | 7/1989 | Niznik |
| 4,844,450 A | 7/1989 | Rodgers, Jr. |
| 4,844,451 A | 7/1989 | Bersonnet |
| 4,844,453 A | 7/1989 | Hestilow |
| 4,844,456 A | 7/1989 | Habing et al. |
| 4,846,458 A | 7/1989 | Potts |
| 4,848,737 A | 7/1989 | Ehrenfield |
| 4,850,585 A | 7/1989 | Dalebout |
| 4,852,874 A | 8/1989 | Sleichter, III et al. |
| 4,854,578 A | 8/1989 | Fulks |
| 4,856,773 A | 8/1989 | Deola |
| 4,856,775 A | 8/1989 | Colledge |
| 4,858,912 A | 8/1989 | Boyd |
| 4,858,915 A | 8/1989 | Szabo |
| 4,858,918 A | 8/1989 | Iams et al. |
| 4,861,020 A | 8/1989 | Soligny, Sr. |
| 4,861,023 A | 8/1989 | Wedman |
| 4,861,025 A | 8/1989 | Rockwell |
| 4,863,161 A | 9/1989 | Telle |
| 4,863,163 A | 9/1989 | Wehrell |
| 4,869,493 A | 9/1989 | Johnston |
| 4,872,670 A | 10/1989 | Nichols |
| 4,877,239 A | 10/1989 | Dela Rosa |
| D304,849 S | 11/1989 | Watterson |
| 4,878,662 A | 11/1989 | Chern |
| 4,880,225 A | 11/1989 | Lucas |
| 4,880,227 A | 11/1989 | Sowell |
| 4,880,229 A | 11/1989 | Broussard |
| 4,880,230 A | 11/1989 | Cook |
| 4,883,272 A | 11/1989 | Lay |
| 4,887,929 A | 12/1989 | Hale |
| 4,889,458 A | 12/1989 | Taylor |
| 4,893,409 A | 1/1990 | Poehlmann |
| 4,893,810 A | 1/1990 | Lee |
| 4,898,381 A | 2/1990 | Gordon |
| 4,900,013 A | 2/1990 | Rodgers, Jr. |
| 4,900,016 A | 2/1990 | Caruthers |
| 4,900,018 A | 2/1990 | Ish, III |
| 4,902,006 A | 2/1990 | Stallings, Jr. |
| 4,902,007 A | 2/1990 | Ferrari |
| D306,468 S | 3/1990 | Watterson |
| D306,891 S | 3/1990 | Watterson |
| 4,907,795 A | 3/1990 | Shaw et al. |
| 4,907,797 A | 3/1990 | Gezari et al. |
| 4,907,798 A | 3/1990 | Burchatz |
| 4,909,505 A | 3/1990 | Tee |
| 4,911,436 A | 3/1990 | Lighter |
| 4,911,438 A | 3/1990 | Van Straaten |
| 4,913,396 A | 4/1990 | Dalebout et al. |
| 4,913,419 A | 4/1990 | McAuliffe |
| 4,913,422 A | 4/1990 | Elmore |
| 4,913,423 A | 4/1990 | Farran |
| 4,915,377 A | 4/1990 | Malnke et al. |
| 4,915,379 A | 4/1990 | Sapp |
| 4,919,419 A | 4/1990 | Houston |
| D307,614 S | 5/1990 | Bingham |
| D307,615 S | 5/1990 | Bingham |
| 4,921,242 A | 5/1990 | Watterson |
| 4,921,245 A | 5/1990 | Roberts |
| 4,925,200 A | 5/1990 | Jones |
| 4,927,136 A | 5/1990 | Leask |
| 4,927,138 A | 5/1990 | Ferrari |
| 4,928,961 A | 5/1990 | Madden |
| 4,930,768 A | 6/1990 | Lapcevic |
| 4,930,769 A | 6/1990 | Nenoff |
| 4,930,770 A | 6/1990 | Baker |
| 4,932,650 A | 6/1990 | Bingham |
| 4,934,690 A | 6/1990 | Bull |
| 4,934,692 A | 6/1990 | Owens |
| D309,167 S | 7/1990 | Griffin |
| D309,485 S | 7/1990 | Bingham |
| 4,938,478 A | 7/1990 | Lay |
| 4,940,233 A | 7/1990 | Bull |
| 4,944,511 A | 7/1990 | Francis |
| 4,944,518 A | 7/1990 | Flynn |
| D310,253 S | 8/1990 | Bersonnet |
| 4,948,121 A | 8/1990 | Haaheim et al. |
| 4,948,123 A | 8/1990 | Schook |
| 4,949,951 A | 8/1990 | Deola |
| 4,949,954 A | 8/1990 | Hix |
| 4,949,958 A | 8/1990 | Richey |
| 4,949,959 A | 8/1990 | Stevens |
| 4,955,599 A | 9/1990 | Bersonnet |
| 4,958,832 A | 9/1990 | Kim |
| 4,964,632 A | 10/1990 | Rockwell |
| 4,971,305 A | 11/1990 | Rennex |
| 4,971,316 A | 11/1990 | Dalebout et al. |
| 4,973,050 A | 11/1990 | Santoro |
| D313,055 S | 12/1990 | Watterson |
| 4,974,832 A | 12/1990 | Dalebout |
| 4,974,836 A | 12/1990 | Hirsch |
| 4,974,838 A | 12/1990 | Sollenberger |
| 4,976,428 A | 12/1990 | Ghazi |
| 4,978,122 A | 12/1990 | Dibowski |
| 4,979,737 A | 12/1990 | Kock |
| 4,981,294 A | 1/1991 | Dalebout |
| 4,982,955 A | 1/1991 | Heasley |
| 4,986,689 A | 1/1991 | Drutchas |
| 4,989,860 A | 2/1991 | Iams et al. |
| 4,990,838 A | 2/1991 | Kawato et al. |
| 4,992,190 A | 2/1991 | Shtarkman |
| 4,995,777 A | 2/1991 | Warmington |
| D315,765 S | 3/1991 | Measom |
| 4,998,723 A | 3/1991 | Santoro |
| 4,998,725 A | 3/1991 | Watterson |
| 5,000,440 A | 3/1991 | Lynch |
| 5,000,442 A | 3/1991 | Dalebout et al. |
| 5,000,443 A | 3/1991 | Dalebout |
| 5,000,444 A | 3/1991 | Dalebout |
| 5,000,446 A | 3/1991 | Sarno |
| D316,124 S | 4/1991 | Dalebout |
| 5,004,224 A | 4/1991 | Wang |
| 5,005,832 A | 4/1991 | Van Der Hoeven |
| 5,011,139 A | 4/1991 | Towley, III |
| 5,011,142 A | 4/1991 | Eckler |
| 5,013,033 A | 5/1991 | Watterson |
| 5,014,980 A | 5/1991 | Bersonnet |
| 5,015,926 A | 5/1991 | Casler |
| 5,016,871 A | 5/1991 | Dalebout |
| 5,018,725 A | 5/1991 | Cook |
| 5,022,377 A | 6/1991 | Stevens |
| 5,026,049 A | 6/1991 | Goodman |
| D318,085 S | 7/1991 | Jacobson |
| D318,086 S | 7/1991 | Bingham |
| D318,699 S | 7/1991 | Jacobson |
| 5,029,801 A | 7/1991 | Dalebout |
| 5,029,848 A | 7/1991 | Sleamaker |
| 5,029,849 A | 7/1991 | Nurkowski |
| 5,029,850 A | 7/1991 | Van Straaten |
| 5,031,905 A | 7/1991 | Walsh |
| 5,032,048 A | 7/1991 | Walton et al. |
| 5,033,740 A | 7/1991 | Schwartz |
| 5,034,576 A | 7/1991 | Dalebout |
| 5,037,090 A | 8/1991 | Fitzpatrick |
| 5,039,088 A | 8/1991 | Shifferaw |
| 5,039,089 A | 8/1991 | Lapcevic |
| 5,039,091 A | 8/1991 | Johnson |
| 5,040,785 A | 8/1991 | Charnitski |
| 5,040,787 A | 8/1991 | Brotman |
| 5,040,788 A | 8/1991 | Randall |
| 5,042,704 A | 8/1991 | Izzo |
| 5,042,799 A | 8/1991 | Stanley |
| 5,044,629 A | 9/1991 | Ryan |
| 5,044,631 A | 9/1991 | Jones |
| 5,044,632 A | 9/1991 | Jones |
| 5,048,825 A | 9/1991 | Kelly |
| 5,048,826 A | 9/1991 | Ryan |
| 5,050,872 A | 9/1991 | Farenholtz |
| 5,050,873 A | 9/1991 | Jones |

(56) References Cited

U.S. PATENT DOCUMENTS

| | | |
|---|---|---|
| 5,051,638 A | 9/1991 | Pyles |
| 5,052,684 A | 10/1991 | Kosuge et al. |
| 5,056,777 A | 10/1991 | Capjon et al. |
| 5,058,881 A | 10/1991 | Measom |
| 5,058,882 A | 10/1991 | Dalebout et al. |
| 5,058,884 A | 10/1991 | Fuller, Sr. |
| 5,058,888 A | 10/1991 | Walker et al. |
| 5,062,626 A | 11/1991 | Dalebout |
| 5,062,627 A | 11/1991 | Bingham |
| 5,062,630 A | 11/1991 | Nelson |
| 5,062,631 A | 11/1991 | Dau et al. |
| 5,062,632 A | 11/1991 | Dalebout |
| 5,062,633 A | 11/1991 | Engel et al. |
| 5,064,191 A | 11/1991 | Johnson |
| 5,067,710 A | 11/1991 | Watterson |
| 5,071,115 A | 12/1991 | Welch |
| 5,071,119 A | 12/1991 | Johnson |
| 5,072,929 A | 12/1991 | Peterson |
| 5,074,550 A | 12/1991 | Sloan |
| D323,009 S | 1/1992 | Dalebout |
| D323,198 S | 1/1992 | Dalebout |
| D323,199 S | 1/1992 | Dalebout |
| 5,080,353 A | 1/1992 | Tench |
| D323,863 S | 2/1992 | Watterson |
| 5,085,430 A | 2/1992 | Habing |
| 5,088,729 A | 2/1992 | Dalebout |
| 5,090,694 A | 2/1992 | Pauls et al. |
| 5,094,449 A | 3/1992 | Stearns |
| 5,100,129 A | 3/1992 | Porter |
| 5,102,121 A | 4/1992 | Solow et al. |
| 5,102,122 A | 4/1992 | Piane, Jr. |
| 5,102,124 A | 4/1992 | Diodati |
| 5,102,380 A | 4/1992 | Jacobson |
| 5,104,120 A | 4/1992 | Watterson et al. |
| 5,106,079 A | 4/1992 | Escobedo |
| 5,108,090 A | 4/1992 | Reed |
| 5,108,093 A | 4/1992 | Watterson |
| D326,491 S | 5/1992 | Dalebout |
| 5,110,117 A | 5/1992 | Fisher et al. |
| 5,110,118 A | 5/1992 | Winey |
| 5,110,121 A | 5/1992 | Foster |
| 5,112,287 A | 5/1992 | Brewer |
| 5,114,391 A | 5/1992 | Pitzen et al. |
| 5,116,297 A | 5/1992 | Stonecipher |
| 5,120,289 A | 6/1992 | Yu |
| 5,122,105 A | 6/1992 | Engel |
| 5,123,885 A | 6/1992 | Shields |
| 5,123,886 A | 6/1992 | Cook |
| 5,125,647 A | 6/1992 | Smith |
| 5,125,884 A | 6/1992 | Weber et al. |
| 5,129,872 A | 7/1992 | Dalton et al. |
| 5,131,898 A | 7/1992 | Panagos |
| 5,135,216 A | 8/1992 | Bingham et al. |
| 5,135,445 A | 8/1992 | Christensen |
| 5,135,449 A | 8/1992 | Jones |
| 5,135,453 A | 8/1992 | Sollenberger |
| 5,135,458 A | 8/1992 | Huang |
| 5,135,459 A | 8/1992 | Perry, Jr. |
| 5,137,272 A | 8/1992 | Wilkinson |
| 5,141,478 A | 8/1992 | Upper |
| 5,141,483 A | 8/1992 | Smith |
| 5,145,481 A | 9/1992 | Friedebach |
| 5,147,265 A | 9/1992 | Pauls |
| 5,147,266 A | 9/1992 | Ricard |
| 5,149,084 A | 9/1992 | Dalebout |
| 5,149,312 A | 9/1992 | Croft et al. |
| 5,151,071 A | 9/1992 | Jain et al. |
| 5,156,650 A | 10/1992 | Bals |
| 5,158,518 A | 10/1992 | Pizzuto |
| 5,158,520 A | 10/1992 | Lemke et al. |
| 5,160,305 A | 11/1992 | Lin |
| 5,167,850 A | 12/1992 | Shtarkman |
| 5,169,362 A | 12/1992 | Schwartz |
| 5,169,363 A | 12/1992 | Campanaro |
| 5,171,196 A | 12/1992 | Lynch |
| D332,347 S | 1/1993 | Raadt |
| 5,176,601 A | 1/1993 | Reynolds |
| 5,176,602 A | 1/1993 | Roberts |
| 5,178,590 A | 1/1993 | Stephens |
| 5,178,599 A | 1/1993 | Scott |
| 5,180,352 A | 1/1993 | Sreter |
| 5,181,894 A | 1/1993 | Shieng |
| 5,184,991 A | 2/1993 | Brangi |
| 5,184,994 A | 2/1993 | Morris |
| 5,190,505 A | 3/1993 | Dalebout |
| 5,190,509 A | 3/1993 | Davison, Jr. |
| 5,190,513 A | 3/1993 | Habing et al. |
| 5,192,255 A | 3/1993 | Dalebout et al. |
| 5,192,257 A | 3/1993 | Panasewicz |
| 5,194,059 A | 3/1993 | Wu |
| 5,195,937 A | 3/1993 | Engel et al. |
| 5,199,934 A | 4/1993 | Lin |
| 5,199,935 A | 4/1993 | Gibson et al. |
| 5,201,694 A | 4/1993 | Zappel |
| 5,201,772 A | 4/1993 | Maxwell |
| 5,203,126 A | 4/1993 | Sorenson et al. |
| 5,203,826 A | 4/1993 | Dalebout |
| 5,205,802 A | 4/1993 | Swisher |
| D335,511 S | 5/1993 | Engel |
| D335,905 S | 5/1993 | Cutter |
| 5,207,622 A | 5/1993 | Wilkinson et al. |
| 5,209,223 A | 5/1993 | McGorry et al. |
| 5,209,482 A | 5/1993 | Hopfer |
| 5,209,715 A | 5/1993 | Walker et al. |
| 5,211,614 A | 5/1993 | Henes |
| 5,211,617 A | 5/1993 | Millen |
| D336,498 S | 6/1993 | Engel |
| 5,217,422 A | 6/1993 | Domzalski |
| 5,217,487 A | 6/1993 | Engel |
| 5,221,240 A | 6/1993 | Mann |
| 5,221,245 A | 6/1993 | Yeh |
| 5,222,928 A | 6/1993 | Yacullo |
| D337,361 S | 7/1993 | Engel |
| D337,666 S | 7/1993 | Peterson |
| D337,799 S | 7/1993 | Cutter |
| 5,224,909 A | 7/1993 | Hamilton |
| 5,226,866 A | 7/1993 | Engel et al. |
| 5,226,868 A | 7/1993 | Montgomery |
| 5,230,680 A | 7/1993 | Wu |
| 5,231,752 A | 8/1993 | Hereford |
| 5,232,422 A | 8/1993 | Bishop, Jr. |
| 5,234,395 A | 8/1993 | Miller et al. |
| 5,236,406 A | 8/1993 | Webber |
| 5,242,339 A * | 9/1993 | Thornton ............... A63B 22/02 482/54 |
| 5,242,340 A | 9/1993 | Jerome |
| 5,242,342 A | 9/1993 | Silverman |
| 5,242,344 A | 9/1993 | Hundley |
| 5,242,345 A | 9/1993 | Mitchell |
| 5,242,348 A | 9/1993 | Bates |
| 5,242,353 A | 9/1993 | Cole et al. |
| 5,244,444 A | 9/1993 | Wostry |
| 5,244,446 A | 9/1993 | Engel |
| 5,247,853 A | 9/1993 | Dalebout |
| 5,250,013 A | 10/1993 | Brangi |
| 5,254,065 A | 10/1993 | Pollock |
| 5,254,066 A | 10/1993 | Brown et al. |
| 5,254,067 A | 10/1993 | Habing et al. |
| 5,256,117 A | 10/1993 | Potts et al. |
| 5,256,121 A | 10/1993 | Brotman |
| 5,256,126 A | 10/1993 | Grotstein |
| 5,259,611 A | 11/1993 | Dalebout |
| 5,261,865 A | 11/1993 | Trainor |
| 5,263,913 A | 11/1993 | Boren |
| 5,263,915 A | 11/1993 | Habing |
| 5,263,916 A | 11/1993 | Bobich |
| D342,106 S | 12/1993 | Campbell |
| 5,267,929 A | 12/1993 | Chen |
| 5,267,930 A | 12/1993 | Henes |
| 5,269,736 A | 12/1993 | Roberts |
| 5,269,737 A | 12/1993 | Sobotka |
| 5,269,738 A | 12/1993 | Boren |
| 5,271,416 A | 12/1993 | Lepley |
| 5,273,505 A | 12/1993 | Jones |

(56) References Cited

U.S. PATENT DOCUMENTS

| | | |
|---|---|---|
| 5,277,683 A | 1/1994 | Wilkins |
| 5,277,684 A | 1/1994 | Harris |
| 5,279,528 A | 1/1994 | Dalebout et al. |
| 5,280,936 A | 1/1994 | Schmidlin |
| 5,281,193 A | 1/1994 | Colbo, Jr. |
| D344,112 S | 2/1994 | Smith |
| D344,557 S | 2/1994 | Ashby |
| 5,282,776 A | 2/1994 | Dalebout |
| 5,284,461 A | 2/1994 | Wilkinson et al. |
| 5,284,463 A | 2/1994 | Shields |
| 5,284,464 A | 2/1994 | Lee, III et al. |
| 5,286,243 A | 2/1994 | Lapcevic |
| 5,290,214 A | 3/1994 | Chen |
| 5,292,297 A | 3/1994 | Hsu |
| 5,295,931 A | 3/1994 | Dreibelbis |
| 5,298,002 A | 3/1994 | Lin |
| 5,299,992 A | 4/1994 | Wilkinson |
| 5,299,993 A | 4/1994 | Habing |
| 5,299,997 A | 4/1994 | Chen |
| 5,302,161 A | 4/1994 | Loubert et al. |
| 5,303,885 A | 4/1994 | Wade |
| 5,306,218 A | 4/1994 | Huang Chen |
| 5,306,221 A | 4/1994 | Itaru |
| D347,251 S | 5/1994 | Dreibelbis |
| 5,308,234 A | 5/1994 | Nicke et al. |
| 5,308,304 A | 5/1994 | Habing |
| 5,310,394 A | 5/1994 | Kallios |
| 5,314,390 A | 5/1994 | Westing et al. |
| 5,316,534 A | 5/1994 | Dalebout et al. |
| 5,318,490 A | 6/1994 | Henderson et al. |
| 5,318,495 A | 6/1994 | Malynowsky |
| 5,320,588 A | 6/1994 | Wanzer et al. |
| 5,320,591 A | 6/1994 | Harmon et al. |
| 5,322,489 A | 6/1994 | Webb et al. |
| D348,493 S | 7/1994 | Ashby |
| D348,494 S | 7/1994 | Ashby |
| 5,328,164 A | 7/1994 | Soga |
| 5,328,410 A | 7/1994 | Amburgey et al. |
| 5,328,428 A | 7/1994 | Huang |
| 5,328,429 A | 7/1994 | Potash et al. |
| 5,328,430 A | 7/1994 | Vittone |
| 5,330,404 A | 7/1994 | Lopeteguy et al. |
| 5,330,405 A | 7/1994 | Habing et al. |
| 5,330,408 A | 7/1994 | Westmoreland, Jr. |
| D349,931 S | 8/1994 | Bostic |
| 5,334,120 A | 8/1994 | Rasmussen |
| 5,336,142 A | 8/1994 | Dalebout et al. |
| 5,336,143 A | 8/1994 | Wu |
| 5,336,148 A | 8/1994 | Ish, III |
| 5,336,151 A | 8/1994 | Van Ballegooie |
| 5,338,274 A | 8/1994 | Jones |
| 5,338,277 A | 8/1994 | Yang |
| 5,342,261 A | 8/1994 | Johnston |
| 5,342,269 A | 8/1994 | Huang |
| 5,342,271 A | 8/1994 | Long |
| 5,344,372 A | 9/1994 | Hung |
| 5,344,374 A | 9/1994 | Telle |
| 5,344,376 A | 9/1994 | Bostic et al. |
| 5,346,447 A | 9/1994 | Stearns |
| 5,348,524 A | 9/1994 | Grant |
| 5,350,344 A | 9/1994 | Kissel |
| 5,350,345 A | 9/1994 | Frey |
| D351,202 S | 10/1994 | Bingham |
| D351,435 S | 10/1994 | Peterson |
| D351,633 S | 10/1994 | Bingham |
| 5,352,171 A | 10/1994 | Lin |
| 5,352,174 A | 10/1994 | Mason et al. |
| 5,354,251 A | 10/1994 | Sleamaker |
| 5,354,252 A | 10/1994 | Habing |
| 5,354,253 A | 10/1994 | Awbrey et al. |
| 5,356,003 A | 10/1994 | Gretz et al. |
| 5,356,357 A | 10/1994 | Wang et al. |
| 5,356,358 A | 10/1994 | Chen |
| 5,356,360 A | 10/1994 | Johns |
| 5,358,462 A | 10/1994 | Calderone |
| D352,534 S | 11/1994 | Dreibelbis |
| 5,362,290 A | 11/1994 | Huang |
| 5,362,295 A | 11/1994 | Nurge |
| 5,362,296 A | 11/1994 | Wang et al. |
| 5,364,060 A | 11/1994 | Donovan et al. |
| 5,366,428 A | 11/1994 | Liao |
| 5,366,432 A | 11/1994 | Habing et al. |
| 5,368,042 A | 11/1994 | O'Neal et al. |
| 5,368,536 A | 11/1994 | Stodgell |
| D353,422 S | 12/1994 | Bostic |
| 5,370,594 A | 12/1994 | Grinblat |
| 5,372,556 A | 12/1994 | Ropp |
| 5,372,559 A | 12/1994 | Dalebout et al. |
| 5,372,564 A | 12/1994 | Spirito |
| 5,374,227 A | 12/1994 | Webb |
| 5,374,228 A | 12/1994 | Buisman |
| 5,374,230 A | 12/1994 | Bonnaime |
| 5,376,053 A | 12/1994 | Ponder |
| 5,378,216 A | 1/1995 | Ish, III et al. |
| 5,382,221 A | 1/1995 | Hsu |
| 5,385,520 A | 1/1995 | Lepine |
| 5,387,168 A | 2/1995 | Bostic |
| 5,387,170 A | 2/1995 | Rawls et al. |
| 5,387,171 A | 2/1995 | Casey et al. |
| 5,391,132 A | 2/1995 | Greenwald |
| 5,392,476 A | 2/1995 | Williams |
| 5,393,690 A | 2/1995 | Fu |
| D356,128 S | 3/1995 | Smith |
| 5,397,287 A | 3/1995 | Lindfors |
| 5,403,253 A | 4/1995 | Gaylord |
| 5,403,256 A | 4/1995 | Squires |
| 5,407,402 A | 4/1995 | Brown et al. |
| 5,407,403 A | 4/1995 | Coleman |
| 5,407,404 A | 4/1995 | Killian et al. |
| 5,407,405 A | 4/1995 | Oren |
| 5,407,411 A | 4/1995 | Trainor |
| 5,407,414 A | 4/1995 | Bass |
| 5,409,330 A | 4/1995 | Naines et al. |
| 5,409,435 A | 4/1995 | Daniels |
| 5,413,546 A | 5/1995 | Basile |
| 5,413,551 A | 5/1995 | Wu |
| 5,415,608 A | 5/1995 | Bode |
| 5,417,634 A | 5/1995 | Habing |
| 5,419,747 A | 5/1995 | Piaget |
| 5,419,749 A | 5/1995 | Morgenstein |
| 5,419,751 A | 5/1995 | Byrd et al. |
| 5,421,795 A | 6/1995 | Chen |
| 5,421,796 A | 6/1995 | Jones et al. |
| 5,421,798 A | 6/1995 | Bond et al. |
| 5,421,800 A | 6/1995 | Mullen |
| 5,421,801 A | 6/1995 | Davies, III et al. |
| 5,423,730 A | 6/1995 | Hirsch |
| 5,423,731 A | 6/1995 | Chen |
| 5,429,563 A | 7/1995 | Engel |
| 5,429,567 A | 7/1995 | Gerschefske et al. |
| 5,429,568 A | 7/1995 | Chen |
| 5,429,569 A | 7/1995 | Gunnari |
| 5,431,612 A | 7/1995 | Holden |
| 5,433,685 A | 7/1995 | Winslow |
| 5,435,798 A | 7/1995 | Habing et al. |
| 5,435,799 A | 7/1995 | Lundin |
| 5,435,801 A | 7/1995 | Hung |
| D360,915 S | 8/1995 | Bostic |
| 5,437,589 A | 8/1995 | Habing |
| 5,439,225 A | 8/1995 | Gvoich et al. |
| 5,443,435 A | 8/1995 | Wilkinson |
| 5,447,480 A | 9/1995 | Fulks |
| 5,449,332 A | 9/1995 | Hervig |
| 5,451,191 A | 9/1995 | Beenken |
| 5,453,066 A | 9/1995 | Richter, Jr. |
| 5,456,644 A | 10/1995 | Hecox et al. |
| 5,458,553 A | 10/1995 | Wu |
| 5,460,586 A | 10/1995 | Wilkinson |
| 5,464,378 A | 11/1995 | Lee |
| 5,467,874 A | 11/1995 | Whitaker |
| 5,468,205 A | 11/1995 | McFall et al. |
| 5,472,397 A | 12/1995 | Ammoscato et al. |
| 5,472,399 A | 12/1995 | Szekely |
| 5,476,428 A | 12/1995 | Potash et al. |

(56) References Cited

U.S. PATENT DOCUMENTS

| | | |
|---|---|---|
| 5,478,298 A | 12/1995 | Chen |
| 5,480,212 A | 1/1996 | Marconet |
| 5,484,358 A | 1/1996 | Wang et al. |
| 5,484,365 A | 1/1996 | Jones et al. |
| 5,489,249 A | 2/1996 | Brewer et al. |
| 5,492,517 A | 2/1996 | Bostic |
| 5,492,518 A | 2/1996 | Measom |
| 5,493,127 A | 2/1996 | Lloyd et al. |
| D367,689 S | 3/1996 | Wilkinson |
| 5,496,238 A | 3/1996 | Taylor |
| 5,496,244 A | 3/1996 | Caruthers |
| 5,498,222 A | 3/1996 | Hur |
| 5,498,223 A | 3/1996 | Iams et al. |
| 5,499,959 A | 3/1996 | Holmes et al. |
| 5,499,961 A | 3/1996 | Mattox |
| 5,501,647 A | 3/1996 | Snyder |
| 5,501,656 A | 3/1996 | Homma et al. |
| 5,503,608 A | 4/1996 | Chang |
| 5,505,677 A | 4/1996 | Hinds |
| 5,507,710 A | 4/1996 | Chen |
| 5,511,740 A | 4/1996 | Loubert |
| 5,512,025 A | 4/1996 | Dalebout et al. |
| 5,514,059 A | 5/1996 | Romney |
| 5,518,476 A | 5/1996 | Mcleon |
| 5,518,477 A | 5/1996 | Simonson |
| 5,518,483 A | 5/1996 | Oswald |
| 5,518,486 A | 5/1996 | Sheeler |
| 5,520,599 A | 5/1996 | Chen |
| D370,949 S | 6/1996 | Furner |
| D371,176 S | 6/1996 | Furner |
| 5,522,783 A | 6/1996 | Gordon |
| 5,527,245 A | 6/1996 | Dalebout et al. |
| 5,527,249 A | 6/1996 | Harris |
| 5,527,250 A | 6/1996 | Chen |
| 5,527,253 A | 6/1996 | Wilkinson |
| 5,529,553 A | 6/1996 | Finlayson |
| 5,529,554 A | 6/1996 | Eschenbach |
| 5,529,560 A | 6/1996 | Dise |
| 5,533,899 A | 7/1996 | Young |
| 5,533,952 A | 7/1996 | Schaber |
| 5,540,429 A | 7/1996 | Dalebout |
| 5,540,642 A | 7/1996 | Sprague |
| 5,545,114 A | 8/1996 | Gvoich |
| 5,549,530 A | 8/1996 | Fulks |
| 5,549,532 A | 8/1996 | Kropp |
| 5,549,533 A | 8/1996 | Olson et al. |
| 5,554,085 A | 9/1996 | Dalebout |
| 5,554,086 A | 9/1996 | Habing et al. |
| 5,556,362 A | 9/1996 | Whipps |
| 5,556,369 A | 9/1996 | Roberts |
| 5,558,608 A | 9/1996 | Hall |
| 5,562,577 A | 10/1996 | Nichols, Sr. et al. |
| 5,569,128 A | 10/1996 | Dalebout |
| 5,569,133 A | 10/1996 | Vittone |
| 5,569,138 A | 10/1996 | Wang et al. |
| 5,571,064 A | 11/1996 | Holm |
| 5,573,485 A | 11/1996 | Geschwender |
| 5,575,740 A | 11/1996 | Piaget |
| 5,577,985 A | 11/1996 | Miller |
| 5,577,987 A | 11/1996 | Brown |
| 5,580,340 A | 12/1996 | Yu |
| 5,580,341 A | 12/1996 | Simonson |
| 5,582,565 A | 12/1996 | Soria |
| 5,586,811 A | 12/1996 | Tornero |
| 5,586,962 A | 12/1996 | Hallmark |
| 5,588,938 A | 12/1996 | Schneider et al. |
| 5,588,942 A | 12/1996 | Dillard |
| 5,591,105 A | 1/1997 | Dalebout |
| 5,591,106 A | 1/1997 | Dalebout |
| 5,595,545 A | 1/1997 | O'Brien |
| 5,595,556 A | 1/1997 | Dalebout et al. |
| 5,595,559 A | 1/1997 | Viel |
| 5,597,362 A | 1/1997 | Lee |
| 5,597,375 A | 1/1997 | Simonson |
| 5,599,261 A | 2/1997 | Easley et al. |
| 5,601,518 A | 2/1997 | Weintraub |
| 5,603,678 A | 2/1997 | Wilson |
| 5,605,524 A | 2/1997 | Husted |
| 5,607,250 A | 3/1997 | Tatterson et al. |
| 5,607,375 A | 3/1997 | Dalebout |
| 5,609,278 A | 3/1997 | Fresco |
| 5,611,539 A | 3/1997 | Watterson |
| 5,613,924 A | 3/1997 | Lee |
| 5,613,928 A | 3/1997 | Laudone |
| 5,616,106 A | 4/1997 | Abelbeck |
| 5,616,107 A | 4/1997 | Simonson |
| 5,616,111 A | 4/1997 | Randolph |
| 5,618,250 A | 4/1997 | Butz |
| 5,620,402 A | 4/1997 | Simonson |
| 5,620,403 A | 4/1997 | Lundin |
| 5,622,527 A | 4/1997 | Watterson et al. |
| 5,624,353 A | 4/1997 | Naidus |
| 5,624,360 A | 4/1997 | Wilkins |
| 5,624,361 A | 4/1997 | Lai |
| 5,626,538 A | 5/1997 | Dalebout |
| 5,626,540 A | 5/1997 | Hall |
| 5,626,542 A | 5/1997 | Dalebout |
| 5,626,546 A | 5/1997 | Little |
| 5,626,548 A | 5/1997 | Coyle |
| 5,628,715 A | 5/1997 | Simonson |
| 5,628,716 A | 5/1997 | Brice |
| 5,632,711 A | 5/1997 | Hwang |
| D380,024 S | 6/1997 | Novak |
| 5,634,870 A | 6/1997 | Wilkinson |
| 5,637,059 A | 6/1997 | Dalebout |
| 5,637,064 A | 6/1997 | Olson et al. |
| D380,509 S | 7/1997 | Wilkinson |
| 5,643,153 A | 7/1997 | Nylen |
| 5,643,162 A | 7/1997 | Landers et al. |
| 5,645,509 A | 7/1997 | Brewer |
| 5,645,510 A | 7/1997 | Wilkinson |
| 5,653,669 A | 8/1997 | Cheng |
| 5,655,997 A | 8/1997 | Greenberg et al. |
| 5,656,001 A | 8/1997 | Baatz |
| 5,658,227 A | 8/1997 | Stearns |
| D384,118 S | 9/1997 | Deblauw |
| 5,662,557 A | 9/1997 | Watterson et al. |
| 5,665,031 A | 9/1997 | Hsieh |
| 5,665,041 A | 9/1997 | Hsieh |
| 5,667,461 A | 9/1997 | Hall |
| 5,667,465 A | 9/1997 | McCollum et al. |
| 5,669,455 A | 9/1997 | Dietrich |
| 5,669,857 A | 9/1997 | Watterson et al. |
| 5,669,862 A | 9/1997 | Sayman |
| 5,669,865 A | 9/1997 | Gordon |
| 5,672,140 A | 9/1997 | Watterson et al. |
| 5,674,156 A | 10/1997 | Watterson et al. |
| 5,674,167 A | 10/1997 | Piaget et al. |
| 5,674,453 A | 10/1997 | Watterson et al. |
| 5,676,624 A | 10/1997 | Watterson et al. |
| 5,679,100 A | 10/1997 | Charnitski |
| 5,681,247 A | 10/1997 | Webber |
| 5,681,249 A | 10/1997 | Endelman |
| 5,683,331 A | 11/1997 | Dalebout |
| 5,683,332 A | 11/1997 | Watterson et al. |
| 5,683,334 A | 11/1997 | Webber |
| 5,685,804 A | 11/1997 | Whan-Tong et al. |
| 5,685,810 A | 11/1997 | Chung |
| 5,688,196 A | 11/1997 | O'Neil |
| 5,688,210 A | 11/1997 | Chou |
| 5,688,212 A | 11/1997 | Walker |
| D387,825 S | 12/1997 | Fleck |
| 5,692,996 A | 12/1997 | Widerman |
| 5,692,997 A | 12/1997 | Stearns |
| 5,693,004 A | 12/1997 | Carlson et al. |
| 5,695,433 A | 12/1997 | Buisman |
| 5,695,434 A | 12/1997 | Dalebout et al. |
| 5,695,435 A | 12/1997 | Dalebout et al. |
| 5,702,325 A | 12/1997 | Watterson et al. |
| 5,704,879 A | 1/1998 | Watterson et al. |
| 5,707,168 A | 1/1998 | Sharon |
| 5,709,428 A | 1/1998 | Hugghins |
| 5,709,633 A | 1/1998 | Sokol |
| 5,709,634 A | 1/1998 | Pointer |

(56) References Cited

U.S. PATENT DOCUMENTS

| | | |
|---|---|---|
| 5,709,636 A | 1/1998 | Vallone |
| 5,709,638 A | 1/1998 | Mackert et al. |
| 5,711,746 A | 1/1998 | Carlson |
| 5,711,749 A | 1/1998 | Miller |
| 5,716,308 A | 2/1998 | Lee |
| 5,718,657 A | 2/1998 | Dalebout et al. |
| 5,718,660 A | 2/1998 | Chen |
| 5,720,200 A | 2/1998 | Anderson |
| 5,720,698 A | 2/1998 | Dalebout |
| 5,720,702 A | 2/1998 | Lee |
| D392,006 S | 3/1998 | Dalebout |
| 5,722,917 A | 3/1998 | Olschansky et al. |
| 5,722,921 A | 3/1998 | Simonson |
| 5,722,922 A | 3/1998 | Watterson et al. |
| 5,725,459 A | 3/1998 | Rexach |
| 5,725,463 A | 3/1998 | Colonello et al. |
| 5,733,227 A | 3/1998 | Lee |
| 5,733,229 A | 3/1998 | Dalebout et al. |
| 5,733,232 A | 3/1998 | Hsu |
| 5,735,773 A | 4/1998 | Vittone |
| 5,738,616 A | 4/1998 | Robertson |
| 5,743,833 A | 4/1998 | Watterson et al. |
| 5,746,687 A | 5/1998 | Vial et al. |
| 5,746,688 A | 5/1998 | Prager |
| 5,749,668 A | 5/1998 | McIlvain |
| 5,749,807 A | 5/1998 | Webb |
| 5,749,809 A | 5/1998 | Lin |
| 5,749,813 A | 5/1998 | Domzalski |
| 5,752,879 A | 5/1998 | Berdut |
| 5,752,901 A | 5/1998 | Lee |
| 5,755,645 A | 5/1998 | Miller et al. |
| 5,755,646 A | 5/1998 | Chu |
| 5,755,823 A | 5/1998 | Cleary |
| 5,759,139 A | 6/1998 | Wright |
| 5,762,584 A | 6/1998 | Daniels |
| 5,762,587 A | 6/1998 | Dalebout et al. |
| 5,766,118 A | 6/1998 | Conner |
| 5,769,759 A | 6/1998 | Alter |
| 5,769,762 A | 6/1998 | Towley, III et al. |
| 5,772,560 A | 6/1998 | Watterson et al. |
| 5,772,563 A | 6/1998 | Lin |
| 5,776,040 A | 7/1998 | Webb et al. |
| 5,779,604 A | 7/1998 | Towley, III et al. |
| 5,779,607 A | 7/1998 | Harris |
| 5,785,632 A | 7/1998 | Greenberg et al. |
| 5,788,616 A | 8/1998 | Polidi |
| 5,788,618 A | 8/1998 | Joutras |
| 5,792,027 A | 8/1998 | Gvoich |
| 5,792,028 A | 8/1998 | Jarvie |
| 5,792,029 A | 8/1998 | Gordon |
| 5,792,034 A | 8/1998 | Kozlovsky |
| 5,795,274 A | 8/1998 | Kasbohm |
| 5,797,639 A | 8/1998 | Zorzenon |
| 5,800,310 A | 9/1998 | Jones |
| 5,800,321 A | 9/1998 | Webber |
| 5,800,323 A | 9/1998 | Ansel |
| 5,803,874 A | 9/1998 | Wilkinson |
| 5,803,877 A | 9/1998 | Franey |
| 5,803,882 A | 9/1998 | Habing et al. |
| 5,807,214 A | 9/1998 | Riazi |
| 5,810,696 A | 9/1998 | Webb |
| 5,810,698 A | 9/1998 | Hullett et al. |
| 5,810,702 A | 9/1998 | Wilkinson |
| 5,816,372 A | 10/1998 | Carlson et al. |
| 5,816,983 A | 10/1998 | Dawes et al. |
| 5,820,478 A | 10/1998 | Wood et al. |
| 5,820,529 A | 10/1998 | Weintraub |
| 5,820,532 A | 10/1998 | Oliver |
| 5,825,983 A | 10/1998 | Park et al. |
| 5,827,155 A | 10/1998 | Jensen |
| 5,827,158 A | 10/1998 | Drecksel |
| 5,829,771 A | 11/1998 | Hsu |
| 5,830,107 A | 11/1998 | Brigliadoro |
| 5,830,113 A | 11/1998 | Coody et al. |
| 5,830,114 A | 11/1998 | Halfen |
| 5,833,577 A | 11/1998 | Hurt |
| 5,833,582 A | 11/1998 | Chen |
| 5,833,584 A | 11/1998 | Piaget et al. |
| 5,833,587 A | 11/1998 | Strong et al. |
| 5,836,854 A | 11/1998 | Kuo |
| 5,836,858 A | 11/1998 | Sharff |
| 5,839,997 A | 11/1998 | Roth et al. |
| 5,842,956 A | 12/1998 | Strachan |
| 5,848,954 A | 12/1998 | Stearns et al. |
| 5,855,537 A | 1/1999 | Coody et al. |
| 5,855,538 A | 1/1999 | Argabright |
| 5,857,940 A | 1/1999 | Husted |
| 5,857,942 A | 1/1999 | Moon et al. |
| 5,857,943 A | 1/1999 | Murray |
| 5,860,190 A | 1/1999 | Cano |
| 5,860,893 A | 1/1999 | Watterson et al. |
| 5,860,894 A | 1/1999 | Dalebout et al. |
| 5,860,899 A | 1/1999 | Rassman |
| 5,865,714 A | 2/1999 | Marlowe |
| 5,868,648 A | 2/1999 | Coody et al. |
| 5,868,653 A | 2/1999 | Klasen |
| 5,871,421 A | 2/1999 | Trulaske et al. |
| 5,871,424 A | 2/1999 | Conner |
| 5,876,310 A | 3/1999 | Mackey et al. |
| 5,876,313 A | 3/1999 | Krull |
| 5,879,247 A | 3/1999 | Winter et al. |
| 5,879,271 A | 3/1999 | Stearns et al. |
| 5,879,276 A | 3/1999 | Miller |
| 5,885,196 A | 3/1999 | Gvoich |
| 5,885,197 A | 3/1999 | Barton |
| 5,891,004 A | 4/1999 | Berry |
| 5,891,042 A | 4/1999 | Sham et al. |
| 5,895,342 A | 4/1999 | Solland |
| 5,897,459 A | 4/1999 | Habing et al. |
| 5,897,463 A | 4/1999 | Maresh |
| 5,897,467 A | 4/1999 | Habing et al. |
| 5,897,469 A | 4/1999 | Yalch |
| 5,897,472 A | 4/1999 | Thulasingam |
| 5,897,474 A | 4/1999 | Romero |
| 5,899,834 A | 5/1999 | Dalebout et al. |
| 5,904,638 A | 5/1999 | Habing et al. |
| 5,906,564 A | 5/1999 | Jacobsen |
| 5,906,566 A | 5/1999 | Whitcomb |
| 5,908,373 A | 6/1999 | Pitre |
| 5,910,070 A | 6/1999 | Henry et al. |
| 5,910,073 A | 6/1999 | Conner |
| 5,911,649 A | 6/1999 | Miller |
| 5,919,118 A | 7/1999 | Stearns |
| 5,921,892 A | 7/1999 | Easton |
| 5,921,901 A | 7/1999 | Palacios |
| 5,924,966 A | 7/1999 | Havlovic |
| 5,927,780 A | 7/1999 | Chandler |
| 5,928,116 A | 7/1999 | Chiang |
| D412,953 S | 8/1999 | Armstrong |
| 5,931,767 A | 8/1999 | Morales |
| 5,935,048 A | 8/1999 | Krull |
| 5,938,551 A | 8/1999 | Warner |
| 5,938,571 A | 8/1999 | Stevens |
| 5,938,574 A | 8/1999 | Webber |
| 5,941,800 A | 8/1999 | Laconis |
| 5,941,803 A | 8/1999 | Chamberlain |
| 5,941,807 A | 8/1999 | Cassidy |
| 5,944,641 A | 8/1999 | Habing |
| 5,944,642 A | 8/1999 | Krull |
| D413,948 S | 9/1999 | Dalebout |
| 5,951,441 A | 9/1999 | Dalebout |
| 5,951,444 A | 9/1999 | Webber |
| 5,951,448 A | 9/1999 | Bolland |
| 5,954,106 A | 9/1999 | Huang |
| 5,954,621 A | 9/1999 | Joutras et al. |
| 5,957,819 A | 9/1999 | Cortesi |
| 5,961,423 A | 10/1999 | Sellers |
| 5,961,428 A | 10/1999 | Webber |
| 5,964,684 A | 10/1999 | Sokol |
| 5,967,948 A | 10/1999 | Carr |
| 5,967,950 A | 10/1999 | Hsu |
| 5,967,954 A | 10/1999 | Habing |
| 5,971,892 A | 10/1999 | Lee |
| 5,971,895 A | 10/1999 | Habing |

(56) References Cited

U.S. PATENT DOCUMENTS

| | | |
|---|---|---|
| D416,596 S | 11/1999 | Armstrong |
| 5,984,836 A | 11/1999 | Casali |
| 5,989,164 A | 11/1999 | Kullman et al. |
| 5,989,165 A | 11/1999 | Giannelli et al. |
| 5,989,166 A | 11/1999 | Capizzo et al. |
| 5,993,358 A | 11/1999 | Gureghian et al. |
| 5,997,447 A | 12/1999 | Giannelli et al. |
| 5,998,897 A | 12/1999 | Bosten et al. |
| 6,003,166 A | 12/1999 | Hald |
| 6,003,294 A | 12/1999 | Fitzgerald et al. |
| 6,004,246 A | 12/1999 | Sencil |
| 6,004,247 A | 12/1999 | Webber |
| 6,007,268 A | 12/1999 | Whittington et al. |
| 6,010,432 A | 1/2000 | Vawter |
| 6,011,134 A | 1/2000 | Marks et al. |
| 6,015,367 A | 1/2000 | Scaramucci |
| 6,015,371 A | 1/2000 | Davitt |
| 6,017,293 A | 1/2000 | Pfefferle |
| 6,019,403 A | 2/2000 | Corbett |
| 6,019,710 A | 2/2000 | Dalebout |
| 6,022,300 A | 2/2000 | Hightower |
| 6,022,302 A | 2/2000 | McBride |
| 6,024,677 A | 2/2000 | Siwertz |
| 6,027,429 A | 2/2000 | Daniels |
| 6,027,433 A | 2/2000 | Flynn |
| 6,030,320 A | 2/2000 | Stearns |
| 6,033,347 A | 3/2000 | Dalebout et al. |
| 6,033,350 A | 3/2000 | Krull |
| 6,036,622 A | 3/2000 | Gordon |
| 6,036,625 A | 3/2000 | Woodruff |
| 6,039,677 A | 3/2000 | Spletzer |
| 6,039,678 A | 3/2000 | Dawson |
| 6,042,516 A * | 3/2000 | Norton .............. A63B 22/0002 482/54 |
| 6,042,523 A | 3/2000 | Graham |
| 6,045,487 A | 4/2000 | Miller |
| 6,045,491 A | 4/2000 | McNergney |
| 6,050,920 A | 4/2000 | Ehrenfried |
| 6,050,921 A | 4/2000 | Wang |
| 6,053,816 A | 4/2000 | Immel |
| 6,053,853 A | 4/2000 | Hinds |
| D425,940 S | 5/2000 | Halfen |
| 6,056,678 A | 5/2000 | Giannelli et al. |
| 6,059,692 A | 5/2000 | Hickman |
| 6,059,695 A | 5/2000 | Hung |
| 6,059,698 A | 5/2000 | Mazor |
| 6,059,701 A | 5/2000 | George et al. |
| 6,065,572 A | 5/2000 | Schober et al. |
| 6,066,077 A | 5/2000 | Horst |
| 6,071,216 A | 6/2000 | Giannelli et al. |
| 6,071,217 A | 6/2000 | Barnett |
| 6,074,328 A | 6/2000 | Johnson |
| 6,077,199 A | 6/2000 | Hsu |
| 6,077,200 A | 6/2000 | Lin |
| 6,079,915 A | 6/2000 | Bosten et al. |
| 6,080,091 A | 6/2000 | Habing et al. |
| 6,082,346 A | 7/2000 | Andrews et al. |
| 6,083,144 A | 7/2000 | Towley, III et al. |
| 6,086,520 A | 7/2000 | Rodriquez |
| 6,086,521 A | 7/2000 | Solland |
| 6,090,016 A | 7/2000 | Kuo |
| 6,090,020 A | 7/2000 | Webber |
| D428,949 S | 8/2000 | Simonson |
| 6,095,954 A | 8/2000 | Svanberg |
| 6,099,442 A | 8/2000 | Krull |
| 6,099,444 A | 8/2000 | Domenge |
| 6,101,684 A | 8/2000 | Ginocchio |
| 6,102,836 A | 8/2000 | Person |
| 6,102,837 A | 8/2000 | Hubbard |
| 6,106,437 A | 8/2000 | Brooks |
| 6,106,439 A | 8/2000 | Boland |
| 6,110,075 A | 8/2000 | Woodruff |
| 6,110,076 A | 8/2000 | Hurt |
| 6,110,081 A | 8/2000 | Barrett |
| 6,112,624 A | 9/2000 | Chen |
| 6,113,323 A | 9/2000 | Bosten et al. |
| 6,113,518 A | 9/2000 | Maresh |
| 6,113,519 A | 9/2000 | Goto |
| 6,113,522 A | 9/2000 | Montgomery |
| 6,113,564 A | 9/2000 | McGuire |
| 6,117,049 A | 9/2000 | Lowe |
| 6,120,424 A | 9/2000 | Arline |
| 6,123,646 A | 9/2000 | Colassi |
| 6,123,649 A | 9/2000 | Lee |
| 6,123,650 A | 9/2000 | Birrell |
| 6,126,577 A | 10/2000 | Chang |
| 6,128,981 A | 10/2000 | Bondhus et al. |
| 6,129,651 A | 10/2000 | Denaro |
| 6,132,347 A | 10/2000 | Alessandri |
| 6,135,926 A | 10/2000 | Lee |
| 6,135,927 A | 10/2000 | Lo |
| 6,149,551 A | 11/2000 | Pyles et al. |
| 6,149,556 A | 11/2000 | Jordan |
| 6,149,558 A | 11/2000 | Chen |
| 6,149,559 A | 11/2000 | Mackey |
| 6,152,864 A | 11/2000 | Giannelli et al. |
| 6,162,153 A | 12/2000 | Perez, Jr. |
| 6,165,107 A | 12/2000 | Birrell |
| 6,165,110 A | 12/2000 | Gajda |
| 6,168,557 B1 | 1/2001 | Liao |
| 6,171,217 B1 | 1/2001 | Cutler |
| 6,171,219 B1 | 1/2001 | Simonson |
| 6,172,178 B1 | 1/2001 | Koning et al. |
| 6,174,265 B1 | 1/2001 | Alessandri |
| 6,174,267 B1 | 1/2001 | Dalebout |
| 6,174,268 B1 | 1/2001 | Novak |
| 6,175,994 B1 | 1/2001 | Nicoletti |
| 6,179,748 B1 | 1/2001 | Barr |
| 6,183,397 B1 | 2/2001 | Stearns et al. |
| 6,183,400 B1 | 2/2001 | Pope |
| 6,183,401 B1 | 2/2001 | Krull |
| 6,183,403 B1 | 2/2001 | Dunn |
| 6,186,290 B1 | 2/2001 | Carlson |
| 6,186,926 B1 | 2/2001 | Ellis |
| 6,186,927 B1 | 2/2001 | Krull |
| 6,186,928 B1 | 2/2001 | Chen |
| 6,186,929 B1 | 2/2001 | Endelman et al. |
| 6,190,289 B1 | 2/2001 | Pyles et al. |
| 6,193,631 B1 | 2/2001 | Hickman |
| 6,193,635 B1 | 2/2001 | Webber et al. |
| 6,196,952 B1 | 3/2001 | Chen |
| 6,196,954 B1 | 3/2001 | Chen |
| 6,199,732 B1 | 3/2001 | Swetish |
| 6,203,473 B1 | 3/2001 | Atwood |
| 6,203,474 B1 | 3/2001 | Jones |
| 6,206,804 B1 | 3/2001 | Maresh |
| 6,213,923 B1 | 4/2001 | Cameron et al. |
| 6,217,483 B1 | 4/2001 | Kallassy |
| 6,217,493 B1 | 4/2001 | Spletzer |
| 6,217,495 B1 | 4/2001 | Yalch |
| 6,220,990 B1 | 4/2001 | Crivello |
| 6,220,992 B1 | 4/2001 | Shafik |
| 6,224,519 B1 | 5/2001 | Doolittle |
| 6,228,003 B1 | 5/2001 | Hald et al. |
| 6,231,489 B1 | 5/2001 | McBride et al. |
| 6,234,941 B1 | 5/2001 | Chu |
| 6,238,322 B1 | 5/2001 | Hsu |
| 6,238,323 B1 | 5/2001 | Simonson |
| 6,241,553 B1 | 6/2001 | Hsia |
| 6,244,995 B1 | 6/2001 | Prsala |
| 6,245,001 B1 | 6/2001 | Siaperas |
| 6,251,048 B1 | 6/2001 | Kaufman |
| 6,251,052 B1 | 6/2001 | Simonson |
| 6,254,516 B1 | 7/2001 | Giannelli et al. |
| 6,261,022 B1 | 7/2001 | Dalebout et al. |
| 6,264,272 B1 | 7/2001 | Jones et al. |
| 6,264,588 B1 | 7/2001 | Ellis |
| 6,267,711 B1 | 7/2001 | Hinds |
| 6,280,361 B1 | 8/2001 | Harvey et al. |
| 6,280,362 B1 | 8/2001 | Dalebout et al. |
| 6,283,859 B1 | 9/2001 | Carlson et al. |
| 6,287,240 B1 | 9/2001 | Trabbic |
| 6,287,241 B1 | 9/2001 | Ellis |
| 6,290,630 B1 | 9/2001 | Boland |

(56) References Cited

U.S. PATENT DOCUMENTS

| | | |
|---|---|---|
| 6,293,892 B1 | 9/2001 | Slawinski et al. |
| 6,296,594 B1 | 10/2001 | Simonson |
| 6,302,829 B1 | 10/2001 | Schmidt |
| 6,302,830 B1 | 10/2001 | Stearns |
| 6,302,833 B1 | 10/2001 | Ellis et al. |
| 6,309,331 B1 | 10/2001 | Raymond |
| D450,872 S | 11/2001 | Dalebout |
| 6,312,363 B1 | 11/2001 | Watterson |
| 6,312,366 B1 | 11/2001 | Prusick |
| 6,315,702 B1 | 11/2001 | Ikonomopoulos |
| 6,319,176 B1 | 11/2001 | Landfair |
| 6,319,178 B1 | 11/2001 | Webber |
| 6,319,179 B1 | 11/2001 | Hinds |
| 6,322,481 B1 | 11/2001 | Krull |
| 6,322,483 B1 | 11/2001 | Rotella |
| D452,338 S | 12/2001 | Dalebout |
| 6,328,325 B1 | 12/2001 | Greenwood |
| 6,334,624 B1 | 1/2002 | Giglio |
| 6,335,100 B1 | 1/2002 | Tominaga et al. |
| 6,338,701 B1 | 1/2002 | Webber |
| 6,340,340 B1 | 1/2002 | Stearns |
| 6,342,028 B1 | 1/2002 | De Sane |
| D453,543 S | 2/2002 | Cutler |
| D453,948 S | 2/2002 | Cutler |
| 6,347,731 B1 | 2/2002 | Burger |
| 6,350,218 B1 | 2/2002 | Dalebout et al. |
| 6,350,219 B1 | 2/2002 | Hobson |
| 6,350,221 B1 | 2/2002 | Krull |
| 6,358,187 B1 | 3/2002 | Smith |
| 6,360,408 B1 | 3/2002 | Dykstra et al. |
| 6,368,251 B1 | 4/2002 | Casler |
| 6,368,254 B1 | 4/2002 | Wall |
| 6,379,287 B1 | 4/2002 | Slawinski et al. |
| 6,387,015 B1 | 5/2002 | Watson |
| 6,387,018 B1 | 5/2002 | Krull |
| 6,387,019 B1 | 5/2002 | Krull |
| 6,387,020 B1 | 5/2002 | Simonson |
| 6,387,022 B1 | 5/2002 | Smith |
| 6,387,024 B1 | 5/2002 | Monti et al. |
| 6,390,927 B1 | 5/2002 | Cleveland, III |
| 6,394,935 B1 | 5/2002 | Lake |
| 6,394,936 B1 | 5/2002 | Voris |
| 6,394,938 B1 | 5/2002 | Tornabene |
| 6,402,666 B2 | 6/2002 | Krull |
| 6,413,191 B1 | 7/2002 | Harris |
| 6,413,196 B1 | 7/2002 | Crowson |
| 6,413,197 B2 | 7/2002 | McKechnie et al. |
| 6,416,446 B1 | 7/2002 | Krull |
| 6,416,447 B1 | 7/2002 | Harmon |
| 6,422,979 B1 | 7/2002 | Krull |
| 6,422,980 B1 | 7/2002 | Simonson |
| 6,422,981 B1 | 7/2002 | Riser |
| 6,422,983 B1 | 7/2002 | Weck |
| 6,427,805 B1 | 8/2002 | Gibson et al. |
| 6,428,450 B1 | 8/2002 | Ho |
| 6,436,013 B1 | 8/2002 | Krull |
| 6,440,045 B1 | 8/2002 | Gaston |
| 6,443,521 B1 | 9/2002 | Nye et al. |
| 6,443,877 B1 | 9/2002 | Hoecht |
| 6,443,878 B1 | 9/2002 | Webber |
| 6,447,424 B1 | 9/2002 | Ashby et al. |
| 6,447,430 B1 | 9/2002 | Webb et al. |
| 6,447,432 B1 | 9/2002 | Krull |
| 6,450,923 B1 | 9/2002 | Vatti |
| 6,450,928 B1 | 9/2002 | Larkins, Jr. |
| 6,454,050 B2 | 9/2002 | Gibson et al. |
| 6,454,679 B1 | 9/2002 | Radow |
| 6,458,060 B1 | 10/2002 | Watterson |
| 6,458,061 B2 | 10/2002 | Simonson |
| 6,461,284 B1 | 10/2002 | Francavilla |
| 6,468,189 B2 | 10/2002 | Alessandri |
| 6,471,622 B1 | 10/2002 | Hammer et al. |
| 6,471,624 B1 | 10/2002 | Voris |
| 6,474,193 B1 | 11/2002 | Farney |
| 6,475,122 B2 | 11/2002 | Wu |
| 6,478,721 B1 | 11/2002 | Hunter |
| 6,482,130 B1 | 11/2002 | Pasero et al. |
| 6,482,134 B1 | 11/2002 | Rasmussen |
| 6,482,139 B1 | 11/2002 | Haag |
| 6,488,599 B2 | 12/2002 | Nye |
| 6,488,612 B2 | 12/2002 | Sechrest et al. |
| 6,491,268 B1 | 12/2002 | Channer et al. |
| 6,491,609 B2 | 12/2002 | Webber |
| 6,491,610 B1 | 12/2002 | Henn |
| 6,494,817 B2 | 12/2002 | Lake |
| 6,500,101 B1 | 12/2002 | Chen |
| 6,500,102 B1 | 12/2002 | Domenge |
| 6,506,142 B2 | 1/2003 | Itoh et al. |
| 6,510,760 B2 | 1/2003 | Matsuo |
| 6,514,180 B1 | 2/2003 | Rawls |
| 6,515,182 B2 | 2/2003 | Hosokawa et al. |
| 6,520,531 B1 | 2/2003 | Gien |
| 6,520,891 B1 | 2/2003 | Stephens, Jr. |
| 6,524,226 B2 | 2/2003 | Kushner |
| 6,527,678 B1 | 3/2003 | Wang |
| 6,527,683 B2 | 3/2003 | Tolles |
| 6,537,185 B1 | 3/2003 | Hur |
| 6,540,650 B1 | 4/2003 | Krull |
| 6,540,651 B1 | 4/2003 | Aberton et al. |
| 6,547,698 B2 | 4/2003 | Inagawa |
| 6,551,217 B2 | 4/2003 | Kaganovsky |
| 6,551,220 B1 | 4/2003 | Schroeder |
| 6,551,223 B2 | 4/2003 | Cheng |
| 6,551,226 B1 | 4/2003 | Webber et al. |
| 6,558,300 B2 | 5/2003 | Deola |
| 6,558,301 B1 | 5/2003 | Jackson |
| 6,558,302 B2 | 5/2003 | Cluff |
| 6,561,955 B1 | 5/2003 | Dreissigacker et al. |
| 6,561,956 B1 | 5/2003 | Allison |
| 6,561,960 B2 | 5/2003 | Webber |
| 6,563,225 B2 | 5/2003 | Soga |
| 6,575,882 B2 | 6/2003 | Chen |
| 6,575,885 B1 | 6/2003 | Weck et al. |
| 6,579,210 B1 | 6/2003 | Stearns et al. |
| 6,579,213 B1 | 6/2003 | Webber et al. |
| 6,579,214 B2 | 6/2003 | Crump |
| 6,582,342 B2 | 6/2003 | Kaufman |
| 6,582,345 B2 | 6/2003 | Roy |
| 6,585,626 B2 | 7/2003 | McBride |
| 6,592,498 B1 | 7/2003 | Trainor |
| 6,592,499 B2 | 7/2003 | Parker |
| 6,595,905 B2 | 7/2003 | McBride |
| 6,599,223 B2 | 7/2003 | Wang |
| 6,601,016 B1 | 7/2003 | Brown |
| 6,601,358 B2 | 8/2003 | Panatta |
| 6,605,024 B2 | 8/2003 | Stearns |
| 6,607,472 B2 | 8/2003 | Toole |
| 6,612,170 B2 | 9/2003 | Brown |
| 6,623,140 B2 | 9/2003 | Watterson |
| 6,623,407 B2 | 9/2003 | Novak |
| 6,626,799 B2 | 9/2003 | Watterson |
| 6,629,908 B2 | 10/2003 | Hamady |
| 6,629,910 B1 | 10/2003 | Krull |
| 6,632,160 B2 | 10/2003 | Lafond et al. |
| 6,632,161 B1 | 10/2003 | Nir |
| 6,634,996 B2 | 10/2003 | Jacobsen |
| 6,634,997 B2 | 10/2003 | Breibart et al. |
| 6,634,998 B2 | 10/2003 | Siaperas |
| 6,645,129 B2 | 11/2003 | Eschenbach |
| 6,645,130 B2 | 11/2003 | Webber |
| 6,652,419 B1 | 11/2003 | Rota |
| 6,652,424 B2 | 11/2003 | Dalebout |
| 6,652,426 B2 | 11/2003 | Carter |
| 6,652,429 B2 | 11/2003 | Bushnell |
| 6,652,431 B1 | 11/2003 | Mattox |
| 6,652,432 B2 | 11/2003 | Smith |
| 6,656,093 B2 | 12/2003 | Chen |
| 6,662,651 B1 | 12/2003 | Roth |
| 6,663,127 B2 | 12/2003 | Miller |
| 6,666,796 B1 | 12/2003 | MacCready, Jr. |
| 6,666,800 B2 | 12/2003 | Krull |
| 6,666,801 B1 | 12/2003 | Michalow |
| 6,669,600 B2 | 12/2003 | Warner |
| 6,669,606 B2 | 12/2003 | Krull |

(56) References Cited

U.S. PATENT DOCUMENTS

| | | | |
|---|---|---|---|
| 6,669,607 B2 | 12/2003 | Slawinski et al. |
| 6,669,609 B2 | 12/2003 | Gerschefske et al. |
| 6,672,992 B1 | 1/2004 | Lo et al. |
| 6,676,573 B2 | 1/2004 | Abelbeck et al. |
| 6,676,577 B2 | 1/2004 | Stearns |
| 6,679,816 B1 | 1/2004 | Krull |
| 6,685,600 B1 | 2/2004 | Ullman |
| 6,685,601 B1 | 2/2004 | Knapp |
| 6,685,602 B2 | 2/2004 | Colosky, Jr. et al. |
| 6,685,607 B1 | 2/2004 | Olson |
| 6,689,023 B2 | 2/2004 | Baumler |
| 6,689,025 B2 | 2/2004 | Emick |
| 6,691,839 B1 | 2/2004 | El-Kassouf |
| 6,692,415 B1 | 2/2004 | Winston |
| 6,692,417 B2 | 2/2004 | Burrell |
| 6,695,581 B2 | 2/2004 | Wasson |
| 6,695,620 B1 | 2/2004 | Huang |
| 6,699,146 B1 | 3/2004 | Winter et al. |
| 6,699,161 B1 | 3/2004 | Speas |
| 6,701,271 B2 | 3/2004 | Willner |
| 6,702,719 B1 | 3/2004 | Brown |
| 6,702,723 B2 | 3/2004 | Landfair |
| 6,702,726 B2 | 3/2004 | Lin |
| 6,705,974 B1 | 3/2004 | Tardif |
| 6,705,976 B1 | 3/2004 | Piane, Jr. |
| 6,711,789 B2 | 3/2004 | Ping |
| 6,712,740 B2 | 3/2004 | Simonson |
| 6,719,667 B2 | 4/2004 | Wong et al. |
| 6,719,672 B1 | 4/2004 | Ellis et al. |
| 6,719,674 B2 | 4/2004 | Krull |
| 6,726,601 B1 | 4/2004 | Beutel |
| 6,730,002 B2 | 5/2004 | Hald et al. |
| 6,733,424 B2 | 5/2004 | Krull |
| 6,736,759 B1 | 5/2004 | Stubbs et al. |
| 6,736,765 B2 | 5/2004 | Wallace et al. |
| 6,736,766 B1 | 5/2004 | Gallant |
| 6,743,153 B2 | 6/2004 | Watterson et al. |
| 6,746,370 B1 | 6/2004 | Fleming et al. |
| 6,746,371 B1 | 6/2004 | Brown et al. |
| 6,746,380 B2 | 6/2004 | Lien et al. |
| 6,746,381 B2 | 6/2004 | Krull |
| 6,749,537 B1 | 6/2004 | Hickman |
| 6,749,540 B1 | 6/2004 | Pasero et al. |
| 6,749,547 B2 | 6/2004 | Krull |
| 6,752,745 B1 | 6/2004 | Davis |
| 6,755,770 B2 | 6/2004 | Martens |
| 6,761,667 B1 | 7/2004 | Cutler et al. |
| 6,761,672 B1 | 7/2004 | Williams |
| 6,764,431 B2 | 7/2004 | Yoss |
| 6,764,432 B2 | 7/2004 | Hippensteel |
| 6,770,014 B2 | 8/2004 | Amore |
| 6,770,015 B2 | 8/2004 | Simonson |
| 6,783,482 B2 | 8/2004 | Oglesby et al. |
| 6,786,847 B2 | 9/2004 | Morgan et al. |
| 6,786,852 B2 | 9/2004 | Watterson et al. |
| 6,790,163 B1 | 9/2004 | Van De Laarschot |
| 6,796,925 B2 | 9/2004 | Martinez et al. |
| 6,802,800 B1 | 10/2004 | Hobson |
| 6,808,472 B1 | 10/2004 | Hickman |
| 6,811,520 B2 | 11/2004 | Wu |
| 6,821,230 B2 | 11/2004 | Dalebout et al. |
| 6,827,822 B2 | 12/2004 | Tao et al. |
| 6,830,540 B2 | 12/2004 | Watterson |
| 6,830,542 B2 | 12/2004 | Ball |
| 6,846,270 B1 | 1/2005 | Etnyre |
| 6,852,068 B2 | 2/2005 | Ogawa |
| 6,855,097 B2 | 2/2005 | Krull |
| 6,857,993 B2 | 2/2005 | Yeh |
| 6,860,131 B2 | 3/2005 | Armstrong et al. |
| 6,860,836 B1 | 3/2005 | Wu |
| 6,860,841 B1 | 3/2005 | Mortorano |
| 6,863,641 B1 | 3/2005 | Brown |
| 6,866,613 B1 | 3/2005 | Brown |
| 6,872,173 B2 | 3/2005 | Krull |
| 6,872,175 B2 | 3/2005 | Lin |
| 6,875,160 B2 | 4/2005 | Watterson et al. |
| 6,878,101 B2 | 4/2005 | Colley |
| 6,886,645 B2 | 5/2005 | Bise et al. |
| 6,893,381 B2 | 5/2005 | Slawinski |
| 6,896,342 B1 | 5/2005 | Cheng |
| 6,896,645 B1 | 5/2005 | Krull |
| 6,899,657 B2 | 5/2005 | Chuang |
| 6,899,661 B1 | 5/2005 | Krull |
| 6,902,515 B2 | 6/2005 | Howell et al. |
| 6,902,516 B2 | 6/2005 | Krull |
| 6,905,446 B2 | 6/2005 | Greenland |
| 6,908,418 B2 | 6/2005 | Saure |
| 6,910,992 B2 | 6/2005 | Arguilez |
| D507,311 S | 7/2005 | Butler |
| 6,913,562 B2 | 7/2005 | Chen |
| 6,916,278 B2 | 7/2005 | Webber |
| 6,918,858 B2 | 7/2005 | Watterson |
| 6,918,859 B1 | 7/2005 | Yeh |
| 6,918,861 B2 | 7/2005 | Liao et al. |
| 6,921,351 B1 | 7/2005 | Hickman |
| 6,921,354 B1 | 7/2005 | Shifferaw |
| 6,921,355 B2 | 7/2005 | Campanaro et al. |
| 6,923,748 B1 | 8/2005 | Mauz |
| 6,923,749 B1 | 8/2005 | Smith |
| 6,926,649 B2 | 8/2005 | Slawinski |
| 6,929,589 B1 | 8/2005 | Bruggemann et al. |
| 6,932,745 B1 | 8/2005 | Ellis |
| 6,932,748 B2 | 8/2005 | Huang |
| 6,939,271 B1 | 9/2005 | Whan-Tong et al. |
| 6,941,620 B1 | 9/2005 | Hinds |
| 6,945,916 B2 | 9/2005 | Schroeder |
| 6,945,917 B1 | 9/2005 | Baatz |
| 6,949,052 B2 | 9/2005 | Millington |
| 6,960,156 B2 | 11/2005 | Smith |
| 6,964,633 B2 | 11/2005 | Kolda |
| 6,971,974 B2 | 12/2005 | Bowman |
| 6,971,975 B2 | 12/2005 | Croft |
| 6,971,978 B2 | 12/2005 | Endelman et al. |
| 6,974,404 B1 | 12/2005 | Watterson et al. |
| 6,974,405 B2 | 12/2005 | Krull |
| 6,976,941 B2 | 12/2005 | Britt |
| 6,976,943 B1 | 12/2005 | Hsiung |
| 6,979,283 B2 | 12/2005 | Pan |
| 6,994,683 B1 | 2/2006 | Starr |
| 6,997,852 B2 | 2/2006 | Watterson |
| 6,997,856 B1 | 2/2006 | Krull |
| 7,003,122 B2 | 2/2006 | Chen |
| 7,004,887 B2 | 2/2006 | Pan et al. |
| 7,008,356 B2 | 3/2006 | Hung |
| 7,008,359 B2 | 3/2006 | Fan et al. |
| 7,011,326 B1 | 3/2006 | Schroeder et al. |
| 7,011,607 B2 | 3/2006 | Kolda et al. |
| 7,011,609 B1 | 3/2006 | Kuo |
| 7,011,610 B2 | 3/2006 | Wawrzyniak |
| 7,011,611 B1 | 3/2006 | Ripley |
| 7,014,598 B2 | 3/2006 | Fenelon et al. |
| 7,014,599 B2 | 3/2006 | Ashley |
| 7,025,713 B2 | 4/2006 | Dalebout |
| 7,029,425 B2 | 4/2006 | Krull |
| D520,085 S | 5/2006 | Willardson |
| 7,037,246 B2 | 5/2006 | Kim |
| 7,041,041 B1 | 5/2006 | Evans |
| 7,044,066 B1 | 5/2006 | Miller |
| 7,044,897 B2 | 5/2006 | Myers et al. |
| 7,048,638 B2 | 5/2006 | Novotny |
| 7,048,677 B2 | 5/2006 | Mackert |
| 7,052,442 B2 | 5/2006 | Watterson |
| 7,052,444 B2 | 5/2006 | Webber |
| 7,052,446 B2 | 5/2006 | Morris et al. |
| 7,060,006 B1 | 6/2006 | Watterson |
| 7,060,008 B2 | 6/2006 | Watterson et al. |
| 7,060,011 B1 | 6/2006 | Krull |
| 7,060,012 B2 | 6/2006 | Howell et al. |
| 7,066,867 B2 | 6/2006 | Krull |
| 7,070,539 B2 | 7/2006 | Brown |
| 7,070,542 B2 | 7/2006 | Reyes et al. |
| 7,070,545 B2 | 7/2006 | Lull et al. |
| 7,073,417 B2 | 7/2006 | Beauchamp |
| 7,077,791 B2 | 7/2006 | Krull |

(56) References Cited

U.S. PATENT DOCUMENTS

| | | |
|---|---|---|
| 7,083,536 B2 | 8/2006 | Lu et al. |
| 7,083,549 B1 | 8/2006 | Fan |
| 7,083,554 B1 | 8/2006 | Lo Presti |
| 7,086,999 B2 | 8/2006 | Jeneve et al. |
| 7,087,000 B1 | 8/2006 | Walker |
| 7,087,003 B1 | 8/2006 | Katterjohn |
| 7,087,005 B2 | 8/2006 | Rouillard |
| 7,090,625 B2 | 8/2006 | Chermack |
| 7,094,183 B2 | 8/2006 | Hsieh |
| 7,094,184 B1 | 8/2006 | Chen et al. |
| 7,094,185 B2 | 8/2006 | Greenland |
| 7,097,588 B2 | 8/2006 | Watterson |
| 7,097,593 B2 | 8/2006 | Chang |
| 7,097,601 B1 | 8/2006 | Ronnow |
| D527,776 S | 9/2006 | Willardson |
| 7,101,124 B2 | 9/2006 | Keightley |
| 7,101,322 B2 | 9/2006 | Carle |
| 7,108,636 B1 | 9/2006 | Garcia |
| 7,108,641 B2 | 9/2006 | Pertegaz-Esteban |
| 7,111,526 B1 | 9/2006 | Flojo |
| 7,112,163 B2 | 9/2006 | Krull |
| 7,112,168 B2 | 9/2006 | Dalebout et al. |
| 7,113,166 B1 | 9/2006 | Rosenberg et al. |
| 7,115,073 B2 | 10/2006 | Nizamuddin |
| 7,115,078 B1 | 10/2006 | Kalember et al. |
| 7,115,080 B2 | 10/2006 | Cockrill, Jr. et al. |
| 7,118,517 B1 | 10/2006 | Hale |
| 7,121,980 B2 | 10/2006 | Chen |
| 7,121,988 B2 | 10/2006 | Walkerdine |
| 7,125,369 B2 | 10/2006 | Endelman |
| 7,125,371 B2 | 10/2006 | Henderson |
| 7,125,373 B1 | 10/2006 | Garza |
| 7,128,693 B2 | 10/2006 | Brown |
| 7,128,696 B1 | 10/2006 | Krull |
| 7,128,697 B1 | 10/2006 | Krull |
| 7,128,701 B1 | 10/2006 | Ketcham |
| 7,132,939 B2 | 11/2006 | Tyndall et al. |
| 7,134,987 B2 | 11/2006 | Goldstein |
| 7,137,644 B2 | 11/2006 | Kimberley |
| 7,137,931 B2 | 11/2006 | Liu |
| 7,137,932 B1 | 11/2006 | Doudiet |
| 7,137,935 B2 | 11/2006 | Clarke |
| 7,137,936 B1 | 11/2006 | Shaw |
| 7,141,003 B2 | 11/2006 | Wu |
| 7,141,008 B2 | 11/2006 | Krull et al. |
| 7,150,168 B1 | 12/2006 | Kuo |
| 7,153,240 B1 | 12/2006 | Wu |
| 7,153,244 B2 | 12/2006 | Towley |
| 7,153,248 B2 | 12/2006 | Chen |
| 7,156,782 B1 | 1/2007 | Krull |
| 7,156,783 B2 | 1/2007 | Chen |
| 7,163,488 B2 | 1/2007 | Anders |
| 7,163,498 B1 | 1/2007 | Abelbeck |
| 7,163,500 B2 | 1/2007 | Endelman et al. |
| 7,166,062 B1 | 1/2007 | Watterson et al. |
| 7,166,064 B2 | 1/2007 | Watterson |
| 7,166,066 B2 | 1/2007 | Webber |
| 7,166,067 B2 | 1/2007 | Talish et al. |
| 7,169,087 B2 | 1/2007 | Ercanbrack |
| 7,169,093 B2 | 1/2007 | Simonson et al. |
| 7,172,536 B2 | 2/2007 | Liu |
| 7,172,538 B2 | 2/2007 | Keiser |
| 7,178,637 B2 | 2/2007 | Asano et al. |
| 7,179,208 B1 | 2/2007 | Nalley |
| 7,179,209 B2 | 2/2007 | Sechrest et al. |
| 7,179,212 B2 | 2/2007 | Hsiung et al. |
| 7,189,190 B2 | 3/2007 | Lamar et al. |
| 7,189,791 B2 | 3/2007 | Solan |
| 7,192,387 B2 | 3/2007 | Mendel |
| 7,192,388 B2 | 3/2007 | Dalebout et al. |
| 7,192,389 B2 | 3/2007 | Allison |
| 7,197,029 B1 | 3/2007 | Osterhout et al. |
| 7,201,712 B2 | 4/2007 | Tiahrt |
| 7,204,790 B2 | 4/2007 | Sleamaker |
| 7,207,929 B2 | 4/2007 | Hamilton |
| 7,207,930 B2 | 4/2007 | Bonutti |
| 7,211,030 B1 | 5/2007 | Cao |
| 7,214,170 B2 | 5/2007 | Sumners |
| 7,220,220 B2 | 5/2007 | Stubbs |
| 7,220,221 B2 | 5/2007 | Mosimann et al. |
| 7,223,213 B2 | 5/2007 | Golesh |
| 7,223,214 B2 | 5/2007 | Chen |
| 7,223,215 B2 | 5/2007 | Bastyr |
| 7,223,216 B1 | 5/2007 | McBride |
| 7,226,402 B1 | 6/2007 | Joya |
| 7,228,601 B2 | 6/2007 | Thompson |
| 7,229,391 B2 | 6/2007 | Francis |
| 7,232,404 B2 | 6/2007 | Nelson |
| 7,238,143 B1 | 7/2007 | Sokolovos |
| 7,238,147 B2 | 7/2007 | Mills et al. |
| 7,244,217 B2 | 7/2007 | Rodgers, Jr. |
| 7,247,128 B2 | 7/2007 | Oga |
| 7,249,540 B1 | 7/2007 | Hacker et al. |
| 7,250,021 B2 | 7/2007 | Leight |
| 7,250,022 B2 | 7/2007 | Dalebout |
| 7,255,665 B2 | 8/2007 | Ish, III |
| 7,255,666 B2 | 8/2007 | Cardenas |
| 7,261,678 B2 | 8/2007 | Liou |
| 7,264,554 B2 | 9/2007 | Bentley |
| 7,264,578 B1 | 9/2007 | Krull |
| 7,270,628 B2 | 9/2007 | Campanaro |
| 7,276,017 B2 | 10/2007 | Lin |
| 7,276,018 B2 | 10/2007 | Studdard |
| 7,278,955 B2 | 10/2007 | Giannelli et al. |
| 7,278,958 B2 | 10/2007 | Morgan |
| 7,278,966 B2 | 10/2007 | Hjelt et al. |
| 7,282,016 B2 | 10/2007 | Simonson |
| 7,284,466 B1 | 10/2007 | Ho |
| 7,285,075 B2 | 10/2007 | Cutler et al. |
| 7,288,053 B2 | 10/2007 | Endelman et al. |
| 7,290,760 B1 | 11/2007 | Lindsay |
| 7,291,096 B2 | 11/2007 | Ho |
| 7,291,098 B1 | 11/2007 | Krull |
| 7,294,095 B2 | 11/2007 | Charnitski |
| 7,294,100 B2 | 11/2007 | Bull |
| 7,299,720 B1 | 11/2007 | Schultz et al. |
| 7,300,390 B1 | 11/2007 | Krull |
| 7,300,392 B1 | 11/2007 | Curran |
| 7,309,303 B1 | 12/2007 | Proctor |
| 7,311,640 B2 | 12/2007 | Baatz |
| 7,311,644 B2 | 12/2007 | Hale |
| 7,314,438 B1 | 1/2008 | Clark et al. |
| 7,318,810 B1 | 1/2008 | Benson |
| 7,322,219 B2 | 1/2008 | Armstrong et al. |
| 7,322,906 B2 | 1/2008 | Webber |
| 7,322,907 B2 | 1/2008 | Bowser |
| 7,322,909 B1 | 1/2008 | Loccarini |
| 7,329,212 B2 | 2/2008 | Roque |
| 7,331,908 B2 | 2/2008 | Olsen |
| 7,331,911 B2 | 2/2008 | Webber et al. |
| 7,335,139 B2 | 2/2008 | Bartholomew et al. |
| 7,335,140 B2 | 2/2008 | Webber et al. |
| 7,335,141 B2 | 2/2008 | Piane, Jr. |
| 7,335,142 B2 | 2/2008 | Towley, III et al. |
| 7,341,545 B2 | 3/2008 | Cao |
| 7,344,481 B2 | 3/2008 | Watterson et al. |
| 7,344,488 B2 | 3/2008 | Casey et al. |
| 7,351,187 B2 | 4/2008 | Seliber |
| 7,357,758 B2 | 4/2008 | Polk, III |
| 7,361,123 B1 | 4/2008 | Krull |
| 7,361,125 B2 | 4/2008 | Webber et al. |
| 7,361,127 B2 | 4/2008 | Tremayne |
| 7,364,538 B2 | 4/2008 | Aucamp |
| 7,367,926 B2 | 5/2008 | Clark |
| 7,367,927 B2 | 5/2008 | Krull |
| 7,370,498 B1 | 5/2008 | Miao |
| 7,374,519 B2 | 5/2008 | Naidus |
| 7,374,522 B2 | 5/2008 | Arnold |
| 7,377,882 B2 | 5/2008 | Watterson |
| 7,377,886 B2 | 5/2008 | Wu |
| 7,381,161 B2 | 6/2008 | Ellis |
| 7,381,167 B2 | 6/2008 | Duhamel |
| 7,384,013 B2 | 6/2008 | Yen |
| 7,384,209 B2 | 6/2008 | Muders et al. |

(56) References Cited

U.S. PATENT DOCUMENTS

| | | |
|---|---|---|
| 7,384,381 B2 | 6/2008 | Webber et al. |
| 7,387,597 B2 | 6/2008 | Krull |
| 7,387,867 B2 | 6/2008 | Hasegawa et al. |
| 7,396,319 B1 | 7/2008 | Ellis |
| 7,413,056 B2 | 8/2008 | Gonzi et al. |
| 7,413,065 B2 | 8/2008 | Gauthier |
| 7,413,530 B2 | 8/2008 | Warner et al. |
| 7,413,532 B1 | 8/2008 | Monsrud et al. |
| 7,413,533 B2 | 8/2008 | Lin |
| 7,425,188 B2 | 9/2008 | Ercanbrack |
| 7,429,235 B2 | 9/2008 | Lin |
| 7,429,236 B2 | 9/2008 | Dalebout et al. |
| 7,435,202 B2 | 10/2008 | Daly et al. |
| 7,438,673 B1 | 10/2008 | Jones |
| 7,448,823 B2 | 11/2008 | Silva |
| 7,452,311 B2 | 11/2008 | Barnes |
| 7,455,622 B2 | 11/2008 | Watterson |
| 7,455,626 B2 | 11/2008 | Trevino et al. |
| 7,455,633 B2 | 11/2008 | Brown et al. |
| 7,462,135 B2 | 12/2008 | Lo |
| 7,462,141 B1 | 12/2008 | Raboin et al. |
| 7,468,025 B2 | 12/2008 | Hauser et al. |
| 7,470,219 B2 | 12/2008 | Larson |
| 7,473,211 B2 | 1/2009 | Lee |
| 7,475,641 B2 | 1/2009 | Jin |
| 7,475,900 B2 | 1/2009 | Cheng |
| 7,476,182 B2 | 1/2009 | Denisco |
| 7,476,186 B1 | 1/2009 | Steffee |
| 7,478,794 B1 | 1/2009 | Gohlke et al. |
| 7,482,050 B2 | 1/2009 | Olson |
| 7,485,076 B2 | 2/2009 | Lee |
| 7,485,077 B2 | 2/2009 | Chen |
| 7,485,079 B2 | 2/2009 | Brown et al. |
| 7,488,277 B1 | 2/2009 | Knapp |
| 7,491,155 B2 | 2/2009 | Fenelon et al. |
| 7,491,157 B1 | 2/2009 | Lin |
| 7,491,159 B2 | 2/2009 | Patterson |
| 7,494,450 B2 | 2/2009 | Solomon |
| D588,655 S | 3/2009 | Utykanski |
| 7,497,814 B1 | 3/2009 | Krull |
| 7,503,883 B2 | 3/2009 | Madden |
| 7,507,186 B2 | 3/2009 | Stearns |
| 7,507,189 B2 | 3/2009 | Krull |
| 7,510,508 B2 | 3/2009 | Santomassimo et al. |
| 7,510,509 B2 | 3/2009 | Hickman |
| 7,517,303 B2 | 4/2009 | Crawford et al. |
| 7,517,304 B1 | 4/2009 | Swanson et al. |
| 7,520,845 B2 | 4/2009 | Towley, III et al. |
| 7,524,272 B2 | 4/2009 | Bruck et al. |
| 7,534,200 B1 | 5/2009 | Martinez |
| 7,537,546 B2 | 5/2009 | Watterson et al. |
| 7,537,549 B2 | 5/2009 | Nelson et al. |
| 7,537,550 B1 | 5/2009 | Krull |
| 7,537,551 B2 | 5/2009 | Steffee |
| 7,537,552 B2 | 5/2009 | Dalebout et al. |
| 7,540,828 B2 | 6/2009 | Watterson et al. |
| 7,540,829 B1 | 6/2009 | Lin |
| 7,540,832 B2 | 6/2009 | Krull |
| 7,549,947 B2 | 6/2009 | Hickman |
| 7,549,949 B2 | 6/2009 | Webber et al. |
| 7,553,260 B2 | 6/2009 | Piaget et al. |
| 7,553,262 B2 | 6/2009 | Piane, Jr. |
| 7,553,264 B2 | 6/2009 | Carter |
| 7,553,267 B1 | 6/2009 | Hauser |
| 7,556,590 B2 | 7/2009 | Watterson et al. |
| 7,559,879 B2 | 7/2009 | Anderson et al. |
| 7,563,203 B2 | 7/2009 | Dalebout et al. |
| 7,563,208 B1 | 7/2009 | Chen |
| 7,563,209 B2 | 7/2009 | Webber et al. |
| 7,563,213 B2 | 7/2009 | Grant |
| 7,563,214 B2 | 7/2009 | Webber et al. |
| 7,569,004 B2 | 8/2009 | Kolomeir |
| 7,569,005 B2 | 8/2009 | Geeting |
| 7,571,517 B2 | 8/2009 | Smith et al. |
| 7,575,536 B1 | 8/2009 | Hickman |
| 7,575,537 B2 | 8/2009 | Ellis |
| 7,575,538 B1 | 8/2009 | Clark |
| 7,578,771 B1 | 8/2009 | Towley, III et al. |
| 7,578,772 B2 | 8/2009 | Lippitt |
| 7,584,673 B2 | 9/2009 | Shimizu |
| 7,585,251 B2 | 9/2009 | Doody, Jr. et al. |
| 7,585,254 B2 | 9/2009 | Vittone |
| 7,585,262 B1 | 9/2009 | Vayntraub |
| 7,585,263 B2 | 9/2009 | Brown et al. |
| 7,588,520 B2 | 9/2009 | Nalley |
| 7,591,763 B1 | 9/2009 | Fucci |
| 7,591,773 B2 | 9/2009 | Weir |
| 7,594,873 B2 | 9/2009 | Terao et al. |
| 7,594,880 B2 | 9/2009 | Webber |
| 7,594,881 B2 | 9/2009 | Shifferaw |
| 7,597,656 B2 | 10/2009 | Trees |
| 7,601,101 B2 | 10/2009 | Jackson et al. |
| 7,601,105 B1 | 10/2009 | Gipson, III et al. |
| 7,601,187 B2 | 10/2009 | Webber |
| 7,604,572 B2 | 10/2009 | Stanford |
| 7,604,573 B2 | 10/2009 | Dalebout |
| 7,604,576 B2 | 10/2009 | Drechsler |
| 7,604,577 B2 | 10/2009 | Lin |
| 7,604,578 B2 | 10/2009 | Liu |
| 7,608,020 B2 | 10/2009 | Mason |
| 7,608,021 B1 | 10/2009 | Nalley |
| 7,608,023 B2 | 10/2009 | Casagrande |
| 7,608,024 B2 | 10/2009 | Sechrest et al. |
| 7,608,028 B2 | 10/2009 | Pertegaz-Esteban |
| D604,373 S | 11/2009 | Dalebout |
| 7,611,445 B2 | 11/2009 | Brown et al. |
| 7,611,448 B2 | 11/2009 | Schiff |
| 7,611,450 B2 | 11/2009 | Mancini |
| 7,614,981 B2 | 11/2009 | Cao |
| 7,614,984 B1 | 11/2009 | Krull |
| 7,618,350 B2 | 11/2009 | Dalebout et al. |
| 7,618,357 B2 | 11/2009 | Dalebout |
| 7,621,847 B2 | 11/2009 | Lamle |
| 7,621,850 B2 | 11/2009 | Piaget et al. |
| 7,621,855 B1 | 11/2009 | Krull |
| 7,621,856 B1 | 11/2009 | Keith |
| 7,621,858 B2 | 11/2009 | Sheron |
| 7,624,956 B2 | 12/2009 | Steigert et al. |
| 7,624,967 B1 | 12/2009 | Doebler et al. |
| 7,625,033 B2 | 12/2009 | Michelau et al. |
| 7,625,314 B2 | 12/2009 | Ungari |
| 7,625,315 B2 | 12/2009 | Hickman |
| 7,625,319 B2 | 12/2009 | Kang et al. |
| 7,625,321 B2 | 12/2009 | Simonson et al. |
| 7,625,322 B1 | 12/2009 | Krull |
| 7,625,323 B1 | 12/2009 | Lin |
| 7,628,730 B1 | 12/2009 | Watterson et al. |
| 7,628,737 B2 | 12/2009 | Kowallis et al. |
| 7,628,743 B1 | 12/2009 | Flentye et al. |
| 7,632,221 B1 | 12/2009 | Kolander |
| 7,637,847 B1 | 12/2009 | Hickman |
| 7,637,855 B2 | 12/2009 | Bizzell |
| 7,641,598 B2 | 1/2010 | Rodgers, Jr. |
| 7,645,212 B2 | 1/2010 | Ashby et al. |
| 7,645,213 B2 | 1/2010 | Watterson |
| 7,645,215 B2 | 1/2010 | Gordon |
| 7,645,216 B2 | 1/2010 | Edeker |
| 7,645,218 B2 | 1/2010 | Potok et al. |
| 7,645,221 B1 | 1/2010 | Curry |
| 7,648,446 B2 | 1/2010 | Chiles et al. |
| 7,651,442 B2 | 1/2010 | Carlson |
| 7,651,450 B2 | 1/2010 | Wehrell |
| 7,654,940 B2 | 2/2010 | Webber et al. |
| 7,654,941 B2 | 2/2010 | Lacher |
| 7,658,698 B2 | 2/2010 | Pacheco et al. |
| 7,662,075 B2 | 2/2010 | Isom |
| 7,666,123 B2 | 2/2010 | Giannelli |
| 7,670,269 B2 | 3/2010 | Webber et al. |
| 7,670,270 B2 | 3/2010 | Alessandri et al. |
| 7,674,185 B2 | 3/2010 | Omidi |
| 7,674,205 B2 | 3/2010 | Dalebout et al. |
| 7,674,216 B1 | 3/2010 | Bolling |
| 7,678,033 B2 | 3/2010 | Tyree |
| 7,682,287 B1 | 3/2010 | Hsieh |

(56) References Cited

U.S. PATENT DOCUMENTS

| | | |
|---|---|---|
| 7,691,033 B2 | 4/2010 | Rolli |
| 7,691,041 B2 | 4/2010 | Abdo |
| 7,691,042 B2 | 4/2010 | Pandozy |
| 7,695,409 B2 | 4/2010 | Helie et al. |
| 7,695,414 B2 | 4/2010 | Tiahrt |
| 7,704,195 B2 | 4/2010 | Alessandri et al. |
| 7,704,197 B2 | 4/2010 | Yu |
| 7,708,668 B2 | 5/2010 | Rodgers, Jr. |
| 7,708,672 B2 | 5/2010 | Gibson et al. |
| 7,713,171 B1 | 5/2010 | Hickman |
| 7,713,172 B2 | 5/2010 | Watterson et al. |
| 7,713,180 B2 | 5/2010 | Wickens |
| 7,717,827 B2 | 5/2010 | Kurunmäki et al. |
| 7,717,828 B2 | 5/2010 | Simonson et al. |
| 7,717,832 B2 | 5/2010 | Webber et al. |
| 7,717,833 B1 | 5/2010 | Nelson et al. |
| 7,722,509 B2 | 5/2010 | Eder |
| 7,722,513 B2 | 5/2010 | Habing |
| 7,730,588 B1 | 6/2010 | Bernier |
| 7,736,279 B2 | 6/2010 | Dalebout et al. |
| 7,736,283 B2 | 6/2010 | Webb |
| 7,736,286 B2 | 6/2010 | Panaiotov |
| 7,740,563 B2 | 6/2010 | Dalebout et al. |
| 7,740,568 B2 | 6/2010 | Webb |
| 7,740,570 B2 | 6/2010 | Winston |
| 7,749,140 B1 | 7/2010 | Lindemeier et al. |
| 7,749,144 B2 | 7/2010 | Hammer |
| 7,758,469 B2 | 7/2010 | Dyer et al. |
| 7,758,477 B2 | 7/2010 | Prenatt |
| 7,758,478 B2 | 7/2010 | Golesh et al. |
| 7,762,932 B2 | 7/2010 | Hetrick |
| 7,762,934 B1 | 7/2010 | Munson, Jr. et al. |
| 7,762,935 B2 | 7/2010 | Doble |
| 7,764,641 B2 | 7/2010 | Pelton et al. |
| 7,766,793 B2 | 8/2010 | Hashimoto |
| 7,766,797 B2 | 8/2010 | Dalebout |
| 7,766,802 B2 | 8/2010 | Webber et al. |
| 7,771,319 B1 | 8/2010 | Lannon |
| 7,771,320 B2 | 8/2010 | Riley et al. |
| 7,771,325 B2 | 8/2010 | Baker |
| 7,771,329 B2 | 8/2010 | Dalebout et al. |
| 7,771,330 B2 | 8/2010 | Towley |
| 7,775,936 B2 | 8/2010 | Wilkinson |
| 7,775,940 B2 | 8/2010 | Dalebout |
| 7,775,943 B2 | 8/2010 | Vittone |
| 7,775,945 B2 | 8/2010 | Smith |
| 7,775,949 B2 | 8/2010 | Bowser |
| 7,775,952 B1 | 8/2010 | Curran et al. |
| 7,775,953 B2 | 8/2010 | Wang |
| 7,780,578 B2 | 8/2010 | Packham |
| 7,780,583 B2 | 8/2010 | Brown |
| 7,780,585 B1 | 8/2010 | Rivas |
| 7,789,800 B1 | 9/2010 | Watterson |
| 7,789,806 B2 | 9/2010 | Yang |
| 7,789,816 B2 | 9/2010 | Krietzman |
| 7,794,371 B2 | 9/2010 | Webber et al. |
| 7,798,946 B2 | 9/2010 | Dalebout et al. |
| 7,803,096 B2 | 9/2010 | Mehta |
| 7,806,589 B2 | 10/2010 | Tashman |
| 7,806,815 B2 | 10/2010 | Fernandez |
| 7,811,202 B2 | 10/2010 | Planke |
| 7,811,213 B2 | 10/2010 | Chen |
| 7,815,548 B2 | 10/2010 | Barre et al. |
| 7,815,549 B2 | 10/2010 | Crawford et al. |
| 7,815,550 B2 | 10/2010 | Watterson et al. |
| 7,815,552 B2 | 10/2010 | Dibble et al. |
| 7,815,554 B2 | 10/2010 | Gibson et al. |
| 7,819,784 B1 | 10/2010 | Caswell et al. |
| 7,819,785 B2 | 10/2010 | Maiaro et al. |
| 7,828,703 B1 | 11/2010 | Boesch |
| 7,833,135 B2 | 11/2010 | Radow |
| 7,833,138 B1 | 11/2010 | Fulks |
| 7,833,141 B2 | 11/2010 | Kulka |
| 7,837,598 B1 | 11/2010 | Boozel, Jr. |
| 7,837,602 B1 | 11/2010 | Drybread |
| 7,837,603 B1 | 11/2010 | Carnell, Sr. |
| 7,841,971 B2 | 11/2010 | Smith |
| 7,841,973 B2 | 11/2010 | Trancart |
| 7,842,038 B2 | 11/2010 | Haddock et al. |
| 7,850,584 B2 | 12/2010 | Uygan |
| 7,857,731 B2 | 12/2010 | Hickman |
| 7,857,736 B2 | 12/2010 | Merrithew et al. |
| 7,862,475 B2 | 1/2011 | Watterson |
| 7,862,478 B2 | 1/2011 | Watterson |
| 7,862,483 B2 | 1/2011 | Hendrickson et al. |
| 7,862,486 B1 | 1/2011 | Watson |
| 7,862,487 B2 | 1/2011 | Olson |
| 7,862,489 B2 | 1/2011 | Savšek et al. |
| 7,867,153 B2 | 1/2011 | Roman |
| 7,871,355 B2 | 1/2011 | Yeh |
| 7,871,357 B2 | 1/2011 | Gibson et al. |
| 7,874,957 B2 | 1/2011 | Hurwitz et al. |
| 7,874,961 B2 | 1/2011 | McKee et al. |
| 7,874,971 B2 | 1/2011 | Reyes |
| 7,878,950 B1 | 2/2011 | Bastian |
| 7,878,953 B2 | 2/2011 | Webber et al. |
| 7,883,445 B2 | 2/2011 | Olrik et al. |
| 7,887,468 B2 | 2/2011 | Ross et al. |
| 7,887,469 B1 | 2/2011 | Chen |
| 7,887,470 B2 | 2/2011 | Chen |
| 7,887,471 B2 | 2/2011 | Mcsorley |
| 7,892,149 B2 | 2/2011 | Wu |
| 7,892,150 B1 | 2/2011 | Colley |
| 7,892,155 B2 | 2/2011 | Pearson et al. |
| 7,892,159 B2 | 2/2011 | McVay et al. |
| D635,207 S | 3/2011 | Dalebout |
| 7,896,782 B2 | 3/2011 | Tamari |
| 7,900,324 B2 | 3/2011 | Ginocchio |
| 7,901,324 B2 | 3/2011 | Kodama |
| 7,901,330 B2 | 3/2011 | Dalebout |
| 7,901,335 B2 | 3/2011 | Webber et al. |
| 7,905,819 B2 | 3/2011 | Alessandri et al. |
| 7,909,740 B2 | 3/2011 | Dalebout |
| 7,909,741 B2 | 3/2011 | Kim et al. |
| 7,909,742 B2 | 3/2011 | Ish, III et al. |
| 7,909,743 B1 | 3/2011 | Webber |
| 7,909,745 B2 | 3/2011 | Mills et al. |
| 7,918,769 B2 | 4/2011 | Lamarque |
| 7,922,621 B1 | 4/2011 | Hamada et al. |
| 7,922,631 B2 | 4/2011 | Ish, III |
| 7,922,632 B2 | 4/2011 | Chou |
| 7,922,633 B2 | 4/2011 | Januszek |
| 7,922,635 B2 | 4/2011 | Lull et al. |
| 7,927,257 B2 | 4/2011 | Patel |
| 7,931,563 B2 | 4/2011 | Shaw et al. |
| 7,931,570 B2 | 4/2011 | Hoffman |
| 7,935,026 B2 | 5/2011 | Mcsorley |
| 7,935,032 B1 | 5/2011 | Jackson |
| 7,935,038 B2 | 5/2011 | Tyree |
| 7,938,760 B1 | 5/2011 | Webber et al. |
| 7,938,761 B2 | 5/2011 | Simonson |
| 7,942,788 B2 | 5/2011 | Wu |
| 7,942,793 B2 | 5/2011 | Mills et al. |
| 7,946,968 B2 | 5/2011 | Kjellberg |
| 7,955,235 B2 | 6/2011 | Keiser |
| 7,963,890 B2 | 6/2011 | Webber et al. |
| 7,963,892 B2 | 6/2011 | Poblete Castro et al. |
| 7,967,734 B1 | 6/2011 | Damian |
| 7,976,440 B2 | 7/2011 | Webber et al. |
| 7,976,443 B2 | 7/2011 | Krull |
| 7,976,445 B2 | 7/2011 | Lalaoua |
| 7,980,996 B2 | 7/2011 | Hickman |
| 7,981,000 B2 | 7/2011 | Watterson |
| 7,981,010 B1 | 7/2011 | Webber et al. |
| 7,981,011 B1 | 7/2011 | Batca |
| 7,981,012 B1 | 7/2011 | Krull |
| 7,981,013 B1 | 7/2011 | Krull |
| 7,985,164 B2 | 7/2011 | Ashby |
| 7,985,167 B2 | 7/2011 | Nizam |
| 7,988,598 B2 | 8/2011 | Trzecieski |
| 7,988,600 B2 | 8/2011 | Rodgers, Jr. |
| 7,988,604 B2 | 8/2011 | Barnett |
| 7,988,605 B1 | 8/2011 | Wyeroski |
| 7,993,251 B1 | 8/2011 | Webber et al. |

(56) References Cited

U.S. PATENT DOCUMENTS

| | | | |
|---|---|---|---|
| 7,998,036 B2 | 8/2011 | Ish, III | |
| 7,998,038 B2 | 8/2011 | Keiser | |
| 7,998,042 B2 | 8/2011 | Bowser et al. | |
| 8,001,472 B2 | 8/2011 | Gilley et al. | |
| 8,002,678 B1 | 8/2011 | Krull | |
| 8,006,711 B2 | 8/2011 | Pietrzak et al. | |
| 8,007,409 B2 | 8/2011 | Elllis | |
| 8,007,413 B1 | 8/2011 | Wu | |
| 8,007,415 B1 | 8/2011 | Lundquist | |
| 8,007,416 B2 | 8/2011 | Arlie | |
| 8,007,422 B2 | 8/2011 | Zaccherini | |
| 8,012,071 B2 | 9/2011 | Grisdale | |
| 8,012,073 B2 | 9/2011 | Barnett | |
| 8,021,277 B2 | 9/2011 | Baudhuin | |
| 8,021,285 B2 | 9/2011 | Kushnir | |
| 8,025,608 B2 | 9/2011 | Popescu | |
| 8,025,613 B1 | 9/2011 | Wang | |
| 8,029,415 B2 | 10/2011 | Ashby et al. | |
| 8,029,425 B2 | 10/2011 | Bronston et al. | |
| 8,033,960 B1 | 10/2011 | Dalebout et al. | |
| 8,033,965 B1 | 10/2011 | Krull | |
| 8,033,967 B2 | 10/2011 | Canali | |
| 8,043,198 B2 | 10/2011 | Zhou | |
| 8,047,970 B2 | 11/2011 | Nalley | |
| 8,052,584 B2 | 11/2011 | Keiser | |
| 8,056,687 B2 | 11/2011 | Golden et al. | |
| 8,057,361 B2 | 11/2011 | McBride et al. | |
| 8,057,367 B2 | 11/2011 | Giannelli et al. | |
| 8,057,368 B1 | 11/2011 | Lyszczarz | |
| D650,451 S | 12/2011 | Olson | |
| 8,070,657 B2 | 12/2011 | Loach | |
| 8,070,658 B2 | 12/2011 | Giannelli et al. | |
| 8,072,902 B2 | 12/2011 | Moon | |
| 8,075,453 B1 * | 12/2011 | Wilkinson | A63B 22/0005 482/51 |
| 8,079,273 B2 | 12/2011 | Svenberg | |
| 8,079,941 B2 | 12/2011 | Nortje | |
| D652,877 S | 1/2012 | Dalebout | |
| 8,092,351 B1 | 1/2012 | Rodgers, Jr. | |
| 8,096,926 B1 | 1/2012 | Batca | |
| 8,103,379 B2 | 1/2012 | Biba et al. | |
| 8,104,987 B2 | 1/2012 | Johnson | |
| 8,106,563 B2 | 1/2012 | Ritchey | |
| 8,109,864 B2 | 2/2012 | Tseng | |
| 8,111,166 B2 | 2/2012 | Flexer et al. | |
| 8,113,994 B2 | 2/2012 | Piaget et al. | |
| 8,128,537 B2 | 3/2012 | Signorile et al. | |
| 8,142,370 B2 | 3/2012 | Weinberg et al. | |
| 8,147,386 B2 | 4/2012 | Farnsworth et al. | |
| 8,152,702 B2 | 4/2012 | Pacheco | |
| 8,157,708 B2 | 4/2012 | Daly | |
| D659,775 S | 5/2012 | Olson | |
| D659,777 S | 5/2012 | Watterson | |
| D660,383 S | 5/2012 | Watterson | |
| 8,167,899 B2 | 5/2012 | Justis et al. | |
| 8,172,729 B2 | 5/2012 | Ellis | |
| 8,173,087 B2 | 5/2012 | Wei et al. | |
| 8,177,693 B2 | 5/2012 | Webber et al. | |
| 8,182,399 B2 | 5/2012 | Davis et al. | |
| 8,192,332 B2 | 6/2012 | Baker et al. | |
| 8,192,337 B2 | 6/2012 | Birch | |
| 8,197,392 B2 | 6/2012 | Silverman et al. | |
| 8,200,323 B2 | 6/2012 | Dibenedetto et al. | |
| 8,206,274 B2 | 6/2012 | Svenberg et al. | |
| D664,613 S | 7/2012 | Dalebout | |
| 8,210,995 B2 | 7/2012 | Reyes | |
| 8,212,445 B2 | 7/2012 | Ritchey | |
| 8,215,886 B2 | 7/2012 | Campbell | |
| 8,221,295 B2 | 7/2012 | Wilkins | |
| 8,235,724 B2 | 8/2012 | Gilley et al. | |
| 8,235,876 B2 | 8/2012 | Reyes | |
| 8,241,187 B2 | 8/2012 | Moon et al. | |
| 8,249,714 B1 | 8/2012 | Hartman et al. | |
| 8,251,874 B2 | 8/2012 | Ashby | |
| 8,251,877 B2 | 8/2012 | Rasmussen et al. | |
| 8,257,232 B2 | 9/2012 | Albert | |
| 8,262,546 B1 | 9/2012 | Lashinske | |
| 8,272,996 B2 | 9/2012 | Weier | |
| 8,286,954 B2 | 10/2012 | Zheng | |
| 8,298,123 B2 | 10/2012 | Hickman | |
| 8,298,125 B2 | 10/2012 | Colledge et al. | |
| D671,177 S | 11/2012 | Sip | |
| D671,178 S | 11/2012 | Sip | |
| 8,303,472 B2 | 11/2012 | Bowser | |
| 8,308,618 B2 | 11/2012 | Bayerlein | |
| 8,308,620 B2 | 11/2012 | Lyszczarz | |
| 8,309,870 B2 | 11/2012 | Peterson et al. | |
| 8,315,636 B2 | 11/2012 | Moon et al. | |
| 8,317,659 B2 | 11/2012 | Woodson | |
| 8,323,156 B2 | 12/2012 | Ozawa et al. | |
| 8,323,157 B2 | 12/2012 | Campanaro et al. | |
| 8,323,159 B2 | 12/2012 | Perry | |
| D673,626 S | 1/2013 | Olson | |
| 8,348,811 B2 | 1/2013 | Kamins | |
| 8,359,954 B2 | 1/2013 | Johnson et al. | |
| 8,360,935 B2 | 1/2013 | Olsen et al. | |
| 8,376,911 B2 | 2/2013 | Ogg et al. | |
| 8,394,004 B2 | 3/2013 | Towley, III | |
| 8,398,529 B2 | 3/2013 | Ellis | |
| 8,429,223 B2 | 4/2013 | Gilley et al. | |
| 8,444,537 B1 | 5/2013 | Santoro | |
| 8,454,437 B2 | 6/2013 | Dugan | |
| 8,454,483 B1 | 6/2013 | Bradley et al. | |
| 8,470,190 B2 | 6/2013 | Jeanne et al. | |
| 8,475,338 B2 | 7/2013 | Greenhill et al. | |
| 8,485,576 B2 | 7/2013 | Melville et al. | |
| 8,485,946 B2 | 7/2013 | Ross et al. | |
| 8,485,947 B2 | 7/2013 | Nizam | |
| 8,485,950 B2 | 7/2013 | Adams | |
| 8,485,953 B2 | 7/2013 | Chou | |
| 8,485,996 B2 | 7/2013 | Bluman | |
| 8,500,607 B2 | 8/2013 | Vittone | |
| 8,500,608 B1 | 8/2013 | Bonomi | |
| 8,506,370 B2 | 8/2013 | Homsi | |
| 8,506,459 B2 | 8/2013 | Cassidy et al. | |
| 8,512,212 B2 | 8/2013 | Ish, III | |
| 8,517,895 B2 | 8/2013 | Shalev | |
| 8,517,899 B2 | 8/2013 | Zhou | |
| 8,523,743 B1 | 9/2013 | Miles et al. | |
| 8,523,789 B2 | 9/2013 | Keiser | |
| 8,529,414 B2 | 9/2013 | Hobson | |
| 8,529,415 B2 | 9/2013 | Svenberg | |
| 8,535,204 B2 | 9/2013 | Stacey | |
| 8,540,607 B2 | 9/2013 | Kissel et al. | |
| 8,550,964 B2 | 10/2013 | Ish, III et al. | |
| 8,556,216 B2 | 10/2013 | Bandera | |
| 8,556,780 B2 | 10/2013 | Chen | |
| 8,562,496 B2 | 10/2013 | Webber et al. | |
| 8,568,279 B2 | 10/2013 | Golesh | |
| 8,568,280 B2 | 10/2013 | Mendoza | |
| 8,568,281 B2 | 10/2013 | Beaulieu et al. | |
| 8,572,764 B2 | 11/2013 | Thellmann | |
| 8,572,820 B2 | 11/2013 | Richards | |
| 8,573,572 B2 | 11/2013 | Bowen et al. | |
| 8,585,561 B2 | 11/2013 | Watt et al. | |
| 8,588,476 B1 | 11/2013 | Spicola, Jr. | |
| 8,590,120 B2 | 11/2013 | Sakai | |
| 8,591,386 B2 | 11/2013 | Meyer | |
| 8,591,387 B2 | 11/2013 | Fife | |
| 8,602,951 B2 | 12/2013 | Morris | |
| 8,607,562 B2 | 12/2013 | Browne | |
| 8,608,624 B2 | 12/2013 | Shabodyash | |
| 8,613,689 B2 | 12/2013 | Dyer et al. | |
| 8,631,544 B1 | 1/2014 | Shotey et al. | |
| 8,647,239 B1 | 2/2014 | Sokolovas | |
| 8,668,630 B2 | 3/2014 | Towley, III | |
| 8,678,897 B2 | 3/2014 | Englert et al. | |
| 8,690,578 B1 | 4/2014 | Nusbaum et al. | |
| 8,690,735 B2 | 4/2014 | Watterson et al. | |
| 8,690,740 B2 | 4/2014 | Yu | |
| 8,696,527 B2 | 4/2014 | Wu | |
| 8,702,574 B2 | 4/2014 | Abranchess | |
| 8,708,870 B2 | 4/2014 | Nalley | |
| 8,708,872 B2 | 4/2014 | Giannelli et al. | |

(56) References Cited

U.S. PATENT DOCUMENTS

| | | |
|---|---|---|
| 8,715,140 B1 | 5/2014 | Gertz |
| 8,715,143 B2 | 5/2014 | Svenberg |
| 8,721,507 B2 | 5/2014 | Blancher |
| 8,734,302 B2 | 5/2014 | Hsieh |
| 8,734,304 B2 | 5/2014 | Webber et al. |
| 8,734,308 B1 | 5/2014 | Joslin |
| D707,763 S | 6/2014 | Cutler |
| 8,740,753 B2 | 6/2014 | Olson et al. |
| 8,747,285 B2 | 6/2014 | Hof |
| 8,758,201 B2 | 6/2014 | Ashby et al. |
| 8,764,609 B1 | 7/2014 | Elahmadie |
| 8,771,153 B2 | 7/2014 | Dalebout et al. |
| 8,771,154 B2 | 7/2014 | Fedriga |
| 8,777,820 B2 | 7/2014 | Lo |
| 8,777,822 B2 | 7/2014 | Agostini |
| 8,784,270 B2 | 7/2014 | Watterson |
| 8,784,275 B2 | 7/2014 | Mikan et al. |
| 8,784,278 B2 | 7/2014 | Flake |
| 8,784,286 B2 | 7/2014 | Reyes |
| 8,801,581 B2 | 8/2014 | Lai et al. |
| 8,808,148 B2 | 8/2014 | Watterson |
| 8,814,754 B2 | 8/2014 | Weast et al. |
| 8,814,762 B2 | 8/2014 | Butler |
| 8,815,189 B2 | 8/2014 | Arnold et al. |
| D712,493 S | 9/2014 | Ercanbrack |
| 8,821,354 B1 | 9/2014 | Tabahi |
| 8,821,359 B1 | 9/2014 | Kassel |
| 8,821,870 B2 | 9/2014 | Robinson et al. |
| 8,827,874 B2 | 9/2014 | Nishimura |
| 8,827,879 B2 | 9/2014 | Nicholas |
| 8,840,075 B2 | 9/2014 | Olson |
| 8,840,569 B2 | 9/2014 | Flaction et al. |
| 8,845,493 B2 | 9/2014 | Watterson |
| 8,845,497 B2 | 9/2014 | Turner |
| 8,845,498 B2 | 9/2014 | Webb |
| 8,845,499 B1 | 9/2014 | Boatwright |
| 8,858,397 B2 | 10/2014 | Ishii |
| 8,858,409 B2 | 10/2014 | Trees |
| 8,870,720 B1 | 10/2014 | Webber et al. |
| 8,870,726 B2 | 10/2014 | Watterson et al. |
| 8,876,131 B1 | 11/2014 | Gomes |
| 8,876,668 B2 | 11/2014 | Hendrickson et al. |
| 8,876,674 B2 | 11/2014 | Webb et al. |
| 8,888,660 B1 | 11/2014 | Oteman |
| 8,894,549 B2 | 11/2014 | Colledge |
| 8,894,555 B2 | 11/2014 | Olson |
| 8,911,330 B2 | 12/2014 | Watterson |
| 8,917,273 B2 | 12/2014 | Hoebel |
| 8,920,288 B2 | 12/2014 | Dalebout |
| 8,920,291 B2 | 12/2014 | Chen et al. |
| 8,920,347 B2 | 12/2014 | Bayerlein |
| 8,926,479 B2 | 1/2015 | Chen et al. |
| 8,932,188 B2 | 1/2015 | Svenberg |
| 8,939,831 B2 | 1/2015 | Dugan |
| 8,956,290 B2 | 2/2015 | Gilley et al. |
| 8,968,155 B2 | 3/2015 | Bird |
| 8,968,162 B2 | 3/2015 | Jaguan |
| 8,968,164 B2 | 3/2015 | Giannelli |
| 8,979,709 B2 | 3/2015 | Toback et al. |
| 8,986,165 B2 | 3/2015 | Ashby |
| 8,990,045 B2 | 3/2015 | Zhu et al. |
| 8,992,364 B2 | 3/2015 | Law |
| 8,992,387 B2 | 3/2015 | Watterson |
| 8,992,392 B2 | 3/2015 | Giannelli et al. |
| 8,992,393 B2 | 3/2015 | Reyes |
| D726,476 S | 4/2015 | Ercanbrack |
| 9,008,973 B2 | 4/2015 | French |
| 9,010,222 B2 | 4/2015 | Peirce |
| 9,011,156 B2 | 4/2015 | Hallmark |
| 9,011,291 B2 | 4/2015 | Birrell |
| 9,011,299 B2 | 4/2015 | Lien |
| 9,011,301 B2 | 4/2015 | Balandis et al. |
| 9,017,230 B1 | 4/2015 | Pitts |
| 9,022,906 B1 | 5/2015 | Nelson |
| 9,022,907 B2 | 5/2015 | Wang |
| 9,028,368 B2 | 5/2015 | Ashby et al. |
| 9,028,370 B2 | 5/2015 | Watterson |
| 9,028,381 B2 | 5/2015 | Mestemaker |
| 9,038,218 B1 | 5/2015 | Heil et al. |
| 9,038,549 B1 | 5/2015 | Zebarjad |
| 9,039,578 B2 | 5/2015 | Dalebout |
| D731,011 S | 6/2015 | Buchanan |
| 9,044,635 B2 | 6/2015 | Lull |
| 9,050,497 B2 | 6/2015 | Reyes |
| 9,050,498 B2 | 6/2015 | Lu et al. |
| 9,072,930 B2 | 7/2015 | Ashby et al. |
| 9,078,708 B2 | 7/2015 | Haas |
| 9,079,068 B2 | 7/2015 | Muehl |
| 9,114,273 B2 | 8/2015 | Kehoe |
| 9,114,275 B2 | 8/2015 | Lu et al. |
| 9,119,983 B2 | 9/2015 | Rhea |
| 9,119,988 B2 | 9/2015 | Murray |
| 9,123,317 B2 | 9/2015 | Watterson |
| 9,125,620 B2 | 9/2015 | Walke |
| 9,126,071 B2 | 9/2015 | Smith |
| 9,126,072 B2 | 9/2015 | Watterson |
| 9,126,076 B2 | 9/2015 | Liang |
| 9,132,051 B2 | 9/2015 | Heil |
| 9,132,330 B2 | 9/2015 | Brendle |
| 9,135,347 B2 | 9/2015 | Damman et al. |
| 9,138,607 B2 | 9/2015 | Miranda |
| 9,138,612 B2 | 9/2015 | Breaux |
| 9,138,614 B2 | 9/2015 | Lu et al. |
| 9,138,615 B2 | 9/2015 | Olson et al. |
| 9,142,139 B2 | 9/2015 | Watterson |
| 9,144,703 B2 | 9/2015 | Dalebout et al. |
| 9,144,709 B2 | 9/2015 | Reich |
| 9,149,683 B2 | 10/2015 | Smith |
| 9,162,102 B1 | 10/2015 | Eder et al. |
| 9,162,104 B1 | 10/2015 | Lee |
| 9,168,414 B2 | 10/2015 | Liu et al. |
| 9,174,085 B2 | 11/2015 | Foley |
| 9,186,535 B2 | 11/2015 | Ercanbrack |
| 9,186,545 B2 | 11/2015 | Watterson |
| 9,186,552 B1 * | 11/2015 | Deal .................. A63B 21/068 |
| 9,192,800 B1 | 11/2015 | Meyer et al. |
| 9,211,431 B2 | 12/2015 | Hornback et al. |
| 9,227,101 B2 | 1/2016 | Maguire |
| 9,233,272 B2 | 1/2016 | Villani |
| 9,248,329 B2 | 2/2016 | Heideman |
| 9,254,409 B2 | 2/2016 | Dalebout et al. |
| 9,254,416 B2 | 2/2016 | Ashby |
| 9,259,633 B2 | 2/2016 | Meyers |
| 9,265,984 B2 | 2/2016 | Huber |
| 9,272,186 B2 | 3/2016 | Reich |
| 9,278,248 B2 | 3/2016 | Tyger |
| 9,278,249 B2 | 3/2016 | Watterson |
| 9,278,250 B2 | 3/2016 | Buchanan |
| 9,283,429 B2 | 3/2016 | Aragones et al. |
| 9,289,644 B2 | 3/2016 | Carson |
| 9,289,648 B2 | 3/2016 | Watterson |
| 9,292,935 B2 | 3/2016 | Koduri et al. |
| 9,295,302 B1 | 3/2016 | Reed et al. |
| 9,298,886 B2 | 3/2016 | Homsi |
| 9,302,139 B2 | 4/2016 | Habing et al. |
| 9,308,409 B2 | 4/2016 | Beaver et al. |
| 9,308,410 B2 | 4/2016 | Beaver et al. |
| 9,308,417 B2 | 4/2016 | Grundy |
| 9,314,658 B2 | 4/2016 | Kaye |
| 9,314,659 B2 | 4/2016 | Gvoich |
| 9,314,666 B2 | 4/2016 | Canavan et al. |
| 9,320,457 B2 | 4/2016 | Flaction et al. |
| 9,320,935 B1 | 4/2016 | Paris |
| 9,320,938 B1 | 4/2016 | Belmore |
| 9,320,940 B2 | 4/2016 | Rainey |
| 9,327,159 B1 | 5/2016 | Medina |
| 9,333,388 B2 | 5/2016 | Lee et al. |
| 9,339,681 B1 | 5/2016 | Nalley |
| 9,339,682 B2 | 5/2016 | Braier et al. |
| 9,339,683 B2 | 5/2016 | Dilli |
| 9,339,691 B2 | 5/2016 | Brammer |
| 9,339,692 B2 | 5/2016 | Hashish |
| 9,352,181 B2 | 5/2016 | O'Neil |
| 9,352,185 B2 | 5/2016 | Hendrickson et al. |

(56) References Cited

U.S. PATENT DOCUMENTS

| | | |
|---|---|---|
| 9,352,186 B2 | 5/2016 | Watterson |
| 9,358,414 B2 | 6/2016 | Dephouse |
| 9,358,426 B2 | 6/2016 | Aragones et al. |
| 9,364,703 B1 | 6/2016 | Kuka |
| 9,364,706 B2 | 6/2016 | Lo |
| 9,364,712 B2 | 6/2016 | Wu |
| 9,364,714 B2 | 6/2016 | Koduri et al. |
| 9,375,602 B2 | 6/2016 | Krull |
| 9,375,605 B2 | 6/2016 | Tyger |
| 9,378,336 B2 | 6/2016 | Ohnemus et al. |
| 9,381,394 B2 | 7/2016 | Mortensen |
| 9,387,355 B1 | 7/2016 | Joya |
| 9,387,357 B2 | 7/2016 | Mueller |
| 9,387,387 B2 | 7/2016 | Dalebout |
| 9,393,453 B2 | 7/2016 | Watterson |
| 9,403,047 B2 | 8/2016 | Olson |
| 9,403,048 B2 | 8/2016 | Balandis et al. |
| 9,403,051 B2 | 8/2016 | Cutler |
| 9,409,047 B2 | 8/2016 | Kamenskikh |
| 9,409,050 B2 | 8/2016 | Mintz |
| 9,415,257 B2 | 8/2016 | Habing |
| 9,421,416 B2 | 8/2016 | Mortensen |
| 9,427,611 B1 | 8/2016 | Balentine |
| 9,457,219 B2 | 10/2016 | Smith |
| 9,457,220 B2 | 10/2016 | Olson |
| 9,457,222 B2 | 10/2016 | Dalebout |
| 9,460,632 B2 | 10/2016 | Watterson |
| 9,463,345 B2 | 10/2016 | Simonetti |
| 9,463,356 B2 | 10/2016 | Rhea |
| 9,468,792 B2 | 10/2016 | Simonetti |
| 9,468,793 B2 | 10/2016 | Salmon |
| 9,468,794 B2 | 10/2016 | Barton |
| 9,468,798 B2 | 10/2016 | Dalebout |
| 9,474,666 B1 | 10/2016 | Smith |
| 9,480,874 B2 | 11/2016 | Cutler |
| 9,492,704 B2 | 11/2016 | Mortensen et al. |
| 9,498,128 B2 | 11/2016 | Jayalth et al. |
| 9,498,666 B1 | 11/2016 | Boatwright |
| 9,498,668 B2 | 11/2016 | Muller et al. |
| 9,506,528 B2 | 11/2016 | Tucker et al. |
| 9,506,529 B2 | 11/2016 | Tucker et al. |
| 9,511,254 B2 | 12/2016 | Netter |
| 9,517,378 B2 | 12/2016 | Ashby et al. |
| 9,521,901 B2 | 12/2016 | Dalebout |
| 9,526,937 B2 | 12/2016 | Uygan |
| 9,533,187 B2 | 1/2017 | Dalebout |
| 9,539,458 B1 | 1/2017 | Ross |
| 9,539,461 B2 | 1/2017 | Ercanbrack |
| 9,545,540 B1 | 1/2017 | Ercanbrack |
| 9,550,091 B2 | 1/2017 | Emerson |
| 9,555,278 B2 | 1/2017 | Kaye et al. |
| 9,555,280 B2 | 1/2017 | Kaye et al. |
| 9,579,544 B2 | 2/2017 | Watterson |
| 9,586,086 B2 | 3/2017 | Dalebout |
| 9,586,090 B2 | 3/2017 | Watterson |
| 9,593,992 B2 | 3/2017 | Wu |
| 9,604,089 B2 | 3/2017 | Cervone et al. |
| 9,604,092 B2 | 3/2017 | Krull |
| 9,604,099 B2 | 3/2017 | Taylor |
| 9,610,475 B1 | 4/2017 | DeKnock et al. |
| 9,616,274 B2 | 4/2017 | Wehrell |
| 9,616,276 B2 | 4/2017 | Dalebout |
| 9,616,278 B2 | 4/2017 | Olson |
| 9,616,284 B1 | 4/2017 | Aganyan et al. |
| 9,616,292 B2 | 4/2017 | Orfield |
| 9,623,281 B2 | 4/2017 | Hendrickson |
| 9,623,285 B1 | 4/2017 | Ruiz |
| 9,630,048 B2 | 4/2017 | Kaye et al. |
| 9,636,539 B1 | 5/2017 | Brumit |
| 9,636,540 B2 | 5/2017 | Mueller et al. |
| 9,636,567 B2 | 5/2017 | Brammer |
| 9,643,042 B2 | 5/2017 | Madden |
| 9,649,524 B2 | 5/2017 | Giunchi |
| 9,656,115 B2 | 5/2017 | Young |
| 9,656,144 B2 | 5/2017 | Jafarifesharaki |
| 9,656,591 B1 | 5/2017 | Dumenigo et al. |
| 9,665,046 B2 | 5/2017 | Aoto et al. |
| 9,669,261 B2 | 6/2017 | Eder |
| 9,675,836 B2 | 6/2017 | Babon |
| 9,675,839 B2 | 6/2017 | Dalebout |
| 9,682,267 B2 | 6/2017 | Kaye et al. |
| 9,682,307 B2 | 6/2017 | Dalebout |
| 9,687,689 B2 | 6/2017 | Lin |
| 9,692,276 B2 | 6/2017 | Oteman et al. |
| 9,694,234 B2 | 7/2017 | Dalebout et al. |
| 9,694,242 B2 | 7/2017 | Ashby |
| 9,700,752 B1 | 7/2017 | Powers |
| 9,700,753 B1 | 7/2017 | Boatwright |
| 9,707,435 B1 | 7/2017 | Ferlito et al. |
| 9,720,912 B2 | 8/2017 | Morimoto et al. |
| 9,723,381 B2 | 8/2017 | Swanson |
| 9,724,553 B2 | 8/2017 | Kaye et al. |
| 9,724,563 B2 | 8/2017 | Schmidt |
| 9,731,157 B2 | 8/2017 | Loach |
| 9,731,158 B1 | 8/2017 | Lo |
| 9,734,477 B2 | 8/2017 | Weast et al. |
| 9,737,755 B2 | 8/2017 | Dalebout |
| 9,750,454 B2 | 9/2017 | Walke et al. |
| 9,757,605 B2 | 9/2017 | Olson et al. |
| 9,757,611 B1 | 9/2017 | Colburn |
| 9,764,186 B2 | 9/2017 | Dalebout |
| 9,764,188 B1 | 9/2017 | Aganyan et al. |
| 9,767,785 B2 | 9/2017 | Ashby |
| 9,776,032 B2 | 10/2017 | Moran et al. |
| 9,795,818 B2 | 10/2017 | Powell |
| 9,795,819 B2 | 10/2017 | Wehrell |
| 9,795,822 B2 | 10/2017 | Smith et al. |
| 9,795,827 B2 | 10/2017 | Wiener et al. |
| 9,795,855 B2 | 10/2017 | Jafarifesharaki |
| 9,802,072 B2 | 10/2017 | Wehrell |
| 9,802,075 B2 | 10/2017 | Gvoich |
| 9,808,672 B2 | 11/2017 | Dalebout |
| 9,814,920 B1 | 11/2017 | Monterrey |
| 9,814,922 B2 | 11/2017 | Moran et al. |
| 9,814,930 B2 | 11/2017 | Manzke et al. |
| 9,833,654 B1 | 12/2017 | Gant |
| 9,839,804 B2 | 12/2017 | Werner |
| 9,841,077 B2 | 12/2017 | Modrezejewski et al. |
| 9,849,326 B2 | 12/2017 | Smith |
| 9,868,006 B1 | 1/2018 | Epler |
| 9,873,012 B2 | 1/2018 | Huppee et al. |
| 9,878,201 B1 | 1/2018 | Moschel |
| 9,878,210 B2 | 1/2018 | Watterson |
| 9,884,224 B2 | 2/2018 | Spoeth et al. |
| 9,885,575 B2 | 2/2018 | Collin |
| 9,889,334 B2 | 2/2018 | Ashby et al. |
| 9,889,339 B2 | 2/2018 | Douglass |
| 9,895,567 B2 | 2/2018 | Lee |
| 9,895,570 B2 | 2/2018 | Shah |
| 9,895,571 B2 | 2/2018 | Wang |
| 9,901,766 B2 | 2/2018 | Ross |
| 9,901,772 B2 | 2/2018 | Crowley et al. |
| 9,907,396 B1 | 3/2018 | Labrosse et al. |
| 9,919,183 B1 | 3/2018 | Moschel |
| 9,921,726 B1 | 3/2018 | Sculley et al. |
| 9,937,376 B2 | 4/2018 | McInelly |
| 9,937,377 B2 | 4/2018 | McInelly |
| 9,937,378 B2 | 4/2018 | Dalebout |
| 9,937,379 B2 | 4/2018 | Mortensen |
| 9,943,719 B2 | 4/2018 | Smith et al. |
| 9,943,722 B2 | 4/2018 | Dalebout |
| 9,948,037 B2 | 4/2018 | Ashby |
| 9,950,205 B2 | 4/2018 | Simonetti |
| 9,951,904 B2 | 4/2018 | Perez et al. |
| 9,968,816 B2 | 5/2018 | Olson et al. |
| 9,968,821 B2 | 5/2018 | Finlayson et al. |
| 9,968,823 B2 | 5/2018 | Cutler |
| 9,980,465 B2 | 5/2018 | Hayashi |
| 9,993,683 B2 | 6/2018 | Moschel |
| 10,004,934 B2 | 6/2018 | Pennington |
| 10,010,745 B1 | 7/2018 | Brumit |
| 10,010,755 B2 | 7/2018 | Watterson |
| 10,010,756 B2 | 7/2018 | Watterson |
| 10,016,646 B2 | 7/2018 | Butler |

(56) References Cited

U.S. PATENT DOCUMENTS

| | | |
|---|---|---|
| 10,022,583 B2 | 7/2018 | Wang |
| 10,029,145 B2 | 7/2018 | Douglass |
| 10,038,952 B2 | 7/2018 | Labrosse et al. |
| D826,350 S | 8/2018 | Hochstrasser |
| 10,046,196 B2 | 8/2018 | Ercanbrack |
| D827,733 S | 9/2018 | Hochstrasser |
| 10,065,064 B2 | 9/2018 | Smith et al. |
| 10,071,285 B2 | 9/2018 | Smith et al. |
| 10,076,437 B2 | 9/2018 | Plath |
| 10,085,586 B2 | 10/2018 | Smith |
| 10,086,254 B2 | 10/2018 | Watterson |
| 10,118,064 B1 | 11/2018 | Cox |
| 10,136,842 B2 | 11/2018 | Ashby |
| 10,186,161 B2 | 1/2019 | Watterson |
| 10,188,890 B2 | 1/2019 | Olson |
| 10,207,143 B2 | 2/2019 | Dalebout |
| 10,207,145 B2 | 2/2019 | Tyger |
| 10,207,147 B2 | 2/2019 | Ercanbrack |
| 10,207,148 B2 | 2/2019 | Powell |
| 10,212,994 B2 | 2/2019 | Watterson |
| 10,220,259 B2 | 3/2019 | Brammer |
| 10,226,396 B2 | 3/2019 | Ashby |
| 10,226,664 B2 | 3/2019 | Dalebout |
| 10,252,109 B2 | 4/2019 | Watterson |
| 10,258,828 B2 | 4/2019 | Dalebout |
| 10,272,317 B2 | 4/2019 | Watterson |
| 10,279,212 B2 | 5/2019 | Dalebout et al. |
| 10,293,211 B2 | 5/2019 | Watterson et al. |
| D852,292 S | 6/2019 | Cutler |
| 10,343,017 B2 | 7/2019 | Jackson |
| 10,376,736 B2 | 8/2019 | Powell |
| 10,388,183 B2 | 8/2019 | Watterson |
| 10,391,361 B2 | 8/2019 | Watterson |
| D864,320 S | 10/2019 | Weston |
| D864,321 S | 10/2019 | Weston |
| 10,426,989 B2 | 10/2019 | Dalebout |
| 10,433,612 B2 | 10/2019 | Ashby |
| 10,441,840 B2 | 10/2019 | Dalebout |
| 10,449,416 B2 | 10/2019 | Dalebout |
| D868,909 S | 12/2019 | Cutler |
| 10,492,519 B2 | 12/2019 | Capell |
| 10,493,349 B2 | 12/2019 | Watterson |
| 10,500,473 B2 | 12/2019 | Watterson |
| 10,543,395 B2 | 1/2020 | Powell et al. |
| 10,561,877 B2 | 2/2020 | Workman |
| 10,561,893 B2 | 2/2020 | Chatterton |
| 10,561,894 B2 | 2/2020 | Dalebout |
| 10,569,121 B2 | 2/2020 | Watterson |
| 10,569,123 B2 | 2/2020 | Hochstrasser |
| 2001/0041647 A1* | 11/2001 | Itoh .................. A63B 22/00 482/9 |
| 2002/0016235 A1 | 2/2002 | Ashby |
| 2002/0025888 A1 | 2/2002 | Germanton |
| 2002/0052268 A1 | 5/2002 | Morcillo-Quintero |
| 2002/0072436 A1 | 6/2002 | Liu |
| 2002/0077221 A1 | 6/2002 | Dalebout |
| 2002/0086779 A1 | 7/2002 | Wilkinson |
| 2002/0091043 A1 | 7/2002 | Rexach |
| 2002/0101880 A1 | 8/2002 | Kim |
| 2002/0128127 A1 | 9/2002 | Chen |
| 2002/0132703 A1* | 9/2002 | Martinez ............. A63B 24/00 482/8 |
| 2002/0159253 A1 | 10/2002 | Dalebout |
| 2002/0160891 A1 | 10/2002 | Gallagher |
| 2002/0193213 A1 | 12/2002 | Batca |
| 2003/0008731 A1 | 1/2003 | Anderson et al. |
| 2003/0017918 A1 | 1/2003 | Webb et al. |
| 2003/0022765 A1 | 1/2003 | Wu |
| 2003/0022770 A1 | 1/2003 | Lee |
| 2003/0045406 A1 | 3/2003 | Stone |
| 2003/0060344 A1 | 3/2003 | David |
| 2003/0060345 A1 | 3/2003 | Piane |
| 2003/0092532 A1 | 5/2003 | Giannelli et al. |
| 2003/0100413 A1 | 5/2003 | Huang |
| 2003/0100415 A1 | 5/2003 | Augustine et al. |
| 2003/0114276 A1 | 6/2003 | Schiff |
| 2003/0122384 A1 | 7/2003 | Swanson et al. |
| 2003/0148862 A1 | 8/2003 | Chen |
| 2003/0166434 A1 | 9/2003 | Lopez-Santillana et al. |
| 2003/0171189 A1 | 9/2003 | Kaufman |
| 2003/0186792 A1 | 10/2003 | Keeler |
| 2003/0211916 A1 | 11/2003 | Capuano |
| 2003/0216230 A1 | 11/2003 | Wang |
| 2004/0005961 A1 | 1/2004 | Iund |
| 2004/0005965 A1 | 1/2004 | Panatta |
| 2004/0009856 A1 | 1/2004 | Hammer |
| 2004/0014571 A1 | 1/2004 | Haynes |
| 2004/0021046 A1 | 2/2004 | Hutchison |
| 2004/0023761 A1 | 2/2004 | Emery |
| 2004/0023766 A1 | 2/2004 | Slone |
| 2004/0025993 A1 | 2/2004 | Russell |
| 2004/0033866 A1 | 2/2004 | Shapiro |
| 2004/0033868 A1 | 2/2004 | Van Straaten |
| 2004/0043873 A1 | 3/2004 | Wilkinson et al. |
| 2004/0053752 A1 | 3/2004 | Yang |
| 2004/0072662 A1 | 4/2004 | Landfair |
| 2004/0077468 A1 | 4/2004 | Myles |
| 2004/0087420 A1 | 5/2004 | Montesquieux |
| 2004/0091307 A1 | 5/2004 | James |
| 2004/0097353 A1 | 5/2004 | Mencis |
| 2004/0138032 A1 | 7/2004 | Van Straaten |
| 2004/0142799 A1 | 7/2004 | Yeo |
| 2004/0142801 A1 | 7/2004 | Lin |
| 2004/0162194 A1 | 8/2004 | Habing |
| 2004/0162196 A1 | 8/2004 | Degroot |
| 2004/0171464 A1 | 9/2004 | Ashby et al. |
| 2004/0171465 A1 | 9/2004 | Hald |
| 2004/0185988 A1 | 9/2004 | Hsiung |
| 2004/0198569 A1 | 10/2004 | Sanford-Schwentke |
| 2004/0204294 A2 | 10/2004 | Wilkinson |
| 2004/0208943 A1 | 10/2004 | Miketin |
| 2004/0242388 A1 | 12/2004 | Kusminsky |
| 2004/0266591 A1 | 12/2004 | Alessandri et al. |
| 2005/0003931 A1 | 1/2005 | Mills et al. |
| 2005/0037904 A1 | 2/2005 | Chang |
| 2005/0044984 A1 | 3/2005 | Jones |
| 2005/0049117 A1 | 3/2005 | Rodgers |
| 2005/0049123 A1 | 3/2005 | Dalebout et al. |
| 2005/0054492 A1 | 3/2005 | Neff |
| 2005/0061587 A1 | 3/2005 | Tsai |
| 2005/0065003 A1 | 3/2005 | Klotzki |
| 2005/0077805 A1 | 4/2005 | Dalebout |
| 2005/0085348 A1 | 4/2005 | Kiefer |
| 2005/0085352 A1 | 4/2005 | Baxter |
| 2005/0101463 A1 | 5/2005 | Chen |
| 2005/0107226 A1 | 5/2005 | Monda |
| 2005/0107229 A1 | 5/2005 | Wickens |
| 2005/0113223 A1 | 5/2005 | Dovner et al. |
| 2005/0130814 A1 | 6/2005 | Nitta et al. |
| 2005/0148440 A1 | 7/2005 | Denton |
| 2005/0148442 A1 | 7/2005 | Watterson |
| 2005/0159278 A1 | 7/2005 | Mcvay |
| 2005/0164839 A1 | 7/2005 | Watterson |
| 2005/0170937 A1 | 8/2005 | van Straaten |
| 2005/0181347 A1 | 8/2005 | Barnes et al. |
| 2005/0181916 A1 | 8/2005 | Frost et al. |
| 2005/0187075 A1 | 8/2005 | Bellamy |
| 2005/0233873 A1 | 10/2005 | Chen |
| 2005/0248713 A1 | 11/2005 | Hirosue et al. |
| 2005/0250619 A1 | 11/2005 | Daikeler et al. |
| 2005/0272564 A1 | 12/2005 | Pyles et al. |
| 2005/0272575 A1 | 12/2005 | Melegati |
| 2005/0272577 A1 | 12/2005 | Olson |
| 2005/0277520 A1* | 12/2005 | Van Waes ............. A63B 22/02 482/54 |
| 2005/0283051 A1 | 12/2005 | Chen |
| 2006/0003877 A1 | 1/2006 | Harmon |
| 2006/0019806 A1 | 1/2006 | Mikulski |
| 2006/0021155 A1 | 2/2006 | Lang et al. |
| 2006/0030465 A1 | 2/2006 | Johnson |
| 2006/0033392 A1 | 2/2006 | Ritchey |
| 2006/0035755 A1* | 2/2006 | Dalebout ......... A63B 21/00072 482/52 |
| 2006/0035768 A1 | 2/2006 | Kowalis et al. |

(56) References Cited

U.S. PATENT DOCUMENTS

| | | |
|---|---|---|
| 2006/0035772 A1 | 2/2006 | Golesh et al. |
| 2006/0040810 A1 | 2/2006 | Chu |
| 2006/0084422 A1 | 4/2006 | Huang et al. |
| 2006/0084556 A1 | 4/2006 | Payne |
| 2006/0116253 A1 | 6/2006 | Nizam |
| 2006/0128540 A1 | 6/2006 | Engle |
| 2006/0135322 A1* | 6/2006 | Rocker .............. A63B 23/1209 482/54 |
| 2006/0148622 A1 | 7/2006 | Chen |
| 2006/0160677 A1 | 7/2006 | Piane, Jr. |
| 2006/0189452 A1 | 8/2006 | Chou |
| 2006/0217237 A1 | 9/2006 | Rhodes |
| 2006/0217240 A1 | 9/2006 | White |
| 2006/0217242 A1 | 9/2006 | Karpachev |
| 2006/0240955 A1 | 10/2006 | Pu |
| 2006/0240959 A1 | 10/2006 | Huang |
| 2006/0247107 A1 | 11/2006 | Carter |
| 2006/0251638 A1 | 11/2006 | Guenzler-Pukall |
| 2006/0252612 A1 | 11/2006 | Melcer |
| 2006/0258519 A1 | 11/2006 | Ardito, III et al. |
| 2006/0281608 A1 | 12/2006 | Tumminello |
| 2007/0004569 A1 | 1/2007 | Cao |
| 2007/0013655 A1 | 1/2007 | Rosenberg et al. |
| 2007/0017025 A1 | 1/2007 | Myer |
| 2007/0018465 A1 | 1/2007 | Vassilakos |
| 2007/0021280 A1 | 1/2007 | Tyree |
| 2007/0042878 A1 | 2/2007 | Lundquist |
| 2007/0057001 A1 | 3/2007 | Wang |
| 2007/0066448 A1* | 3/2007 | Pan .................... A63B 22/0235 482/54 |
| 2007/0087920 A1 | 4/2007 | Dachraoui et al. |
| 2007/0093369 A1 | 4/2007 | Bocchicchio |
| 2007/0117683 A1 | 5/2007 | Ercanbrack |
| 2007/0123390 A1 | 5/2007 | Mathis |
| 2007/0123396 A1 | 5/2007 | Ellis |
| 2007/0135272 A1 | 6/2007 | Stuckey |
| 2007/0135279 A1 | 6/2007 | Purdy et al. |
| 2007/0141871 A1 | 6/2007 | Scherer et al. |
| 2007/0155600 A1 | 7/2007 | Cunningham et al. |
| 2007/0161468 A1 | 7/2007 | Yanagisawa et al. |
| 2007/0161470 A1 | 7/2007 | Berryman |
| 2007/0161472 A1 | 7/2007 | Drechsler |
| 2007/0176035 A1 | 8/2007 | Campbell |
| 2007/0179030 A1 | 8/2007 | Slawinski |
| 2007/0184944 A1 | 8/2007 | Huang |
| 2007/0190508 A1 | 8/2007 | Dalton |
| 2007/0197353 A1 | 8/2007 | Hundley |
| 2007/0202992 A1 | 8/2007 | Grasshoff |
| 2007/0232455 A1 | 10/2007 | Hanoun |
| 2007/0232461 A1 | 10/2007 | Jenkins et al. |
| 2007/0232463 A1 | 10/2007 | Wu |
| 2007/0243975 A1 | 10/2007 | Gearon |
| 2007/0254778 A1 | 11/2007 | Ashby |
| 2007/0259759 A1 | 11/2007 | Sumners et al. |
| 2007/0259763 A1 | 11/2007 | McKeown et al. |
| 2007/0270284 A1 | 11/2007 | Lin |
| 2007/0281836 A1 | 12/2007 | Gearon |
| 2007/0287606 A1 | 12/2007 | Mac Millan |
| 2007/0298941 A1 | 12/2007 | Egger |
| 2007/0298945 A1 | 12/2007 | Mehta |
| 2007/0298947 A1 | 12/2007 | Eksteen |
| 2008/0020898 A1 | 1/2008 | Pyles et al. |
| 2008/0020911 A1 | 1/2008 | Castello Neto |
| 2008/0070755 A1 | 3/2008 | McKee |
| 2008/0085819 A1 | 4/2008 | Yang et al. |
| 2008/0085820 A1 | 4/2008 | Majkrzak |
| 2008/0090703 A1 | 4/2008 | Rosenberg |
| 2008/0096735 A1 | 4/2008 | Grider |
| 2008/0103034 A1 | 5/2008 | Mihara et al. |
| 2008/0119337 A1 | 5/2008 | Wilkins |
| 2008/0139370 A1 | 6/2008 | Charnitski |
| 2008/0146418 A1 | 6/2008 | Summers |
| 2008/0153676 A1 | 6/2008 | Krietzman |
| 2008/0161168 A1 | 7/2008 | Hsiao |
| 2008/0161170 A1 | 7/2008 | Lumpee |
| 2008/0161653 A1 | 7/2008 | Lin et al. |
| 2008/0182731 A1 | 7/2008 | Vittone |
| 2008/0188362 A1 | 8/2008 | Chen |
| 2008/0200853 A1 | 8/2008 | Tielve |
| 2008/0204225 A1 | 8/2008 | Kitchen |
| 2008/0207407 A1 | 8/2008 | Yeh |
| 2008/0207415 A1 | 8/2008 | Tsai |
| 2008/0214971 A1 | 9/2008 | Talish |
| 2008/0228110 A1 | 9/2008 | Berme |
| 2008/0242520 A1 | 10/2008 | Hubbard |
| 2008/0261785 A1 | 10/2008 | Albanese |
| 2008/0279896 A1 | 11/2008 | Heinen et al. |
| 2008/0280734 A1 | 11/2008 | Dickie et al. |
| 2008/0300110 A1 | 12/2008 | Smith |
| 2008/0300118 A1 | 12/2008 | Wehrell |
| 2008/0318738 A1 | 12/2008 | Chen |
| 2008/0318744 A1 | 12/2008 | Barra |
| 2009/0042698 A1 | 2/2009 | Wang |
| 2009/0075784 A1 | 3/2009 | Hoggan |
| 2009/0075793 A1 | 3/2009 | Trainor |
| 2009/0105052 A1 | 4/2009 | Dalebout et al. |
| 2009/0111658 A1 | 4/2009 | Juan |
| 2009/0118098 A1 | 5/2009 | Yeh |
| 2009/0131230 A1 | 5/2009 | Cole |
| 2009/0149302 A1 | 6/2009 | Thuma |
| 2009/0181830 A1 | 7/2009 | Wu |
| 2009/0186748 A1 | 7/2009 | Golesh et al. |
| 2009/0196417 A1 | 8/2009 | Beaver et al. |
| 2009/0305852 A1 | 12/2009 | Hoglund |
| 2010/0004104 A1 | 1/2010 | Gustafson |
| 2010/0005624 A1 | 1/2010 | Swearingen |
| 2010/0031803 A1 | 2/2010 | Lozada et al. |
| 2010/0048368 A1 | 2/2010 | Donofrio |
| 2010/0056345 A1 | 3/2010 | Liu |
| 2010/0063426 A1 | 3/2010 | Planke |
| 2010/0093493 A1 | 4/2010 | Eldridge |
| 2010/0105530 A1 | 4/2010 | Inaizumi |
| 2010/0130337 A1 | 5/2010 | Stewart |
| 2010/0156760 A1 | 6/2010 | Cheswick |
| 2010/0178981 A1 | 7/2010 | Holcomb |
| 2010/0179035 A1 | 7/2010 | Carnahan |
| 2010/0184570 A1 | 7/2010 | Cheng |
| 2010/0197462 A1 | 8/2010 | Piane, Jr. |
| 2010/0197465 A1 | 8/2010 | Stevenson |
| 2010/0210418 A1 | 8/2010 | Park |
| 2010/0216610 A1 | 8/2010 | Gedeon-Janvier |
| 2010/0233664 A1 | 9/2010 | Wroclawsky |
| 2010/0234184 A1 | 9/2010 | Le Page |
| 2010/0234193 A1 | 9/2010 | Friedman |
| 2010/0240493 A1 | 9/2010 | Wang |
| 2010/0242246 A1 | 9/2010 | Dalebout |
| 2010/0285933 A1 | 11/2010 | Nalley |
| 2010/0304938 A1 | 12/2010 | Olson |
| 2010/0304940 A1 | 12/2010 | Svenberg |
| 2010/0311552 A1 | 12/2010 | Sumners |
| 2010/0317488 A1* | 12/2010 | Cartaya .............. A63B 21/4013 482/5 |
| 2010/0323852 A1 | 12/2010 | Locsin |
| 2010/0327603 A1 | 12/2010 | Suaan |
| 2011/0028282 A1 | 2/2011 | Sbragia |
| 2011/0082013 A1 | 4/2011 | Bastian |
| 2011/0082015 A1 | 4/2011 | Dreissigacker et al. |
| 2011/0131005 A1 | 6/2011 | Ueshima et al. |
| 2011/0165995 A1 | 7/2011 | Paulus |
| 2011/0165996 A1 | 7/2011 | Paulus |
| 2011/0165997 A1 | 7/2011 | Reich |
| 2011/0172058 A1 | 7/2011 | Deaconu |
| 2011/0172068 A1 | 7/2011 | Tyson, III |
| 2011/0185309 A1 | 7/2011 | Challinor et al. |
| 2011/0188980 A1 | 8/2011 | Pumroy |
| 2011/0190096 A1 | 8/2011 | Clarke |
| 2011/0195819 A1 | 8/2011 | Shaw |
| 2011/0195825 A1 | 8/2011 | Liester |
| 2011/0237407 A1 | 9/2011 | Kaleal |
| 2011/0240403 A1 | 10/2011 | Meillet |
| 2011/0281249 A1 | 11/2011 | Gammell et al. |
| 2011/0281691 A1 | 11/2011 | Ellis |
| 2011/0287905 A1 | 11/2011 | Reyes |
| 2012/0004074 A1 | 1/2012 | Schelzig |

(56) References Cited

U.S. PATENT DOCUMENTS

| | | |
|---|---|---|
| 2012/0015787 A2 | 1/2012 | Strong Crawley |
| 2012/0021876 A1 | 1/2012 | Hsiung |
| 2012/0021877 A1 | 1/2012 | Lundquist et al. |
| 2012/0035024 A1 | 2/2012 | Price |
| 2012/0083396 A1 | 4/2012 | Aquino |
| 2012/0115691 A1 | 5/2012 | Munroe |
| 2012/0142503 A1 | 6/2012 | Sevadjian |
| 2012/0158238 A1 | 6/2012 | Daley |
| 2012/0225758 A1 | 9/2012 | Shaw |
| 2012/0237911 A1 | 9/2012 | Watterson |
| 2012/0238411 A1 | 9/2012 | McBride et al. |
| 2012/0277070 A1 | 11/2012 | Sienna |
| 2012/0283074 A1 | 11/2012 | Hutchins |
| 2012/0295774 A1 | 11/2012 | Dalebout et al. |
| 2012/0322625 A1 | 12/2012 | Park |
| 2012/0322629 A1 | 12/2012 | Webb |
| 2012/0329615 A1 | 12/2012 | Jeong |
| 2013/0014321 A1 | 1/2013 | Sullivan |
| 2013/0018494 A1 | 1/2013 | Amini |
| 2013/0035219 A1 | 2/2013 | Williams |
| 2013/0053220 A1 | 2/2013 | Monaco |
| 2013/0065732 A1 | 3/2013 | Hopp |
| 2013/0090212 A1 | 4/2013 | Wang |
| 2013/0090216 A1 | 4/2013 | Jackson |
| 2013/0102443 A1 | 4/2013 | Lundquist et al. |
| 2013/0123083 A1 | 5/2013 | Sip |
| 2013/0150214 A1* | 6/2013 | Wu ............... A63B 22/00 482/4 |
| 2013/0165195 A1 | 6/2013 | Watterson |
| 2013/0172152 A1 | 7/2013 | Watterson |
| 2013/0172153 A1 | 7/2013 | Watterson |
| 2013/0178334 A1 | 7/2013 | Brammer |
| 2013/0178338 A1 | 7/2013 | Ross |
| 2013/0178346 A1 | 7/2013 | Lin |
| 2013/0178768 A1 | 7/2013 | Dalebout |
| 2013/0190136 A1 | 7/2013 | Watterson |
| 2013/0193655 A1 | 8/2013 | Kaye et al. |
| 2013/0196298 A1 | 8/2013 | Watterson |
| 2013/0196821 A1 | 8/2013 | Watterson et al. |
| 2013/0196822 A1 | 8/2013 | Watterson |
| 2013/0218585 A1 | 8/2013 | Watterson |
| 2013/0225373 A1 | 8/2013 | Poat |
| 2013/0225377 A1 | 8/2013 | Lee et al. |
| 2013/0231226 A1 | 9/2013 | Bonutti |
| 2013/0237383 A1 | 9/2013 | Chen |
| 2013/0244836 A1 | 9/2013 | Maughan |
| 2013/0267383 A1 | 10/2013 | Watterson |
| 2013/0268101 A1 | 10/2013 | Brammer |
| 2013/0274067 A1 | 10/2013 | Watterson et al. |
| 2013/0274074 A1 | 10/2013 | Ghandour |
| 2013/0281241 A1 | 10/2013 | Watterson |
| 2013/0303334 A1 | 11/2013 | Adhami |
| 2013/0310230 A1 | 11/2013 | Norris |
| 2013/0337974 A1 | 12/2013 | Yanev et al. |
| 2013/0337980 A1 | 12/2013 | Himmelrick et al. |
| 2014/0024499 A1 | 1/2014 | Watterson |
| 2014/0073488 A1 | 3/2014 | Wu |
| 2014/0073970 A1 | 3/2014 | Ashby |
| 2014/0080678 A1 | 3/2014 | Wu |
| 2014/0100085 A1* | 4/2014 | Hao ............... A63B 22/02 482/54 |
| 2014/0106943 A1 | 4/2014 | Simonetti |
| 2014/0106948 A1 | 4/2014 | Agostini |
| 2014/0121071 A1 | 5/2014 | Strom et al. |
| 2014/0135173 A1 | 5/2014 | Watterson |
| 2014/0162856 A1 | 6/2014 | Kramer |
| 2014/0187389 A1 | 7/2014 | Berg |
| 2014/0221175 A1 | 8/2014 | Liu |
| 2014/0221881 A1 | 8/2014 | Schlauder et al. |
| 2014/0228175 A1 | 8/2014 | Lemos et al. |
| 2014/0274574 A1 | 9/2014 | Shorten et al. |
| 2014/0274579 A1 | 9/2014 | Olson |
| 2014/0287884 A1 | 9/2014 | Buchanan |
| 2014/0287886 A1 | 9/2014 | Patti |
| 2014/0309085 A1 | 10/2014 | Watterson |
| 2014/0309092 A1 | 10/2014 | De Michele |
| 2014/0357457 A1 | 12/2014 | Boekema |
| 2015/0038300 A1 | 2/2015 | Forhan et al. |
| 2015/0069738 A1 | 3/2015 | Knight |
| 2015/0072842 A1 | 3/2015 | Segal |
| 2015/0126348 A1 | 5/2015 | Kaye et al. |
| 2015/0148204 A1 | 5/2015 | Sleppy |
| 2015/0165270 A1 | 6/2015 | Allos |
| 2015/0182779 A1 | 7/2015 | Dalebout |
| 2015/0182781 A1 | 7/2015 | Watterson |
| 2015/0202487 A1 | 7/2015 | Wu |
| 2015/0209610 A1 | 7/2015 | Dalebout et al. |
| 2015/0238801 A1 | 8/2015 | Meredith |
| 2015/0238817 A1 | 8/2015 | Watterson |
| 2015/0250418 A1 | 9/2015 | Ashby |
| 2015/0251055 A1 | 9/2015 | Ashby |
| 2015/0253210 A1 | 9/2015 | Ashby et al. |
| 2015/0253735 A1 | 9/2015 | Watterson |
| 2015/0253736 A1 | 9/2015 | Watterson |
| 2015/0258560 A1 | 9/2015 | Ashby |
| 2015/0273267 A1 | 10/2015 | Manzke |
| 2015/0283420 A1 | 10/2015 | Chang |
| 2015/0283421 A1 | 10/2015 | Gaylord |
| 2015/0352396 A1* | 12/2015 | Dalebout ............... A63B 21/0051 482/54 |
| 2015/0360073 A1 | 12/2015 | Moran et al. |
| 2015/0367161 A1 | 12/2015 | Wiegardt |
| 2016/0001123 A1 | 1/2016 | Parrish, Jr. |
| 2016/0008650 A1 | 1/2016 | Jue et al. |
| 2016/0023043 A1* | 1/2016 | Grundy ............... A63B 24/0062 482/8 |
| 2016/0051857 A1 | 2/2016 | Rasner |
| 2016/0058335 A1 | 3/2016 | Ashby |
| 2016/0063615 A1 | 3/2016 | Watterson |
| 2016/0074691 A1 | 3/2016 | Pearce et al. |
| 2016/0092909 A1 | 3/2016 | Watterson |
| 2016/0096064 A1 | 4/2016 | Gatti |
| 2016/0101311 A1 | 4/2016 | Workman |
| 2016/0107065 A1 | 4/2016 | Brammer |
| 2016/0121074 A1 | 5/2016 | Ashby |
| 2016/0121156 A1 | 5/2016 | Bach |
| 2016/0148535 A1 | 5/2016 | Ashby |
| 2016/0148536 A1 | 5/2016 | Ashby |
| 2016/0158595 A1 | 6/2016 | Dalebout |
| 2016/0199683 A1 | 7/2016 | Shamlin |
| 2016/0206248 A1 | 7/2016 | Sartor et al. |
| 2016/0206922 A1 | 7/2016 | Dalebout et al. |
| 2016/0256728 A1 | 9/2016 | Tang |
| 2016/0278487 A1 | 9/2016 | Postolek |
| 2016/0310789 A1* | 10/2016 | Emerson ............... A63B 24/0062 |
| 2016/0319850 A1 | 11/2016 | Kamen et al. |
| 2016/0321075 A1 | 11/2016 | Catherwood et al. |
| 2016/0339298 A1 | 11/2016 | Kats |
| 2016/0346586 A1 | 12/2016 | Pullins et al. |
| 2016/0346595 A1 | 12/2016 | Dalebout |
| 2016/0346617 A1* | 12/2016 | Srugo ............... G09B 19/0038 |
| 2017/0021218 A1 | 1/2017 | Peritz |
| 2017/0036053 A1 | 2/2017 | Smith |
| 2017/0050069 A1 | 2/2017 | Ky |
| 2017/0050074 A1 | 2/2017 | Olson |
| 2017/0056711 A1 | 3/2017 | Dalebout et al. |
| 2017/0056715 A1 | 3/2017 | Dalebout et al. |
| 2017/0056726 A1 | 3/2017 | Dalebout et al. |
| 2017/0065852 A1 | 3/2017 | Cygan et al. |
| 2017/0106227 A1 | 4/2017 | Lalaoua |
| 2017/0106240 A1 | 4/2017 | Chuang |
| 2017/0124912 A1 | 5/2017 | Ashby |
| 2017/0165552 A1 | 6/2017 | Martin |
| 2017/0173394 A1 | 6/2017 | Rider |
| 2017/0193578 A1 | 7/2017 | Watterson |
| 2017/0197103 A1 | 7/2017 | Rau et al. |
| 2017/0197106 A1 | 7/2017 | Dalebout et al. |
| 2017/0239509 A1 | 8/2017 | Wang |
| 2017/0266481 A1 | 9/2017 | Dalebout |
| 2017/0266483 A1 | 9/2017 | Dalebout et al. |
| 2017/0266489 A1 | 9/2017 | Douglass |
| 2017/0266503 A1 | 9/2017 | Watterson et al. |
| 2017/0266532 A1 | 9/2017 | Watterson |
| 2017/0266533 A1 | 9/2017 | Dalebout |

(56) References Cited

U.S. PATENT DOCUMENTS

| | | |
|---|---|---|
| 2017/0270820 A1 | 9/2017 | Ashby |
| 2017/0274237 A1 | 9/2017 | Chang |
| 2017/0312580 A1 | 11/2017 | Chang |
| 2017/0319906 A1 | 11/2017 | Chang et al. |
| 2017/0326411 A1 | 11/2017 | Watterson |
| 2017/0367480 A1 | 12/2017 | Dickerson et al. |
| 2018/0001135 A1 | 1/2018 | Powell |
| 2018/0036572 A1 | 2/2018 | Hsu |
| 2018/0036585 A1 | 2/2018 | Powell |
| 2018/0085622 A1 | 3/2018 | Ivan |
| 2018/0085630 A1 | 3/2018 | Capell |
| 2018/0089396 A1 | 3/2018 | Capell |
| 2018/0099116 A1 | 4/2018 | Ashby |
| 2018/0099179 A1 | 4/2018 | Chatterton et al. |
| 2018/0099180 A1 | 4/2018 | Wilkinson |
| 2018/0099205 A1 | 4/2018 | Watterson |
| 2018/0104533 A1 | 4/2018 | Powell et al. |
| 2018/0111034 A1 | 4/2018 | Watterson |
| 2018/0117385 A1 | 5/2018 | Watterson et al. |
| 2018/0117393 A1 | 5/2018 | Ercanbrack |
| 2018/0140886 A1 | 5/2018 | Hetrick et al. |
| 2018/0154205 A1 | 6/2018 | Watterson |
| 2018/0154207 A1 | 6/2018 | Hochstrasser |
| 2018/0154208 A1 | 6/2018 | Powell et al. |
| 2018/0154209 A1 | 6/2018 | Watterson |
| 2018/0200566 A1 | 7/2018 | Weston |
| 2018/0256933 A1 | 9/2018 | Olson |
| 2019/0058370 A1 | 2/2019 | Tinney |
| 2019/0080624 A1 | 3/2019 | Watterson |
| 2019/0151698 A1 | 5/2019 | Olson |
| 2019/0168072 A1 | 6/2019 | Brammer |
| 2019/0178313 A1 | 6/2019 | Wrobel |
| 2019/0192898 A1 | 6/2019 | Dalebout |
| 2019/0192952 A1 | 6/2019 | Powell |
| 2019/0209893 A1 | 7/2019 | Watterson |
| 2019/0223612 A1 | 7/2019 | Watterson |
| 2019/0232112 A1 | 8/2019 | Dalebout |
| 2019/0269958 A1 | 9/2019 | Dalebout |
| 2019/0269971 A1 | 9/2019 | Capell |
| 2019/0275366 A1 | 9/2019 | Powell |
| 2019/0282852 A1 | 9/2019 | Dalebout |
| 2019/0328079 A1 | 10/2019 | Ashby |
| 2019/0329091 A1 | 10/2019 | Powell |
| 2019/0376585 A1 | 12/2019 | Buchanan |
| 2020/0009417 A1 | 1/2020 | Dalebout |
| 2020/0016459 A1 | 1/2020 | Smith |
| 2020/0238130 A1 | 7/2020 | Silcock |
| 2020/0254295 A1 | 8/2020 | Watterson |
| 2020/0254309 A1 | 8/2020 | Watterson |
| 2020/0254311 A1 | 8/2020 | Watterson |

FOREIGN PATENT DOCUMENTS

| | | | |
|---|---|---|---|
| TW | I339127 | | 8/2008 |
| TW | M422981 | | 2/2012 |
| TW | M504568 | * | 3/2015 |
| WO | 2009014330 | | 1/2009 |
| WO | 2011094649 | | 8/2011 |

OTHER PUBLICATIONS

U.S. Appl. No. 15/245,953, Jan. 3, 2018, Non-final Rejection.
U.S. Appl. No. 15/245,953, Jul. 26, 2018, Non-final Rejection.
U.S. Appl. No. 15/245,953, Aug. 31, 2018, Non-final Rejection.
English Translation of Search Report for Taiwan Patent Application No. 104131458 dated Jun. 3, 2016.
English Translation of Search Report for Taiwan Patent Application No. 105126694 dated Oct. 3, 2017.
International Search Report and Written Opinion issued in PCT/US2016/048692 dated Dec. 1, 2016.
International Search Report and Written Opinion issued in PCT/US2017/023002 dated Jun. 28, 2017.
International Search Report and Written Opinion issued in PCT/US2017/022989 dated May 23, 2017.
English Abstract of Taiwan Patent No. TWM504568 dated Mar. 1, 2015.
U.S. Appl. No. 29/702,127, filed Sep. 16, 2019, Gordon Cutler.
U.S. Appl. No. 13/088,007, filed Apr. 15, 2011, Scott R. Watterson.
U.S. Appl. No. 15/973,176, filed May 7, 2018, Melanie Douglass.
U.S. Appl. No. 16/879,376, filed May 20, 2020, David Hays.
U.S. Appl. No. 16/992,870, filed Aug. 13, 2020, Gaylen Ercanbrack.
U.S. Appl. No. 16/992,886, filed Aug. 13, 2020, Willial T. Dalebout.
U.S. Appl. No. 17/067,310, filed Oct. 9, 2020, Jared Willardson.
U.S. Appl. No. 62/897,113, fld Sep. 9, 2019, Megan Jane Ostler.
U.S. Appl. No. 62/934,291, filed Nov. 12, 2019, William T. Dalebout.
U.S. Appl. No. 62/934,297, filed Nov. 12, 2019, William T. Dalebout.
U.S. Appl. No. 62/991,378, filed Mar. 18, 2020, Chris Nascimento.
U.S. Appl. No. 62/994,204, filed Mar. 24, 2020, Chase Brammer.
U.S. Appl. No. 63/073,081, filed Sep. 1, 2020, Darren C. Ashby.
U.S. Appl. No. 63/079,697, filed Sep. 17, 2020, Jared Willardson.
U.S. Appl. No. 63/086,793, filed Oct. 2, 2020, Darren C. Ashby.

* cited by examiner

STRENGTH EXERCISE MECHANISMS

CROSS-REFERENCE TO RELATED APPLICATIONS

This application claims priority to U.S. Provisional Patent Application No. 62/210,318 filed on Aug. 26, 2015, which application is herein incorporated by reference for all that it discloses.

BACKGROUND

Aerobic exercise is a popular form of exercise that improves one's cardiovascular health by reducing blood pressure and providing other benefits to the human body. Aerobic exercise generally involves low intensity physical exertion over a long duration of time. Typically, the human body can adequately supply enough oxygen to meet the body's demands at the intensity levels involved with aerobic exercise. Popular forms of aerobic exercise include running, jogging, swimming, and cycling among others activities. In contrast, anaerobic exercise typically involves high intensity exercises over a short duration of time. Popular forms of anaerobic exercise include strength training and short distance running.

Many choose to perform aerobic exercises indoors, such as in a gym or their home. Often, a user uses an aerobic exercise machine to have an aerobic workout indoors. One such type of aerobic exercise machine is a treadmill, which is a machine that has a running deck attached to a support frame. The running deck can support the weight of a person using the machine. The running deck incorporates a tread belt that is driven by a motor. A user can run or walk in place on the tread belt by running or walking at the tread belt's speed. The speed and other operations of the treadmill are generally controlled through a control module that is also attached to the support frame and within a convenient reach of the user. The control module can include a display, buttons for increasing or decreasing a speed of the conveyor belt, controls for adjusting a tilt angle of the running deck, or other controls. Other popular exercise machines that allow a user to perform aerobic exercises indoors include elliptical machines, rowing machines, stepper machines, and stationary bikes to name a few.

One type of dual use exercise machine is disclosed in U.S. Pat. No. 5,000,440 issued to Robert P. Lynch. In this reference, an exercise apparatus combines a treadmill with an upper body muscle stressing device that allows for simultaneous upper body exercise with aerobic exercise. This reference is incorporated by reference for all that it discloses.

SUMMARY

In one embodiment of the present invention, a treadmill includes a frame, an exercise deck attached to the frame, and a first handle movably attached to the frame. The first handle has a first orientation where the first handle is positioned within a region above the exercise deck and stabilized to support a user's weight during a body weight exercise, and a second orientation where the first handle is positioned away from the region above the exercise deck.

The first handle may be aligned with a length of the exercise deck in the first orientation and the first handle is transverse to the length of the exercise deck when in the second orientation.

The first handle may be pivotally attached to the frame.

A second handle may be movably attached to the frame is spaced an adjustable distance away from the first handle.

At least one of the first handle or the second handle may move laterally with respect to the frame.

The first handle and the second handle may be spaced approximately a human body width apart in the first orientation.

The treadmill further may include a repetition sensor to count the number of times that a user performs the body weight exercise.

The treadmill further may include a weight sensor to generate a weight value of a user applying their body weight to the first handle and the second handle.

The treadmill may include a display to present a repetition count of the body weight exercise.

The treadmill may include a display to present a body weight exercise calorie burn value based on a performance of the body weight exercise.

The treadmill may include a processor and memory.

The memory may include programmed instructions to cause the processor to calculate an exercise deck calorie burn value based on a performance of an exercise with the exercise deck.

The memory may include programmed instructions to cause the processor to calculate an body weight calorie burn value based on a performance of the body weight exercise.

The memory may include programmed instructions to cause the processor to add the exercise deck calorie burn value to the body weight exercise calorie burn value to generate a workout calorie burn value.

The memory may include programmed instructions to cause the processor to present the workout calorie burn value in a display.

The body weight exercise may be a dipping exercise.

The treadmill may include a tread belt incorporated into the exercise deck wherein the first handle is moved into the second orientation during a performance of an exercise on the tread belt.

The treadmill may include a push-up bar attached to the frame.

The treadmill may include a push-up bar attached to the exercise deck.

In one embodiment, a treadmill includes a frame, an exercise deck attached to the frame, a first handle movably attached to the frame, and a second handle movably attached to the frame and spaced a first distance from the first handle. The first handle and the second handle each comprise a first orientation where the first handle and the second handle are positioned within a region above the exercise deck and stabilized to support a user's weight during a body weight exercise and a second orientation where the first handle and the second handle are positioned away from the region above the exercise deck. The first handle and the second handle are spaced a human body width apart in the first orientation and capable of supporting a user's weight during a body weight exercise. The treadmill further includes a repetition sensor to count the number of times that a user performs the body weight exercise.

The first handle and the second handle may be spaced a human body width apart in the first orientation and capable of supporting a user's weight during a body weight exercise.

The treadmill may include a repetition sensor to count the number of times that a user performs the body weight exercise.

The first handle and the second handle may be aligned with a length of the exercise deck in the first orientation, and the first handle and the second handle are transverse to the length of the exercise deck in the second orientation.

At least one of the first handle and the second handle may be slidably attached to the frame.

The treadmill may further include a display to present a repetition count of the body weight exercise based on information gathered from the repetition sensor.

In one embodiment of the invention, a treadmill includes a frame, an exercise deck attached to the frame, a first handle movably attached to the frame, a second handle movably attached to the frame and spaced a first distance from the first handle. The first handle and the second handle each comprise a first orientation where the first handle and the second handle are positioned within a region above the exercise deck and stabilized to support a user's weight during a body weight exercise and a second orientation where the first handle and the second handle are positioned away from the region above the exercise deck. The first handle and the second handle are aligned with a length of the exercise deck in the first orientation, and the first handle and the second handle are transverse to the length of the exercise deck in the second orientation. The first handle and the second handle are spaced a human body width apart in the first orientation and capable of supporting a user's weight during a body weight exercise. The treadmill also includes a repetition sensor to count the number of times that a user performs the body weight exercise, and a display to present a repetition count of the body weight exercise based on information gathered from the repetition sensor. The treadmill also includes a processor and memory, the memory comprising programmed instructions to cause the processor to calculate an exercise deck calorie burn value based on an exercise deck exercise, calculate an body weight calorie burn value based on the body weight exercise, add the exercise deck calorie burn value to the body weight exercise calorie burn value to generate a workout calorie burn value, and present the workout calorie burn value in the display.

BRIEF DESCRIPTION OF THE DRAWINGS

The accompanying drawings illustrate various embodiments of the present apparatus and are a part of the specification. The illustrated embodiments are merely examples of the present apparatus and do not limit the scope thereof.

Throughout the drawings, identical reference numbers designate similar, but not necessarily identical, elements.

DETAILED DESCRIPTION

For purposes of this disclosure, the term "aligned" means parallel, substantially parallel, or forming an angle of less than 35.0 degrees. For purposes of this disclosure, the term "transverse" means perpendicular, substantially perpendicular, or forming an angle between 55.0 and 125.0 degrees. Also, for purposes of this disclosure, the term "length" means the longest dimension of an object. Also, for purposes of this disclosure, the term "width" means the dimension of an object from side to side. For the purposes of this disclosure, the term "above" generally means superjacent, substantially superjacent, or higher than another object although not directly overlying the object.

Figure 1A:
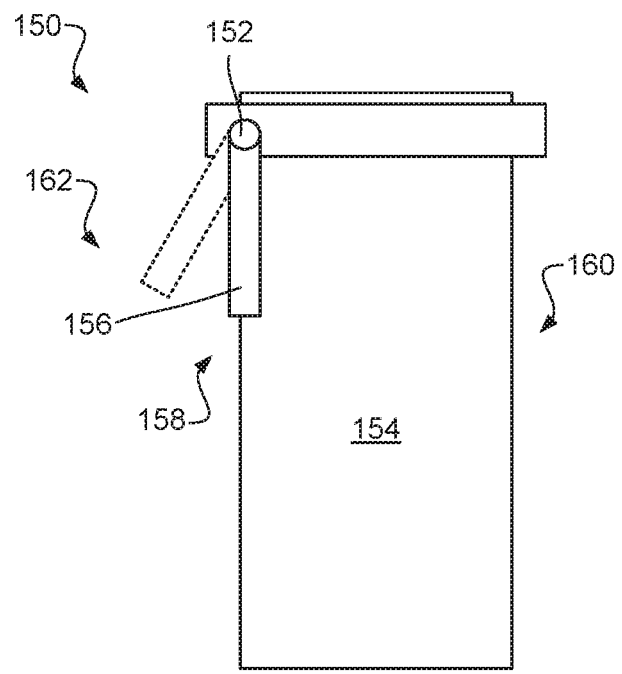
FIG. 1a illustrates a top view of an example of treadmill in accordance with the present disclosure.

Particularly, with reference to the figures, FIG. 1a illustrates an example of a treadmill 150 in accordance with the present disclosure. The treadmill 150 includes a frame 152, an exercise deck 154 attached to the frame 152, and a first handle 156 movably attached to the frame 152. The first handle 156 has a first orientation 158 where the first handle 156 is positioned within a region 160 above the exercise deck 154 and stabilized to support a user's weight during a body weight exercise, and a second orientation 162 where the first handle 156 is positioned away from the region 160 above the exercise deck 154.

Figure 1B:
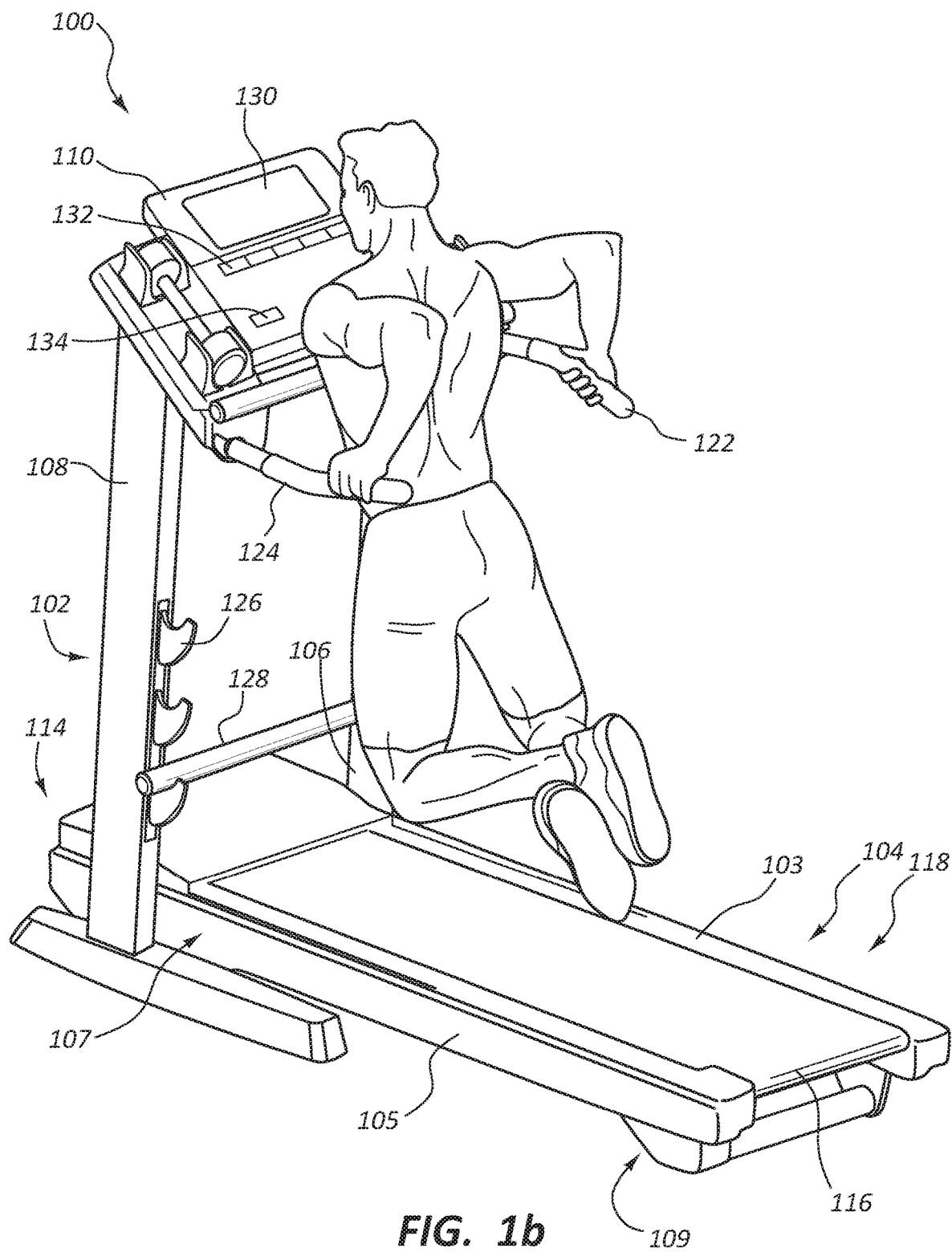
FIG. 1b illustrates a perspective view of an example of treadmill in accordance with the present disclosure.

FIG. 1b depicts a treadmill 100 with a frame 102, and an exercise deck 104 connected to the frame. The frame 102 includes a first post 106 and a second post 108. A console 110 is supported by the first post 106 and the second post 108.

The exercise deck 104 comprises a first rail 103 and a second rail 105. A first pulley is located in a front section 114 of the treadmill 100 and proximate a first end 107 of both the first and second rails, 103, 105. Also, a second pulley 116 is located in a rear section 118 of the treadmill 100 and proximate a rear end 109 of both the first and second rails, 103, 105. A tread belt 120 is disposed between the first pulley and the second pulley 116.

A first handle 122 is movably attached to the frame 102 on a first side of the treadmill 100, and a second handle 124 is movably attached to the frame 102 on a second side of the treadmill 100. In this example, the first and second handles 122, 124 are in a first orientation that is aligned with a length of the exercise deck 104. In such a first orientation, the first and second handles 122, 124 are positioned within a region that is above the exercise deck 104. In this example, the first and second handles 122, 124 are spaced approximately a human body width apart. Also, multiple bar catches 126 are incorporated into each of the first post 106 and the second post 108. Such bar catches 126 may be used to support a push-up bar 128.

The console 110 includes a display 130 and at least one input mechanism 132. Such an input mechanism 132 may be used to control a parameter of the treadmill 100 or record a condition during the performance of an exercise on the treadmill 100.

Further, the treadmill 100 includes at least one repetition sensor 134 that can count the number of repetitions of an exercise performed by the user. For example, the repetition sensor may be able to count the number of push-ups performed by the user with the push-up bar 128 or the number of body weight exercises performed by the user with the first and second handles 122, 124.

Figure 2:
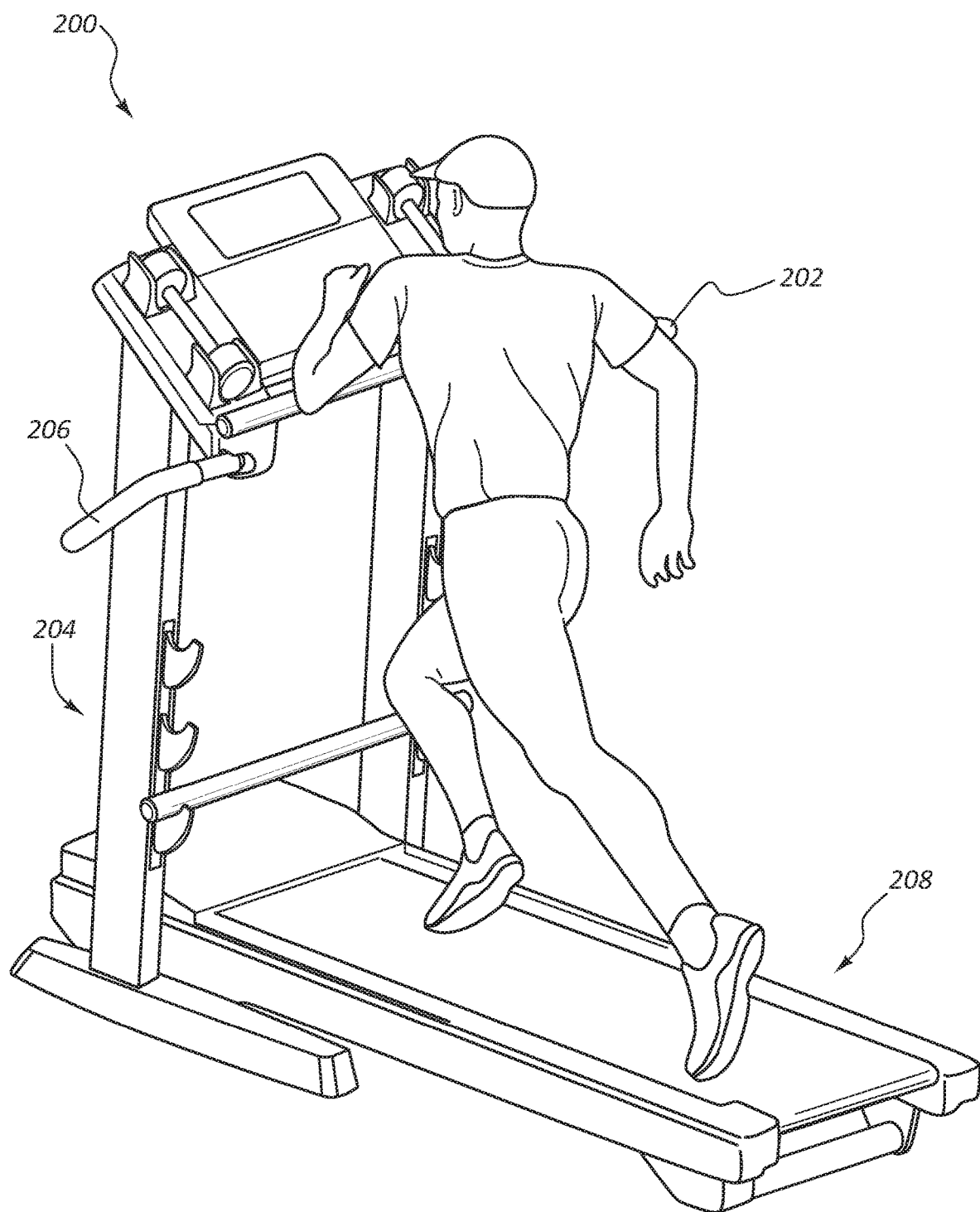
FIG. 2 illustrates a perspective view of an example of a treadmill in accordance with the present disclosure.

FIG. 2 depicts an example of a treadmill 200 with a first handle 202 movably attached to the treadmill's frame 204 and a second handle 206 movably attached to the treadmill's frame 204. The first and second handles 202, 206 are attached to the frame at a human body width apart from one another. In this example, the first and second handles 202, 206 are rotated outwardly from a center of the treadmill 200. In such an orientation, the first and second handles 202, 206 are transverse to the length of the exercise deck 208.

Figure 3:
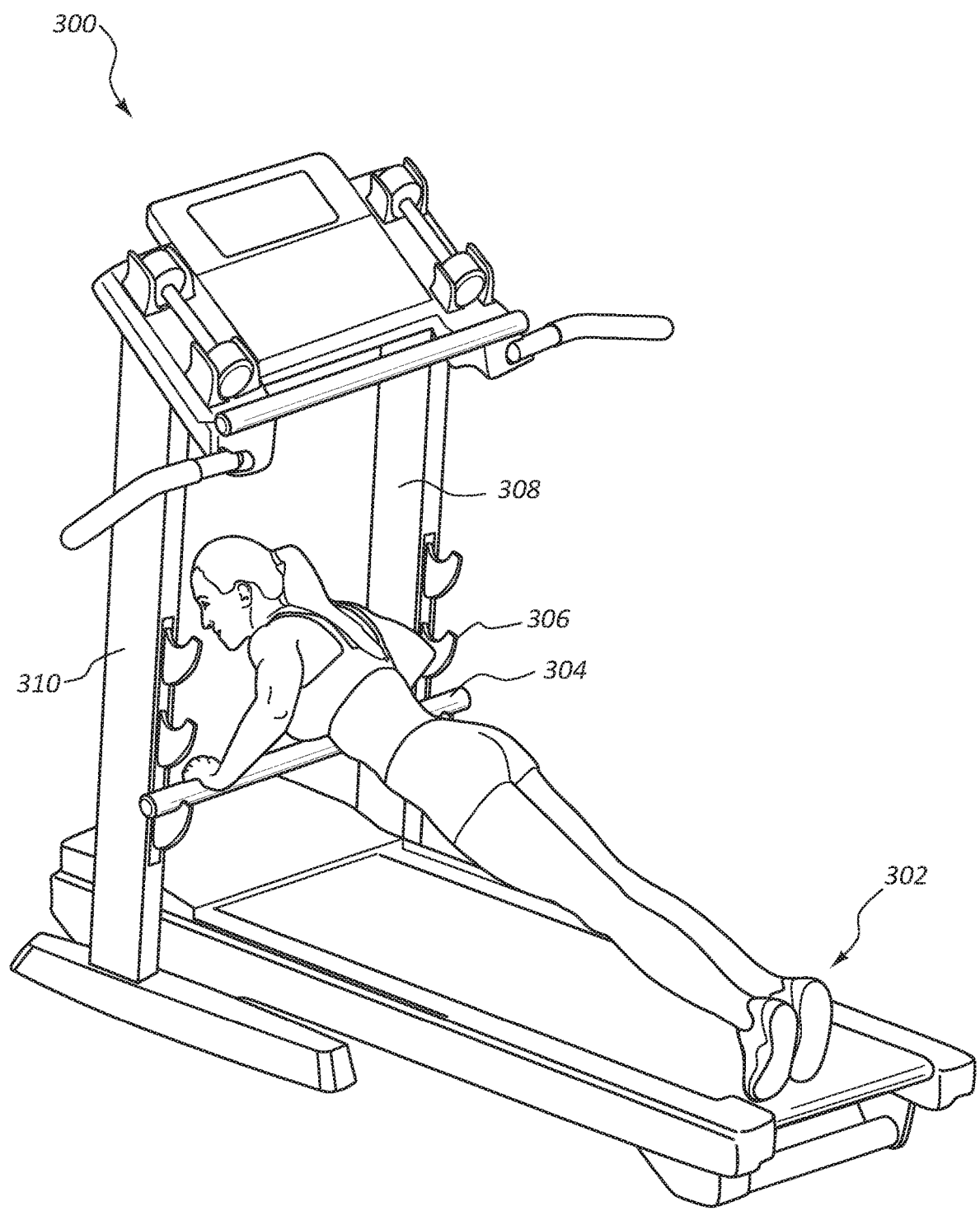
FIG. 3 illustrates a perspective view of an example of a treadmill in accordance with the present disclosure.

FIG. 3 depicts an example of a treadmill 300 of a user performing an anaerobic exercise on the exercise deck 302 with the push-up bar 304. The push-up bar 304 is secured to the catches 306 incorporated into the first post 308 and the second post 310 of the treadmill's frame 312.

Figure 4:
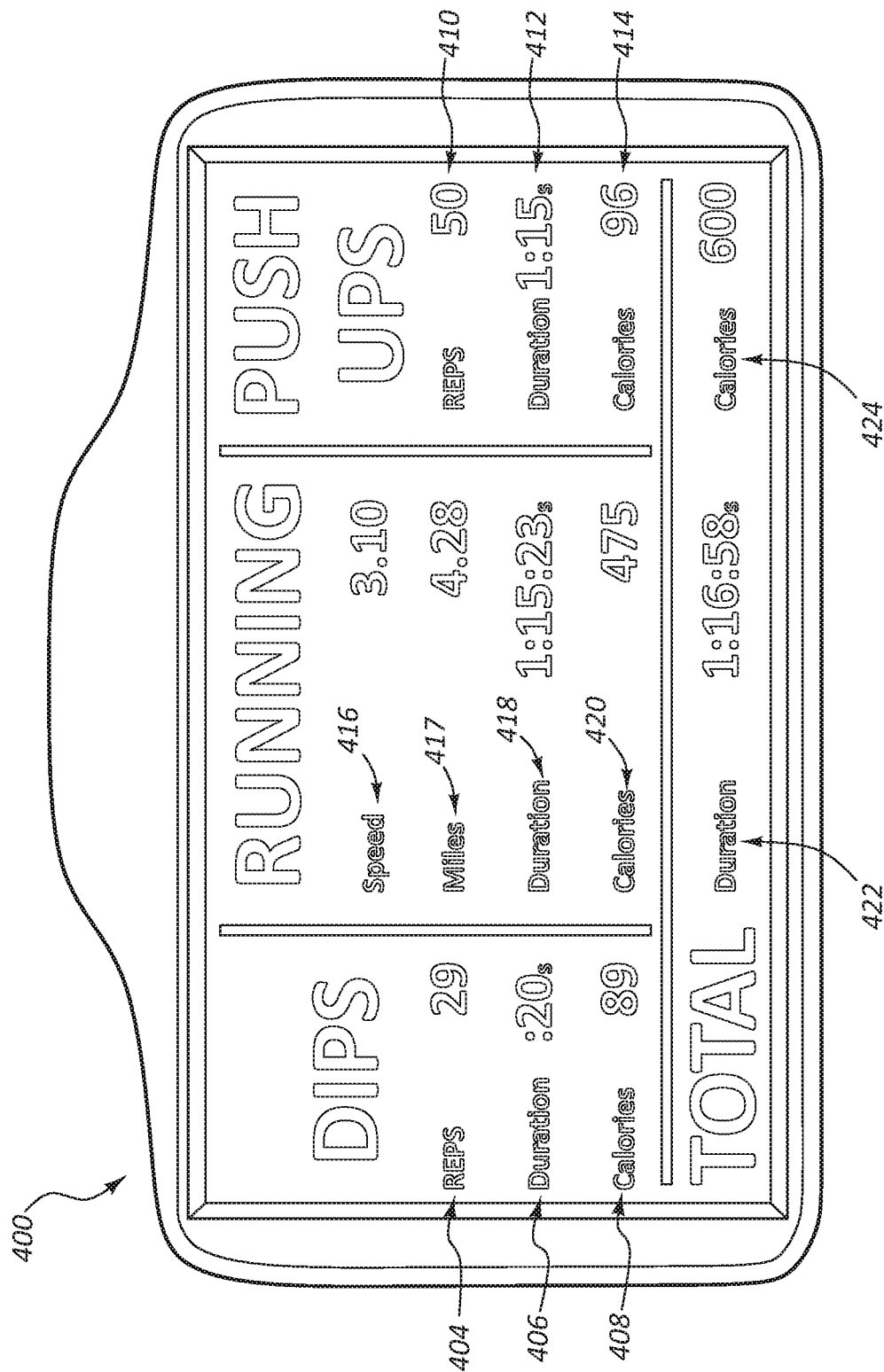
FIG. 4 illustrates a view of an example of a display of a treadmill in accordance with the present disclosure.

FIG. 4 depicts an example of a display 400 in a treadmill. In this example, the display 400 presents to the user a dip repetition number 404, a dip time duration 406, a dip calorie burn 408, a push-up repetition number 410, a push-up time duration 412, a push-up calorie burn 414, a running speed 416, a running distance 417, a running time duration 418, a running calorie burn 420, a total workout duration 422, and a total calorie count 424.

Figure 5:
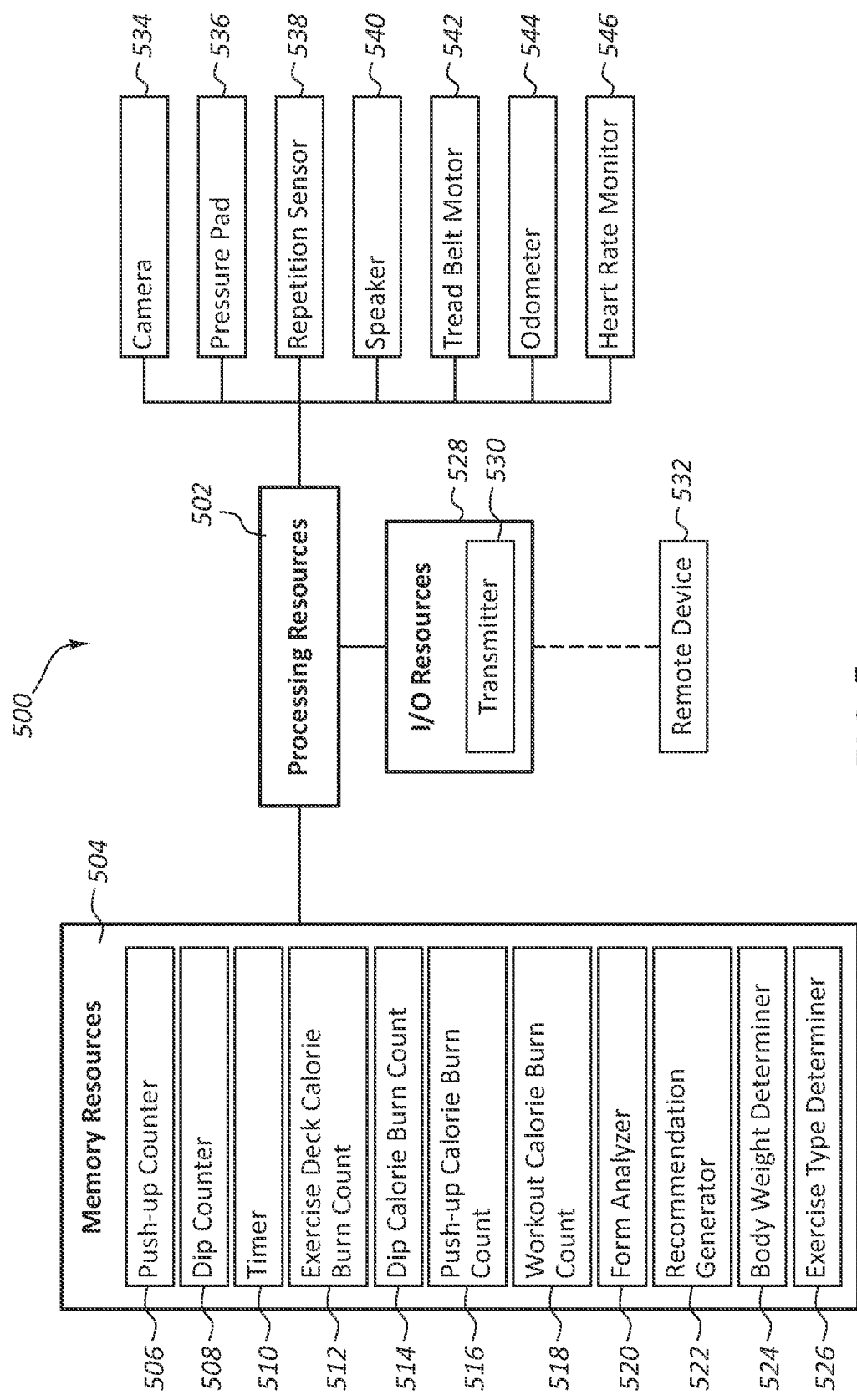
FIG. 5 illustrates a block diagram of an example of a treadmill in accordance with the present disclosure.

FIG. 5 depicts a block diagram of components of an example of a treadmill system 500. In this example, the treadmill system 500 includes processing resources 502 and memory resources 504. The memory resources 504 include a push-up counter 506, a dip counter 508, a timer 510, an exercise deck calorie burn count 512, a dip calorie burn count 514, a push-up calorie burn count 516, a workout calorie burn count 518, a form analyzer 520, a recommendation generator 522, a body weight determiner 524, and an exercise type determiner 526.

The processing resources 502 are also in communication with I/O resources 528, which includes a transmitter 530. The I/O resources may be in communication with a remote device 532.

In illustrated example, the processing resources 502 are also in communication with a camera 534, a pressure pad 536, a repetition sensor 538, a speaker 540, a tread belt motor 542, an odometer 544, and a heart rate monitor 546.

Figure 6:
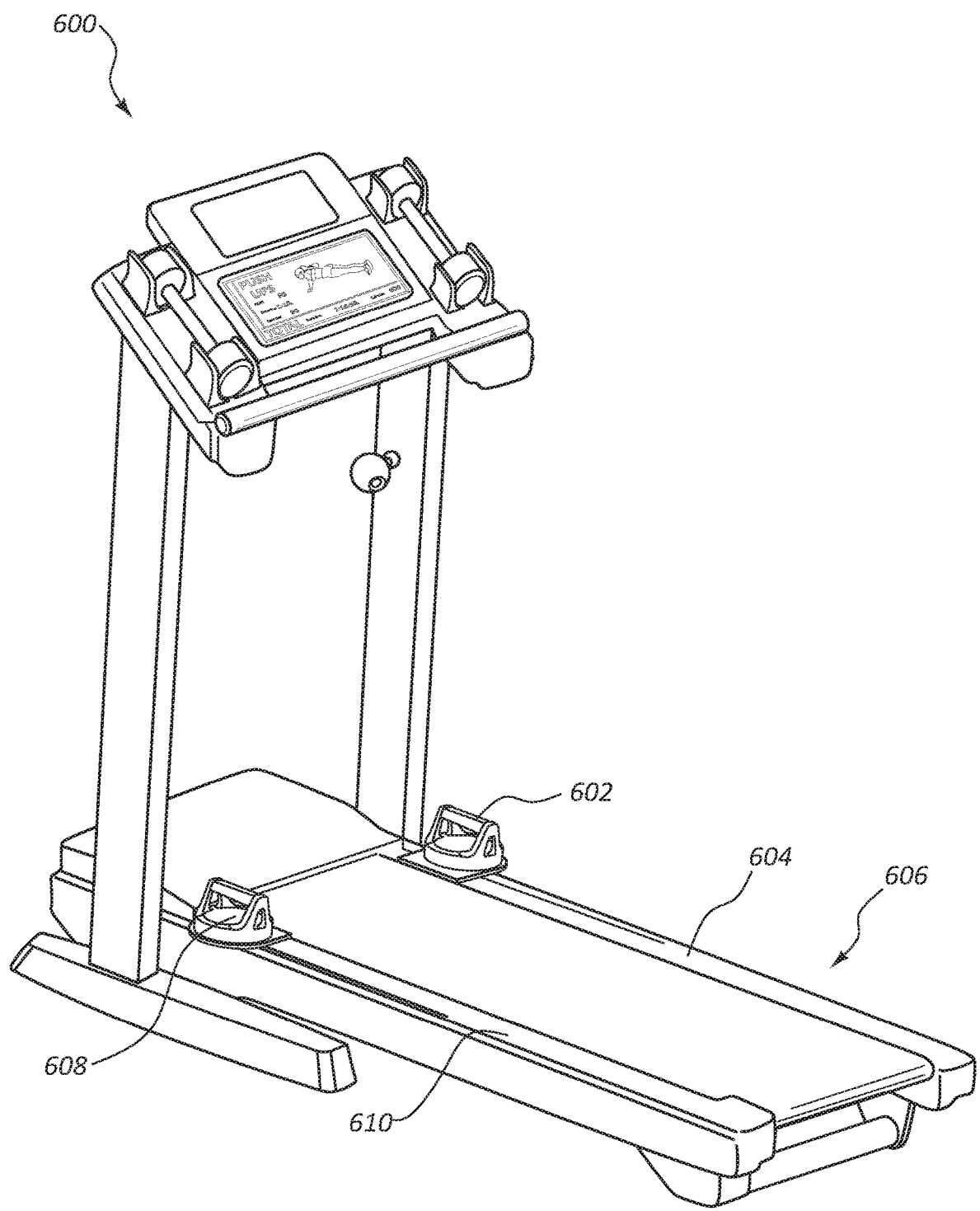
FIG. 6 illustrates a perspective view of an example of a treadmill in accordance with the present disclosure.

FIG. 6 depicts an example of a treadmill 600 with a first push-up bar 602 connected to a first side rail 604 of the exercise deck 606, and a second push-up bar 608 connected to a second side rail 610 of the exercise deck 606. The first and second push-up bars 602, 608 are spaced a human body width apart. A user may grasp the first push-up bar 602 with a first hand and grasp the second push-up bar 608 with a second hand while the user's feet are supported on the exercise deck 606 to perform a push-up exercise.

Figure 7:
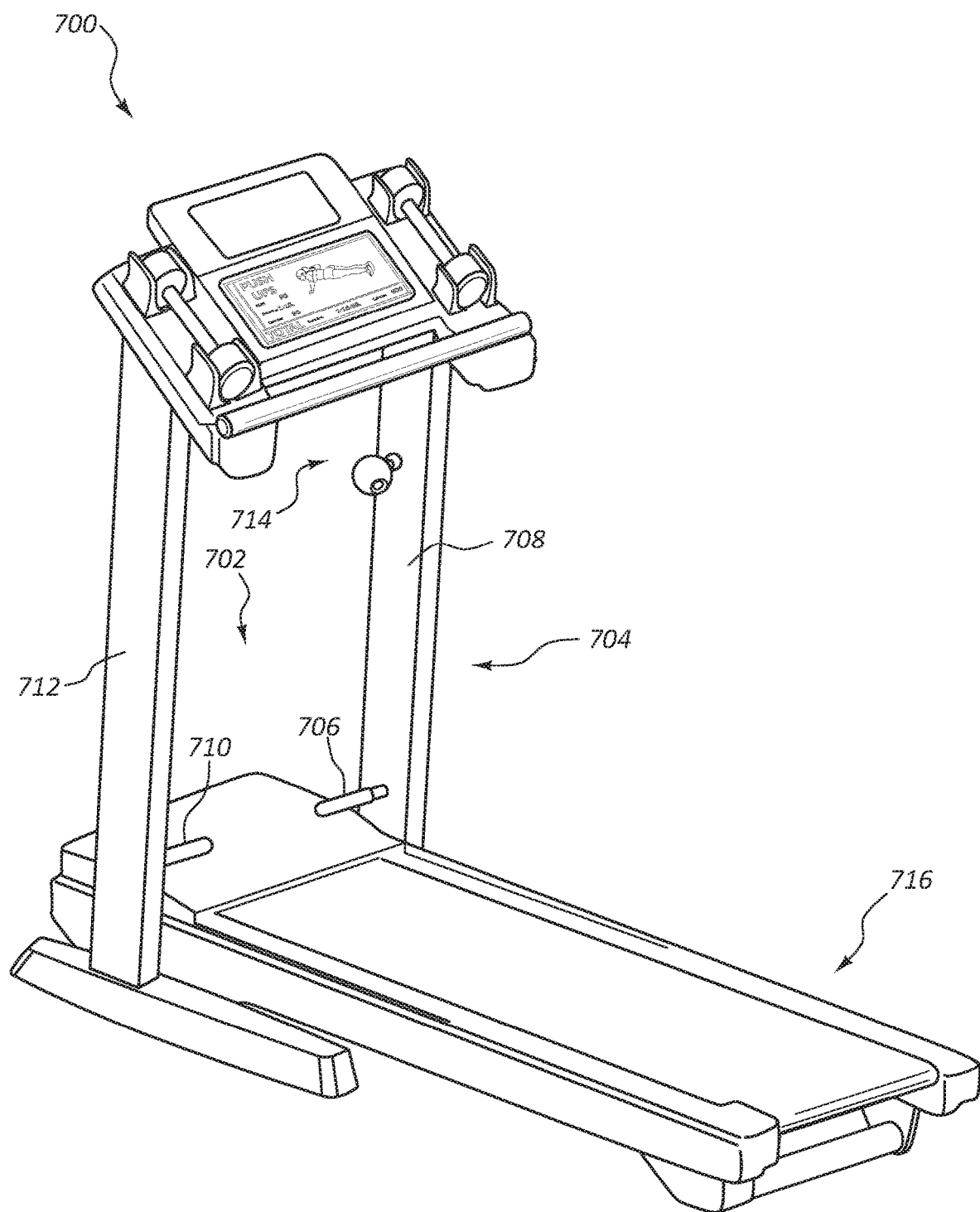
FIG. 7 illustrates a perspective view of an example of a treadmill in accordance with the present disclosure.

FIG. 7 depicts an example of a treadmill 700 with a discontinuous push-up bar 702 attached to the treadmill's frame 704. In this example, the discontinuous push-up bar 702 comprises a first push-up handle 706 connected to a first post 708 of the treadmill's frame 704 and a second push-up handle 710 connected to a second post 712 of the treadmill's frame 704. The first and second push-up handles 706, 710 are oriented to extend towards one another from inside surfaces 714 of the first and second posts 708, 712 and are spaced a human body width apart. A user may grasp the first push-up handle 706 with a first hand and grasp the second push-up handle 710 with a second hand while the user's feet are supported on the exercise deck 716 to perform a push-up exercise.

Figure 8:
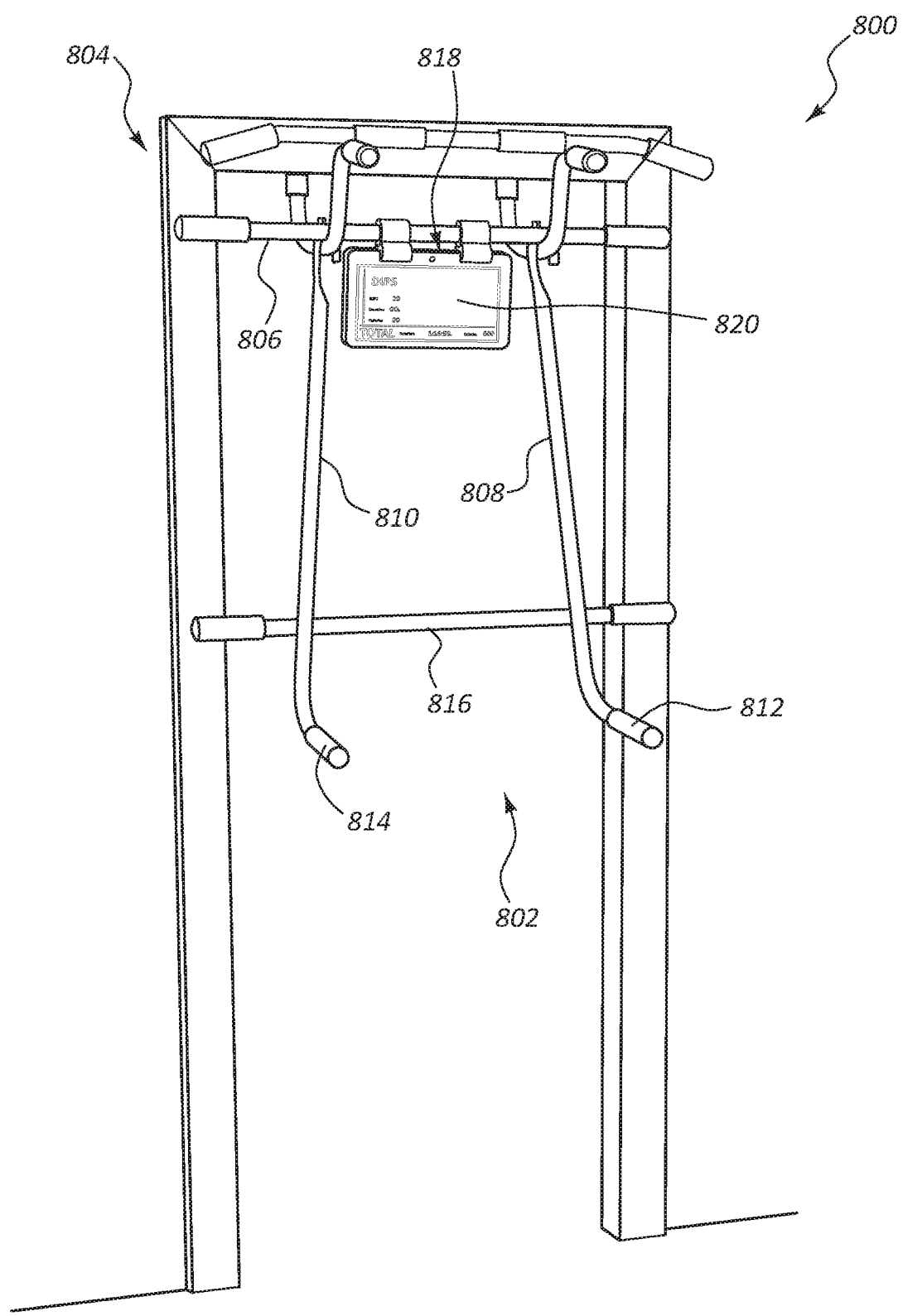
FIG. 8 illustrates a perspective view of an example of a body weight exercise device in accordance with the present disclosure.

FIG. 8 depicts an example of a body weight exercise device 800. In this example, the body weight exercise device 800 includes a frame 802 that has a connection 804 to a door way. However, in other examples, the body weight exercise device 800 may be attached to another structure, such as a wall, building, truss, I-beam, and so forth. The connection 804 may include a beam (not shown) that rests on the upper edge of the door frame and a first cross bar 806 that abuts against the front of the door frame. With the beam resting on the backside of the door frame and the first cross bar abutted against the front of the door frame, the body weight exercise device 800 can securely suspend a user's body weight. A first extension member 808 and a second extension member 810 position a first handle 812 and a second handle 814 below the connection 804 to provide the user hand grips. A second cross bar 816 may be used to provide additional stability.

A camera 818 is incorporated into the body weight exercise device 800 that is angled to detect the movements of the user during the performance of an exercise. The body weight exercise device 800 also includes a display screen 820 where the body weight exercise count can be displayed to the user. In some examples, the number of calories burned by the performance of the body weight exercises is also calculated and presented to the user in the display screen.

Figure 9:
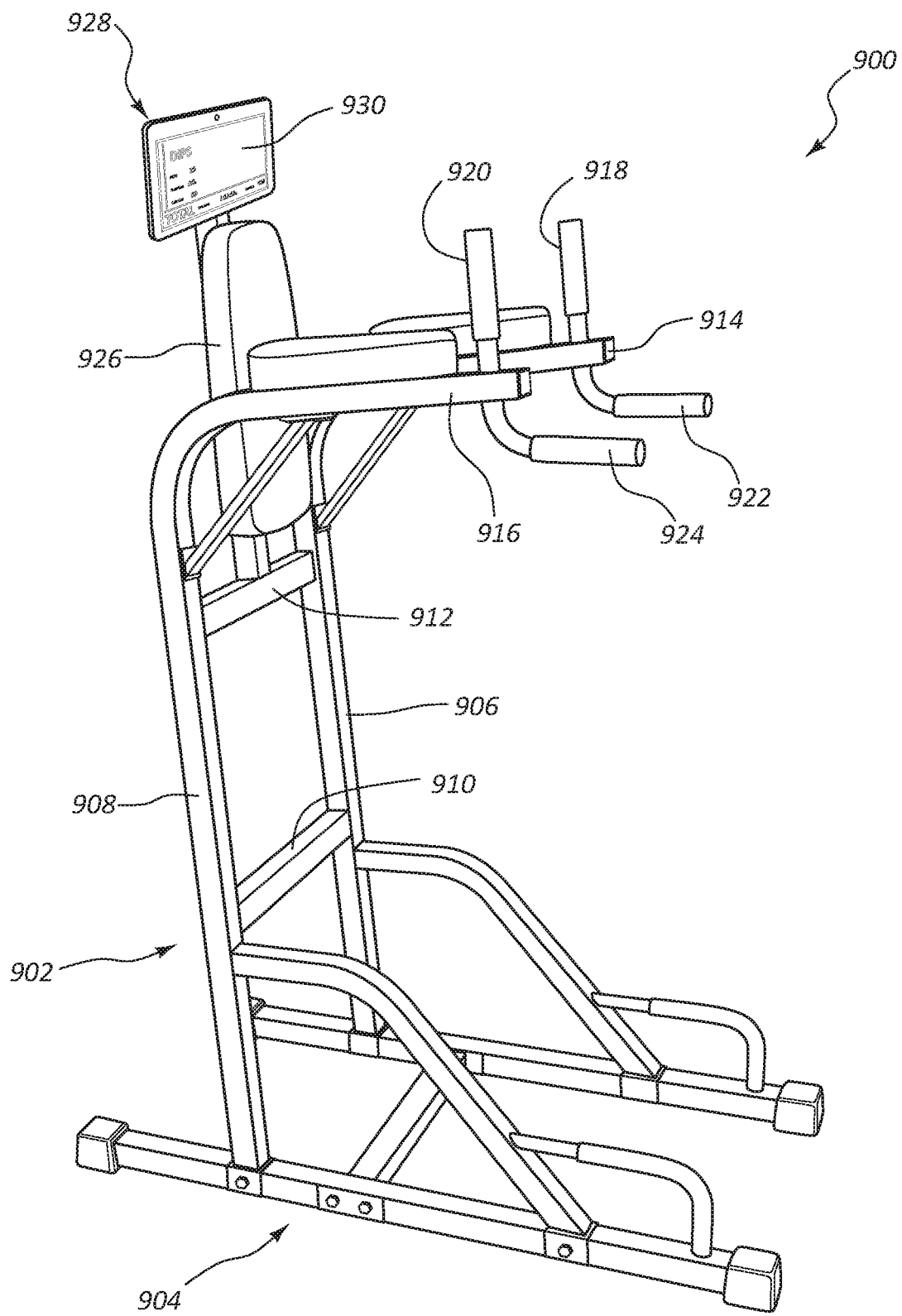
FIG. 9 illustrates a perspective view of an example of a body weight exercise device in accordance with the present disclosure.

FIG. 9 depicts an example of another type of body weight exercise machine 900. In this example, the body weight exercise machine 900 includes a frame 902 that is supported by a base 904. The frame 902 includes a first upright frame post 906 and a second upright frame post 908. A lower cross bar 910 and an upper cross bar 912 are connected to both the first and second upright frame posts 906, 908 to add stability to the body weight exercise machine 900. Additionally, a first support arm 914 is attached to the first upright frame post 906, and a second support arm 916 is attached to the second upright frame post 908. A first handle bar 918 is attached to the first support arm 914 in a transverse orientation with respect to the first support arm 914, and a second handle bar 920 is attached to the second support arm 916 in a transverse orientation with respect to the second support arm 916. Additionally, A third handle bar 922 is attached to the first support arm 914 in an aligned orientation with respect to the first support arm 914, and a fourth handle bar 924 is attached to the second support arm 916 in an aligned orientation with respect to the second support arm 916. A back rest 926 is attached to the upper cross bar 912 to provide stability to the user in the performance of some body weight exercises, such as leg lifts.

A user may grasp the third and fourth handle bars 922, 924 to perform a first type of body weight exercise, such as a dipping exercise. The user may also grasp the first and second handle bars 918, 920, rest his or her arms on the first and second support arms 914, 916, and position his or her back against the back rest 926 to perform another type of body weight exercise, such as leg lifts, knee lifts, or another type of exercise.

The body weight exercise machine includes at least one camera 928 to count the number of body weight exercises that are performed by the user. Additionally, a display screen 930 is also included in the body weight exercise machine 900 to display the body weight exercise count and the associated calorie burn.

General Description of the Invention

In general, the invention disclosed herein may provide the user with an exercise device that allows the user to build strength. Such exercise devices may be incorporated into a treadmill. For example, a dipping station or a push-up station may be incorporated into the treadmill. In such an example, sensors incorporated into the treadmill may be able to track the strength exercises. For instance, the sensors may be able to count the number of times that a user performs a dipping exercise or a push-up exercise. In some examples, such sensors may be incorporated into exercise devices that do not include an exercise deck. For example, a body weight exercise device (i.e. a dipping station) may include sensors that track the repetitions of a dipping exercise and a display screen that presents the repetition number to the user. In some instances, the display screen may also present the number of calories burned by performing the dipping exercise or other type of body weight exercise.

In some examples, the treadmill includes an exercise deck that includes a tread belt that spans between a front pulley at a front end of the treadmill and a rear pulley at a rear end of the treadmill. In some examples, one of the front pulley or the rear pulley is driven by a motor, which causes the tread belt to rotate about the front and rear pulleys. In some examples, a top surface of the tread belt moves from the front pulley to the rear pulley. The speed of the tread belt can be controlled by the user or an exercise program at a pace that the user desires to walk or run. In other examples, the speed of the tread belt may be paced for riding a bicycle or another type of self-propelled exercise device on the exercise deck.

As indicated above, the tread belt is rotated by a motor in some examples. In such an example, a motor may be attached to either of the first pulley, the second pulley, or a transmission component that connects to either the first pulley or the second pulley. As the motor rotates, the motor causes the connected pulley to also rotate. The friction between the connected pulley and the tread belt causes the tread belt and the other pulley to rotate as well. The user can adjust the speed of the tread belt though an input mechanism that sends commands to the motor to adjust the motor's speed. In alternative examples, the tread belt is moved by the user. In such examples, the foot impacts imparted to the tread belt cause the tread belt to rotate. A flywheel attached to either the first pulley or the second pulley may store at least a portion of the inertia of the tread belt's movement to help maintain the tread belt's speed at a relatively consistent speed as the user drives the rotation of the tread belt.

Further, in some examples, the treadmill may include a console that includes input devices to control various aspects of the treadmill. In some cases, the console is supported at a front end of the exercise deck with a first frame post connected to a first side of the treadmill and a second frame post connected to a second side of the treadmill.

While any appropriate type of console may be used with the treadmill, the console may include a display, at least one operations controller, a stop input, speakers, physiological sensors, timers, clocks, other features, or combinations thereof. The display may be used to present videos, scenery, entertainment, images, clocks, physiological conditions of the user, touch screen buttons, other information, or combinations thereof. The operations controller may be used to control various operating parameters of exercises performed on the treadmill. Such operating parameters may include the side to side tilt of the exercise deck, the incline of the exercise deck, the speed of the tread belt, the volume of the speakers, image characteristics of the display, the use of the timers, the operation of the physiological sensors, or other functions. The operations controller may be controlled with an input mechanism such as a push button, a touch screen icon, a lever, a dial, a switch, a microphone, a hand gesture camera, another type of input mechanism, or combinations thereof.

The physiological sensors may track physiological information about the user such as the user's heart rate, blood pressure, oxygen saturation level, pulse, respiration, muscle condition, or other physiological conditions. In some examples, such sensors are incorporated into the console. However, in other examples, such physiological sensors are incorporated into one of the first and second arm rests. The physiological sensors may be used to monitor the health of the user which may assist the user in planning future workouts, in maintaining a target health condition during the workout, in calculating an energy expenditure value representing the amount of energy that the user expended during the workout, in performing other functions, or combinations thereof. Generating such an energy expenditure value may take into account the user's weight, age, height, gender, body composition, other personal information, or combinations thereof.

The processes for calculating the energy expenditure may be in communication with a remote device, which has access to personal information about the user. For example, the remote device may include a profile of the user which includes the user's age, weigh, height, gender, body composition, health conditions, other personal information, or combinations thereof. In some cases, the remote device includes a mobile device, a laptop, a remote computer, a server, a computing device, a data center, another type of device, or combinations thereof. Such profile information may be available to the user through an iFit program available through www.ifit.com and administered through ICON Health and Fitness, Inc. located in Logan, Utah, U.S.A. An example of a program that may be compatible with the principles described in this disclosure is described in U.S. Pat. No. 7,980,996 issued to Paul Hickman. U.S. Pat. No. 7,980,996 is herein incorporated by reference for all that it discloses. However, such profile information may be available through other types of programs. For example, such information may be gleaned from social media websites, blogs, public databases, private databases, other sources, or combinations thereof. In yet other examples, the user information may be accessible through the treadmill. In such an example, the user may input the personal information into the treadmill before, after, or during the workout.

An incline mechanism may be used to control the front to rear slope of the exercise deck. In the cases, the slope of the exercise deck is relatively flat. However, in other examples the incline mechanism may raise or lower a front section of the treadmill to create a different slope. Any appropriate type of incline mechanism may be used to raise and/or lower either a front section or a rear section of the treadmill. Further, any appropriate type of slope may be achieved with the incline mechanism. In some examples, the front to rear slope of the exercise deck may be negative 15.0 degrees where the front section is lower than the rear section. In yet other examples, the front to rear slope may be a positive 45.0 degrees where the front section is higher than the rear section. In other examples, the front to rear slope angle is between negative 45.0 degrees and positive 45.0 degrees. Further, in some embodiments, the exercise deck is capable of changing its side to side tilt angle.

In some cases, the treadmill incorporates a strength device. For example, the treadmill may include a first handle and a second handle directly or indirectly attached to the treadmill's frame that are spaced a human body width apart. In some cases, the first handle is attached proximate the first post of the treadmill's frame, and the second handle is attached proximate the second post of the treadmill's frame. The handles may be movably attached to the treadmill such that the handles can be moved to at least a first orientation and a second orientation. In the first orientation, the handles may be aligned with the length of the exercise deck such that the handles are above the exercise deck. In the second orientation, the handles may be moved outwardly away from a centerline of the exercise deck. In some examples, the handles are slidably connected to the treadmill frame such that the handles remain aligned with the length of the exercise deck's length as the handles move away from the centerline of the exercise deck. In the second orientation, the handles may be moved far enough out that they are no longer above the exercise deck. In alternative examples, the handles may be rotationally connected to the treadmill. In such an example, the handles may pivot away from the centerline of the exercise deck into the second orientation and be positioned in a transverse orientation to the exercise deck's length.

When the handles are in the first orientation, the user may grasp the handles with his or her hands and raise himself or herself off of the exercise deck. The user may then bend his or her knees and lower his or her body downward towards exercise deck without loading the user's weight back to the exercise deck. Often, in this lowered position, the user's elbows are raised towards the user's head and the user's pectoral muscles are stretched. To raise the user to an upper position, the user engages both his pectoral muscles and arm muscles to finish a repetition of a dip exercise. With the handles in the second orientation, the handles are moved out of the way so that they do not interfere with the user performing an aerobic exercise on the exercise deck, such as running, walking, or cycling.

A repetition sensor may be incorporated into the treadmill to count the number of times that the user performs a dipping exercise. In some examples, the repetition sensor can detect when the user is in the lowered position, the upper position, or transitioning there between. Each time that the repetition sensor detects the user's body is in the predetermined position, the repetition sensor can record the count that may result in a counter incrementing the count by one. Such a count may be presented to the user in a display screen incorporated into the treadmill. In other examples, the count may be presented to the user through an audible counter or another mechanism.

Any appropriate type of repetition sensor may be used in accordance with the principles described in the present disclosure. For example, the repetition sensor may be a camera that can detect the user's position or at least some of the positions that the user is in during the performance of the dipping exercise or another body weight exercise. Such a camera may be a camera that operates in the visible light portion of the electromagnetic spectrum. In such an embodiment, the camera may utilize an image recognition program that determines the position of the user based on the color values in the camera's pixels. In another example, the camera operates in the infrared portion of the electromagnetic spectrum. In other examples, the camera is a distance camera that emits a signal and measures the time of flight for a reflection of the signal to return.

In another example, the repetition sensor includes a pressure gauge, strain gauge, or another type of gauge that is in communication with the handles. In such an embodiment, the varying weight loads applied to the handles during the performance of the exercise can be analyzed to determine the number of body weight exercises performed by the user. For example, the forces on the handles during the upward movement of a dipping exercise may exhibit a greater load than when the user is in a resting position or moving in the downward direction. Thus, the expected load increases experienced by the handles can be correlated to the upward movement of the dipping exercise. Accordingly, each time the load increases to a level expected during the performance of a dipping exercise, the counter can be cause to increment the count by one.

In some examples, the sensors may be used as a primary sensor for determining the number repetitions performed by the user. However, in other examples, multiple sensors may be used to determine the number of the repetitions performed by the user or to collect other types of information about the user's performance. For example, a camera may be used as a sensor for collecting repetition information about the user's performance, and a strain gauge may be used to verify that the readings received through the camera appear to be accurate. In some examples, a first camera may be used to verify the accuracy of another camera at a different angle or have a different feature that can corroborate the information gathered from the second camera.

While the examples above have been described with the user performing a dipping exercise with the handles incorporated into the treadmill, any appropriate type of body weight exercise may be performed with the handles. For example, the user may use the handles to perform a leg lift exercise, a knee lift exercise, a dipping exercise, a modified push-up, a modified pull-up, a modified row, another type of body weight exercise, or combinations thereof.

In some examples, the treadmill may also incorporate a push-up bar. The push-up bar may be incorporated into the treadmill in any appropriate manner in accordance with the principles described in the present disclosure. In one example, both the first post and the second post of the treadmill's frame include at least one catch on which an end of a push-up bar can be supported. The catch may be a protrusion from the treadmill post that is made of a material that can support the weight of a push-up bar and the loads applied to the push-up bar. Such catches may be angled slightly upward to cause the push-up bar to roll or otherwise move towards the treadmill's frame posts. In some embodiments, the catches are removably attached to the frame posts. Alternatively, the catches are permanently attached to the frame posts. Each post may include at least one catch that is aligned with another catch on the other post. With the catches aligned, each catch may support one end of the push-up bar. One advantage to securing the push-up bar to the frame posts through the catches is that the push-up bar is easily removed. In some examples, it may be advantageous to move the push-up bar when performing a running or walking exercise on the exercise deck. In other examples, the push-up bar may remain in place without interfering with the performance of a walking or running exercise. Further, each post may have multiple catches with each catch per post located at a different elevations. In such an example, the height of the push-up bar may be changed as desired by the user.

In some situations, it may be desirable to remove the push-up bar from the frame posts when the exercise deck is being inclined during the running or walking exercise performed on the exercise deck. In such an example, the user may manually remove the push-up bar. In other examples, the treadmill may include a mechanism that moves the push-up bar automatically in response to instructing the exercise deck to incline. For example, the catches may move up on a rack and pinion assembly, a screw motor, a hydraulic mechanism, another type of mechanism, or combinations thereof.

In alternative examples, the push-up bar may be permanently attached to the posts. In such an example, the ends of the push-up bar may be screwed or otherwise fastened to the posts. Alternatively, the push-up bar may be welded or integrally formed with the posts. In some cases, the push-up bar is discontinuous. In such an example, a first handle of the push-up bar can be incorporated into the first post and project inward towards the second post, and a second handle of the push-up bar can be incorporated into the second post and project inward towards the first post. In some instances, the distance between the first and second push-up bar handles is sufficient to allow a user to drop between the push-up bar handles while performing push-up exercises.

In yet another example, the push-up handles may be incorporated into the exercise deck. In such an example, a first push-up bar may be incorporated into a first rail of the exercise deck, and a second push-up bar may be incorporated into a second rail of the exercise deck. Each of the first and second push-up bars may be elevated a distance off of the surface of the exercise surface. In this example, when performing push-ups the user may face the surface of the exercise deck while grasping the first push-up bar with his or her first hand and grasping the second push-up bar with his or her second hand.

As described above, the repetition sensor may be used to count the number of push-up exercises executed by the user with the push-up bar. Such repetition sensors may include cameras, strain gauges, pressure gauges, other types of sensors, or combinations thereof.

The number of push-ups, the number of dips, and the number of other types of body weight exercises may be presented to the user in a display incorporated into the treadmill or other type of exercise machine. In some examples, such a display screen may be incorporated into the console. Alternatively, the display screen may be incorporated into an area of the exercise machine where the user can view the display screen during the performance of the strength exercises. In some examples, redundant display screens may be incorporated into the exercise machine so that the user can view the exercise counts while performing different types of exercises.

The sensor may have the intelligence to distinguish between different types of exercises. For example, the sensor may be able to determine when the user is performing an exercise with the handles verses the push-up bar. Further, the sensor may be able to distinguish between when the user is performing different types of exercises with the handles. In such an example, the camera may be able to track the location, direction, and speed of the user during the exercise. For example, if the user is using the handles to perform a modified row, the user grasps the handles with both hands, but the user will be facing upwards. In some examples, the sensor may be able to determine based on the pixel readings that the user is facing upwards and draw a conclusion that the user is performing a row exercise. As the user executes the row exercises, the user's body will alternate between a lower position and a higher position. In such an example, the lower position is proximate the surface of the exercise deck and the upper position is proximate the height the handles. Such lower positions are different than the lower positions of the user during a modified push-up exercise, a dipping exercise, a leg lift exercise, a knee lift exercise, or another type of exercise. Thus, in some examples, the sensor may determine the type of exercise performed by the user based on just the lowered and upper positions. In yet other examples, the sensor may determine the type of exercise based on the angle of the user. In some examples, multiple factors, such as the user's facing direction, angle of the user's body, the lower position, the upper position, and so forth are collectively analyzed to determine the type of exercise being performed by the user. In other examples, just one of the factors may be dispositive for determining the type of exercise being performed by the user.

In addition to knowing the type of exercise, a system incorporated into the exercise machine may have other information about the user. For example, this additional information may include the user's age, gender, weight, height, body composition, health risks, health factors, injuries, and so forth. This information may be used to determine the amount of force needed to move the user during the performance of the exercise being executed by the user. Thus, the system may assign a calorie value to each repetition of the exercise being performed by the user. In some examples, the calorie burn count per exercise is merely the repetition number multiplied by a consistent calorie number calculated based on just the user's personal information. In other examples, the sensor can record and track other conditions that may modify the calorie burn count per repetition. For example, the sensor may record the user's angle in the performance of the exercise. Performing a push-up at a steeper angle (i.e. push-up bar is secured to the highest catch incorporated in the posts), the user may be burning less calories than when the user is performing a push-up at a lower angle (i.e. push-up bar is secured to the lowest catch incorporated into the posts). In some instances, the camera may record the angle during push-ups or other such exercises and modify the number of calories burned per exercise repetition. In some examples, the speed at which the user executes an exercise may also impact the number of calories burned during the performance of the exercise. In some instances, the sensors can also record the user's speed and calculate a modified calorie burn number per exercise repetition. In yet other examples, the sensor can determine the stroke distance per exercise. For example, when a user is performing a dip, the sensor may track how far down the user traveled and adjust the calorie count when the user either falls short of the predetermined stroke distance or exceeds the predetermined stroke distance.

A camera can record the parameters described above with shape recognition programs that can recognize the user's various body parts and identify the location of each of the identified body parts based on the pixel data. Each frame of the camera may be associated with a timestamp. As the user's body parts move during the exercise, the time stamps can be used to determine the speed at which the body parts moved to determine the speed that the exercise is being executed. Additionally, the angles of the user and facing direction of the user can be determined based on the identified location of the user's body parts.

In examples where the exercise machine is a treadmill, the treadmill may contain programs that determine the number of calories burned by the user during the performance of exercises on the exercise deck (i.e. running or walking). The display may present the exercise types and the associated calorie burn for each of the identified exercise types. In one such example, the display screen includes a repetition number for push-ups associated with a calorie burn number, a repetition number for dips associated with a calorie burn number, and a running time duration associated with a speed and a calorie burn number. Additionally, the display screen may present an overall number of calories burned that totals the calories contributed from each of the push-ups, dips, and running exercises. In some examples, the force exerted by the user during the performance of the exercise may be calculated and presented in the display screen. The force may be determined by considering factors such as the user's body weight, the amount of weight loaded to the user, and the speed at which the user accomplished the exercise.

The system may include a combination of hardware and programmed instructions for executing the functions of the system. In this example, the system includes processing resources that are in communication with memory resources. Processing resources include at least one processor and other resources used to process the programmed instructions. The memory resources represent generally any memory capable of storing data such as programmed instructions or data structures used by the system. The programmed instructions shown stored in the memory resources include a push-up counter, a dip counter, a timer, an exercise deck calorie burn count, a dip calorie burn count, a push-up calorie burn count, a workout calorie burn count, a form analyzer, a body weight determiner, and an exercise type determiner.

Further, the processing resources may be in communication with user information and/or workout environment information that may be stored in the memory resources locally or off site. For example, the processing resources may be in communication with a remote device that stores the user information or workout environment information. Such a remote device may be a mobile device, a cloud based device, a computing device, another type of device, or combinations thereof. In some examples, the system communicates with the remote device through the mobile device which relays communications between the system and the remote device. In other examples, the mobile device has access to information about the user and/or workout environment. In some cases, the remote device collects information about the user during his or her workout or in general. In one such example, the exercise machine may send information to the remote device indicating the types of exercises performed by the user, the number of calories burned by the user, the average heart rate of the user during the workout, other types of information about the workout, or combinations thereof. An example of a program that may be compatible with the principles described herein includes the iFit program which is available through www.ifit.com and administered through ICON Health and Fitness, Inc. located in Logan, Utah, U.S.A. An example of a program that may be compatible with the principles described in this disclosure are described in U.S. Pat. No. 7,980,996 issued to Paul Hickman. U.S. Pat. No. 7,980,996 is herein incorporated by reference for all that it discloses. In some examples, the user information accessible through the remote device includes the user's age, gender, body composition, height, weight, health conditions, other types of information, or combinations thereof. Further, the workout environment information that may be accessible to the remote device may include humidity data, temperature data, elevation data, atmospheric pressure data, sunlight exposure data, other types of environmental data, or combinations thereof.

The processing resources, memory resources, and remote devices may communicate over any appropriate network and/or protocol through the input/output resources. In some examples, the input/output resources includes a transceiver for wired and/or wireless communications. For example, these devices may be capable of communicating using the ZigBee protocol, Z-Wave protocol, BlueTooth protocol, Wi-Fi protocol, Global System for Mobile Communications (GSM) standard, another standard, or combinations thereof. In other examples, the user can directly input some information into the system through a digital input/output mechanism, a mechanical input/output mechanism, another type of mechanism, or combinations thereof. For example, such input mechanisms may be incorporated into the console of the exercise machine or at another location on the exercise machine. In some circumstances, the exercise machine includes multiple sensors. In such an example, each of the sensors may communicate as part of the network described above.

The memory resources may include a computer readable storage medium that contains computer readable program code to cause tasks to be executed by the processing resources. The computer readable storage medium may be a tangible and/or non-transitory storage medium. The computer readable storage medium may be any appropriate storage medium that is not a transmission storage medium. A non-exhaustive list of computer readable storage medium types includes non-volatile memory, volatile memory, random access memory, write only memory, flash memory, electrically erasable program read only memory, magnetic based memory, other types of memory, or combinations thereof.

The push-up counter represents programmed instructions that, when executed, cause the processing resources to count the number of push-ups performed by the user. The dip counter represents programmed instructions that, when executed, cause the processing resources to count the number of dips performed by the user. The push-up counter and the dip counter may receive input from a repetition sensor, a camera, a pressure pad, a strain gauge, another type of sensor, or combinations thereof. Such sensors may analyze multiple factors to determine the user's exercise angle, stroke distance, other parameter, or combinations thereof. The timer represents programmed instructions that, when executed, cause the processing resources to determine the time different between the start and finish of an exercise. In some cases, the timer determines the start and finish of a single repetition or just a portion of a repetition (i.e. just the upward movement of an exercise). In other examples, the time is used to determine the time duration for executing a workout.

The exercise deck calorie burn counter represents programmed instructions that, when executed, cause the processing resources to determine the number of calories burned by the user while performing an exercise on the exercise deck. Such exercises may include walking, running, skipping, cycling, backward running, backward walking, another type of exercise, or combinations thereof. The exercise deck calorie burn counter may determine the calorie count by analyzing factors, such as the user's heart rate, the time duration that the exercise was executed, the user's body weight, age, gender, body composition, other factors, or combinations thereof.

The dip calorie burn counter represents programmed instructions that, when executed, cause the processing resources to count the number of calories burned while performing dip exercises with the exercise machine. The push-up calorie burn counter represents programmed instructions that, when executed, cause the processing resources to count the number of calories burned while performing push-up exercises with the exercise machine. The dip calorie burn counter and the push-up calorie burn counter may analyze a number of parameters that are collected by the sensors incorporated into the exercise machine. For instance, the sensors may collect information such as the angle of the user's body during the exercise, the facing direction of the user's body during the exercise, the speed of exercise execution during the exercise, the user's body weight, age, gender, body composition, other factors, or combinations thereof. These factors may be used to fine tune the calculations for determining the amount of calories burned during the push-up and/or dip calorie burn counters.

The workout calorie burn counter represents programmed instructions that, when executed, cause the processing resources to add up the calorie burn counts from each of the exercises performed during the workout. For example, if the user performed push-ups, dips, and running during the workout, the workout calorie burn counter may add up each of the calories from performing push-ups, dips, and running.

The form analyzer represents programmed instructions that, when executed, cause the processing resources to analyze the form of the user during the performance of a strength exercise. In some embodiments, the form analyze determines the stroke length, the angle of the user's body, and other factors that are useful in the calculation of the calorie burn numbers. However, the form analyzer may also determine whether the user is performing the strength exercises properly. For example, the form analyzer may use a recognition program to determine the locations of the user's hands, feet, head, torso, and so forth. Based on the position and angles of these body parts, the form analyzer may determine that the user is executing the exercise with good form, moderate form, or bad form.

The recommendation determiner represents programmed instructions that, when executed, cause the processing resources to generate a recommendation to the user. In some examples, the recommendation is to improve the user's form. For example, if the user is arching his or her back during push-ups, the recommendation determiner may generate a recommendation to straighten the user's back. The recommendation may be presented to the user in the display screen, through a speaker, through a tactile stimulus, through an electronic message, through another communication mechanism, or combinations thereof. While this example has been described with reference to a specific type of recommendations, any appropriate type of recommendation may be made in accordance with the present disclosure. For example, the recommendation may be to do another repetition, perform an exercise slower, perform an exercise faster, improve posture, to bend knees, lean forward, stop performing an exercise, another type of recommendation, or combinations thereof.

The body weight determiner represents programmed instructions that, when executed, cause the processing resources to determine the user's body weight. In some examples, the body weight determiner consults a data field with a value provided by the user. In some examples, the value is provided from a remote device, such as a user profile that contains the user's weight. In such an example, other types of information about the user may be gleaned from the user profile, such as the user's age, gender, body composition, or combinations thereof. In other examples, a sensor is incorporated into the handles, under the exercise deck, or another location on the treadmill and/or exercise machine to determine the user's weight.

The exercise type determiner represents programmed instructions that, when executed, cause the processing resources to determine the type of exercise being performed by the user. In some examples, the exercise type determiner analyzes the factors described above and determines the type of exercise being performed. In some examples, the user may input into the console or another input mechanism the type of exercise being performed. The user may indicate to the system the type of exercise through any appropriate mechanism. In some examples, the user may speak into a microphone associated with the system to indicate the workout type. In other examples, the user may use a button, a touch screen, a lever, or another input/output mechanism, a remote device, another type of device, or combinations thereof. In other examples, the user is participating in a predetermined program that selects the type of exercises for the user to perform. For example, the user may select a program that instructs the user to perform a number of push-ups, dips, and an aerobic exercise on the exercise deck. In such an example, the exercise type determiner may consult the program to determine which type of exercise that the user is being instructed to perform.

Further, the memory resources may be part of an installation package. In response to installing the installation package, the programmed instructions of the memory resources may be downloaded from the installation package's source, such as a portable medium, a server, a remote network location, another location, or combinations thereof. Portable memory media that are compatible with the principles described herein include DVDs, CDs, flash memory, portable disks, magnetic disks, optical disks, other forms of portable memory, or combinations thereof. In other examples, the program instructions are already installed. Here, the memory resources can include integrated memory such as a hard drive, a solid state hard drive, or the like.

In some examples, the processing resources and the memory resources are located within the console, the exercise machine, a mobile device, a remote device, another type of device, or combinations thereof. The memory resources may be part of any of these device's main memory, caches, registers, non-volatile memory, or elsewhere in their memory hierarchy. Alternatively, the memory resources may be in communication with the processing resources over a network. Further, data structures, such as libraries or databases containing user and/or workout information, may be accessed from a remote location over a network connection while the programmed instructions are located locally. Thus, the system may be implemented with the exercise machine, a user device, a mobile device, a phone, an electronic tablet, a wearable computing device, a head mounted device, a server, a collection of servers, a networked device, a watch, or combinations thereof. Such an implementation may occur through input/output mechanisms, such as push buttons, touch screen buttons, voice commands, dials, levers, other types of input/output mechanisms, or combinations thereof. Any appropriate type of wearable device may include, but are not limited to glasses, arm bands, leg bands, torso bands, head bands, chest straps, wrist watches, belts, earrings, nose rings, other types of rings, necklaces, garment integrated devices, other types of devices, or combinations thereof.

While the examples above have been described with reference to strength exercise devices being incorporated into a treadmill, the principles described in the present disclosure are also applicable to the body weight exercise devices, such as dipping stations, vertical knee raise stations, pull-up bars, other types of body weight exercise devices, or combinations thereof. For example, a sensor that determines the number of body weight exercises may be incorporated into a body weight exercise device. Such a sensor may gather other information about the workout, such as the angle of the user, the direction that the user is facing, the speed at which the user is exercising, the number and the durations that the user is taking between repetitions, and so on. Further, the body weight exercise device may also include processing and memory resources to use the gathered data to determine the number of calories that the user has burned. In some cases, the number of calories burned is broken down into calories burned by type of exercise. In other examples, just a total of calories burned is determined and presented. In yet other examples, both a calorie break down and the total number of calories burned is presented.

Such calorie information can be presented in a display screen incorporated into the body weight exercise device.

In one example, the body weight exercise device may be a dipping station that includes a frame that has a connection to a door way. The connection may include a beam that rests on the upper edge of the door frame and a first cross bar that abuts against the front of the door frame. With the beam resting on the backside of the door frame and the first cross bar abutted against the front of the door frame, the body weight exercise device can securely suspend a user's body weight in the air. A first extension member and a second extension member may extend from and position a first handle and a second handle below the connection to provide the user hand grips. A camera may be incorporated into the body dipping station that is angled to detect the movements of the user during the performance of an exercise. The dipping station may also include a display screen where the body weight exercise count can be displayed to the user.

In another example, the body weight exercise machine is a vertical knee raise (VKR) station that includes a frame that is supported by a base on a support surface. The frame includes a first upright frame post and a second upright frame post. Cross bars are connected to both the first and second upright frame posts to add stability to the VKR station. Additionally, a first support arm may be attached to the first upright frame post, and a second support arm may be attached to the second upright frame post. A first handle bar may attached to the first support arm in a transverse orientation with respect to the first support arm, and a second handle bar may be attached to the second support arm in a transverse orientation with respect to the second support arm. Additionally, A third handle bar may be attached to the first support arm in an aligned orientation with respect to the first support arm, and a fourth handle bar may be attached to the second support arm in an aligned orientation with respect to the second support arm. A back rest may be attached to the upper cross bar to provide stability to the user in the performance of some body weight exercises, such as leg lifts.

A user may grasp the third and fourth handle bars to perform a first type of body weight exercise, such as a dipping exercise. The user may also grasp the first and second handle bars, rest his or her arms on the first and second support arms, and position his or her back against the back rest to perform another type of body weight exercise, such as leg lifts, knee lifts, or another type of exercise. Such a VKR station may include at least one camera or another type of repetition sensor to count the number of body weight exercises performed by the user. Additionally, a display screen may also be included in the body weight exercise machine to display the body weight exercise count and the associated calorie burn.

What is claimed is:

1. A treadmill, comprising:
    a frame;
    an exercise deck attached to the frame;
    a console supported by the frame; and
    a first handle movably attached to the frame, the first handle configured to support a body weight of a user during a body weight exercise;
    a repetition sensor to count a number of times that the user performs the body weight exercise; and
    a processor and memory, the memory including programmed instructions which, when accessed by the processor, cause the processor to:
        calculate an exercise deck calorie burn value based on a performance of an exercise with the exercise deck;
        calculate a body weight calorie burn value based on an input from the repetition sensor;
        add the exercise deck calorie burn value to the body weight calorie burn value to generate a workout calorie burn value; and
        present the workout calorie burn value in a display.

2. The treadmill of claim 1, further comprising a second handle movably attached to the frame spaced an adjustable distance away from the first handle.

3. The treadmill of claim 2, wherein the first handle and the second handle are spaced approximately a human body width apart in a first orientation.

4. The treadmill of claim 3, wherein the body weight exercise comprises a dipping exercise.

5. The treadmill of claim 2, wherein the second handle moves laterally with respect to the frame.

6. The treadmill of claim 1, wherein the first handle is pivotally attached to the frame.

7. The treadmill of claim 1, further comprising a weight sensor to generate a weight value of the user applying their body weight to the first handle.

8. The treadmill of claim 1, wherein the display presents the repetition count of the body weight exercise.

9. The treadmill of claim 1, wherein the display presents the body weight exercise calorie burn value based on the performance of the body weight exercise.

10. The treadmill of claim 1, further comprising a tread belt incorporated into the exercise deck wherein the first handle is moved from a first orientation into a second orientation, different from the first orientation, during the performance of the exercise with the exercise deck.

11. The treadmill of claim 1, further comprising a push-up bar attached to the frame.

12. The treadmill of claim 1, further comprising a push-up bar attached to the exercise deck.

13. The treadmill of claim 1, wherein the repetition sensor includes one or more of a pressure gauge or a strain gauge.

14. The treadmill of claim 1, wherein the programmed instructions which, when accessed by the processor, further cause the processor to: analyze varying weight loads applied to the first handle during performance of the body weight exercise.

15. A treadmill, comprising:
    a frame;
    an exercise deck attached to the frame;
    a first handle movably attached to the frame, the first handle configured to support a body weight of a user during a body weight exercise;
    a second handle movably attached to the frame and spaced a first distance from the first handle, the second handle configured to support the body weight of the user during the body weight exercise;
    a repetition sensor to count a number of times that the user performs the body weight exercise; and
    a processor and memory, the memory including programmed instructions which, when accessed by the processor, cause the processor to:
        calculate an exercise deck calorie burn value based on a performance of an exercise with the exercise deck;
        calculate a body weight calorie burn value based on an input from the repetition sensor;
        add the exercise deck calorie burn value to the body weight calorie burn value to generate a workout calorie burn value; and
        present the workout calorie burn value in a display.

16. The treadmill of claim 15, wherein the first handle and the second handle are aligned with a length of the exercise deck in a first orientation, and the first handle and the second handle are transverse to the length of the exercise deck in a second orientation.

17. The treadmill of claim 15, wherein at least one of the first handle and the second handle is rotatably attached to the frame.

18. The treadmill of claim 15, wherein the display presents the repetition count of the body weight exercise based on information gathered from the repetition sensor.

19. A treadmill, comprising:
- a frame including a first post and a second post connected to the frame;
- a console supported by the first post and the second post;
- an exercise deck attached to the frame;
- a first handle movably attached proximate to the first post, the first handle configured to support a body weight of a user during a body weight exercise;
- a second handle movably attached proximate to second post and spaced a first distance from the first handle, the second handle configured to support the body weight of the user during the body weight exercise;
- a repetition sensor to count a number of times that the user performs the body weight exercise;
- a display to present the repetition count of the body weight exercise based on information gathered from the repetition sensor; and
- a processor and memory, the memory comprising programmed instructions which, when accessed by the processor, cause the processor to:
  - calculate an exercise deck calorie burn value based on an exercise deck exercise;
  - calculate a body weight calorie burn value based on the body weight exercise;
  - add the exercise deck calorie burn value to the body weight exercise calorie burn value to generate a workout calorie burn value; and
  - present the workout calorie burn value in the display.

* * * * *